United States Patent
Walsh et al.

(10) Patent No.: US 9,526,632 B2
(45) Date of Patent: Dec. 27, 2016

(54) METHODS OF REPAIRING A JOINT USING A WEDGE-SHAPED IMPLANT

(71) Applicant: Cartiva, Inc., Alpharetta, GA (US)

(72) Inventors: Steven P. Walsh, Marietta, GA (US); Letitia Tudor, Lawrenceville, GA (US); Ernest N. Corrao, Bethel, CT (US); Craig B. Berky, Milford, OH (US); Jonathan P. Bauer, Cincinnati, OH (US); Jeremy Hemingway, Cincinnati, OH (US); Michael Axelrod, Roswell, GA (US)

(73) Assignee: Cartiva, Inc., Alpharetta, GA (US)

( * ) Notice: Subject to any disclaimer, the term of this patent is extended or adjusted under 35 U.S.C. 154(b) by 0 days.

(21) Appl. No.: 14/826,918

(22) Filed: Aug. 14, 2015

(65) Prior Publication Data

US 2016/0038308 A1 Feb. 11, 2016

Related U.S. Application Data

(63) Continuation of application No. 13/480,272, filed on May 24, 2012, now Pat. No. 9,155,543.
(Continued)

(51) Int. Cl.
*A61F 2/28* (2006.01)
*A61F 2/46* (2006.01)
(Continued)

(52) U.S. Cl.
CPC ......... *A61F 2/4603* (2013.01); *A61B 17/1617* (2013.01); *A61F 2/28* (2013.01);
(Continued)

(58) Field of Classification Search
CPC ...... A61F 2/28; A61F 2/30; A61F 2002/2835; A61F 2002/2839; A61F 2/4603
See application file for complete search history.

(56) References Cited

U.S. PATENT DOCUMENTS 3,276,996 A 10/1966 Lazare
3,663,470 A 5/1972 Nishimura et al.
(Continued)

FOREIGN PATENT DOCUMENTS

DE 20218703 U1 3/2003
EP 0222404 A1 5/1987
(Continued)

OTHER PUBLICATIONS

Andrade et al., "Water as a Biomaterial," Trans. Am. Soc. Artif. Intern. Organs, 19:1 (1973).
(Continued)

*Primary Examiner* — Jason-Dennis Stewart
(74) *Attorney, Agent, or Firm* — Knobbe, Martens, Olson & Bear, LLP

(57) ABSTRACT

According to some embodiments, a method of treating a joint of a patient comprises creating a recess in a bone located at or near a targeted joint, wherein the recess includes a generally wedge or truncated cone shape. In one embodiment, the recess in a bone comprises a surface opening along an outer surface of the bone and a bottom opening along the distal end of the recess, such that a diameter of the surface opening is generally smaller than a diameter of the bottom opening. The method additionally comprises providing a joint implant having a wedge or truncated cone shape, wherein a diameter of a top end of the joint implant is generally smaller than a diameter of a bottom end of the joint implant, inserting the joint implant within the recess.

22 Claims, 27 Drawing Sheets

Related U.S. Application Data

(60) Provisional application No. 61/490,507, filed on May 26, 2011.

(51) Int. Cl.
*A61F 2/38* (2006.01)
*A61B 17/16* (2006.01)
*A61F 2/30* (2006.01)

(52) U.S. Cl.
CPC ............ *A61F 2/30756* (2013.01); *A61F 2/38* (2013.01); *A61F 2/4618* (2013.01); *A61F 2002/3021* (2013.01); *A61F 2002/30075* (2013.01); *A61F 2002/30759* (2013.01); *A61F 2002/4627* (2013.01); *A61F 2002/4628* (2013.01)

(56) References Cited

U.S. PATENT DOCUMENTS

| | | |
|---|---|---|
| 3,673,612 A | 7/1972 | Merrill et al. |
| 3,849,238 A | 11/1974 | Gould et al. |
| 3,859,421 A | 1/1975 | Hucke |
| 4,083,906 A | 4/1978 | Schindler et al. |
| 4,158,684 A | 6/1979 | Klawitter et al. |
| 4,205,400 A | 6/1980 | Shen et al. |
| 4,351,069 A | 9/1982 | Ballintyn et al. |
| 4,472,542 A | 9/1984 | Nambu |
| 4,517,295 A | 5/1985 | Bracke et al. |
| 4,524,064 A | 6/1985 | Nambu |
| 4,609,337 A | 9/1986 | Wichterle et al. |
| 4,663,358 A | 5/1987 | Hyon et al. |
| 4,664,857 A | 5/1987 | Nambu |
| 4,693,939 A | 9/1987 | Ofstead |
| 4,731,081 A | 3/1988 | Tiffany et al. |
| 4,734,097 A | 3/1988 | Tanabe et al. |
| 4,738,255 A | 4/1988 | Goble et al. |
| 4,753,761 A | 6/1988 | Suzuki |
| 4,759,766 A | 7/1988 | Buttner-Janz et al. |
| 4,772,284 A | 9/1988 | Jefferies et al. |
| 4,784,990 A | 11/1988 | Nimrod et al. |
| 4,787,905 A | 11/1988 | Loi |
| 4,808,353 A | 2/1989 | Nambu et al. |
| 4,828,493 A | 5/1989 | Nambu et al. |
| 4,851,168 A | 7/1989 | Graiver et al. |
| 4,911,720 A | 3/1990 | Collier |
| 4,916,170 A | 4/1990 | Nambu |
| 4,988,761 A | 1/1991 | Ikada et al. |
| 4,995,882 A | 2/1991 | Destouet et al. |
| 5,047,055 A | 9/1991 | Bao et al. |
| 5,080,674 A | 1/1992 | Jacobs et al. |
| 5,095,037 A | 3/1992 | Iwamitsu et al. |
| 5,106,743 A | 4/1992 | Franzblau et al. |
| 5,106,876 A | 4/1992 | Kawamura |
| 5,108,428 A | 4/1992 | Capecchi et al. |
| 5,108,436 A | 4/1992 | Chu et al. |
| 5,118,667 A | 6/1992 | Adams et al. |
| 5,141,973 A | 8/1992 | Kobayashi et al. |
| 5,171,322 A | 12/1992 | Kenny |
| 5,171,574 A | 12/1992 | Kuberasampath et al. |
| 5,192,326 A | 3/1993 | Bao et al. |
| 5,206,023 A | 4/1993 | Hunziker |
| 5,219,360 A | 6/1993 | Georgiade |
| 5,234,456 A | 8/1993 | Silvestrini |
| 5,244,799 A | 9/1993 | Anderson |
| 5,258,023 A | 11/1993 | Reger |
| 5,258,042 A | 11/1993 | Mehta |
| 5,258,043 A | 11/1993 | Stone |
| 5,260,066 A | 11/1993 | Wood et al. |
| 5,287,857 A | 2/1994 | Mann |
| 5,288,503 A | 2/1994 | Wood et al. |
| 5,290,494 A | 3/1994 | Coombes et al. |
| 5,314,477 A | 5/1994 | Marnay |
| 5,314,478 A | 5/1994 | Oka et al. |
| 5,326,364 A | 7/1994 | Clift, Jr. et al. |
| 5,336,551 A | 8/1994 | Graiver et al. |
| 5,336,767 A | 8/1994 | Della Valle et al. |
| 5,343,877 A | 9/1994 | Park |
| 5,344,459 A | 9/1994 | Swartz |
| 5,346,935 A | 9/1994 | Suzuki et al. |
| 5,397,572 A | 3/1995 | Coombes et al. |
| 5,399,591 A | 3/1995 | Smith et al. |
| 5,401,269 A | 3/1995 | Buttner-Janz et al. |
| 5,409,904 A | 4/1995 | Hecht et al. |
| 5,410,016 A | 4/1995 | Hubbell et al. |
| 5,442,053 A | 8/1995 | Della Valle et al. |
| 5,458,643 A | 10/1995 | Oka et al. |
| 5,458,645 A | 10/1995 | Bertin |
| 5,486,197 A | 1/1996 | Le et al. |
| 5,489,310 A | 2/1996 | Mikhail |
| 5,490,962 A | 2/1996 | Cima et al. |
| 5,492,697 A | 2/1996 | Boyan et al. |
| 5,494,940 A | 2/1996 | Unger et al. |
| 5,502,082 A | 3/1996 | Unger et al. |
| 5,512,475 A | 4/1996 | Naughton et al. |
| 5,522,898 A | 6/1996 | Bao |
| 5,534,028 A | 7/1996 | Bao et al. |
| 5,541,234 A | 7/1996 | Unger et al. |
| 5,545,229 A | 8/1996 | Parsons et al. |
| 5,556,429 A | 9/1996 | Felt |
| 5,556,431 A | 9/1996 | Buttner-Janz |
| 5,578,217 A | 11/1996 | Unger et al. |
| 5,601,562 A | 2/1997 | Wolf et al. |
| 5,626,861 A | 5/1997 | Laurencin et al. |
| 5,645,592 A | 7/1997 | Nicolais et al. |
| 5,656,450 A | 8/1997 | Boyan et al. |
| 5,658,329 A | 8/1997 | Purkait |
| 5,674,241 A | 10/1997 | Bley et al. |
| 5,674,295 A | 10/1997 | Ray et al. |
| 5,674,296 A | 10/1997 | Bryan et al. |
| 5,688,459 A | 11/1997 | Mao et al. |
| 5,700,289 A | 12/1997 | Breitbart et al. |
| 5,705,780 A | 1/1998 | Bao |
| 5,716,416 A | 2/1998 | Lin |
| 5,750,585 A | 5/1998 | Park et al. |
| 5,766,618 A | 6/1998 | Laurencin et al. |
| 5,769,897 A | 6/1998 | Harle |
| 5,789,464 A | 8/1998 | Muller |
| 5,795,353 A | 8/1998 | Felt |
| 5,824,093 A | 10/1998 | Ray et al. |
| 5,824,094 A | 10/1998 | Serhan et al. |
| 5,844,016 A | 12/1998 | Sawhney et al. |
| 5,847,046 A | 12/1998 | Jiang et al. |
| 5,855,610 A | 1/1999 | Vacanti et al. |
| 5,863,297 A | 1/1999 | Walter et al. |
| 5,863,551 A | 1/1999 | Woerly |
| 5,876,452 A | 3/1999 | Athanasiou et al. |
| 5,876,741 A | 3/1999 | Ron |
| 5,880,216 A | 3/1999 | Tanihara et al. |
| 5,900,245 A | 5/1999 | Sawhney et al. |
| 5,916,585 A | 6/1999 | Cook et al. |
| 5,925,626 A | 7/1999 | Della Valle et al. |
| 5,928,239 A | 7/1999 | Mirza |
| 5,935,129 A | 8/1999 | McDevitt et al. |
| 5,944,754 A | 8/1999 | Vacanti |
| 5,947,844 A | 9/1999 | Shimosaka et al. |
| 5,948,829 A | 9/1999 | Wallajapet et al. |
| 5,957,787 A | 9/1999 | Hwang |
| 5,976,186 A | 11/1999 | Bao et al. |
| 5,981,826 A | 11/1999 | Ku et al. |
| 6,001,352 A | 12/1999 | Boyan et al. |
| 6,027,744 A | 2/2000 | Vacanti et al. |
| 6,060,534 A | 5/2000 | Ronan et al. |
| 6,093,205 A | 7/2000 | McLeod et al. |
| 6,102,954 A | 8/2000 | Albrektsson et al. |
| 6,103,255 A | 8/2000 | Levene et al. |
| 6,132,465 A | 10/2000 | Ray et al. |
| 6,156,067 A | 12/2000 | Bryan et al. |
| 6,171,610 B1 | 1/2001 | Vacanti et al. |
| 6,187,329 B1 | 2/2001 | Agrawal et al. |
| 6,206,927 B1 | 3/2001 | Fell |
| 6,224,630 B1 | 5/2001 | Bao et al. |
| 6,231,605 B1 | 5/2001 | Ku |
| 6,255,359 B1 | 7/2001 | Agrawal et al. |

(56) References Cited

U.S. PATENT DOCUMENTS

| | | |
|---|---|---|
| 6,264,695 B1 | 7/2001 | Stoy |
| 6,268,405 B1 | 7/2001 | Yao et al. |
| 6,271,278 B1 | 8/2001 | Park et al. |
| 6,280,475 B1 | 8/2001 | Bao et al. |
| 6,337,198 B1 | 1/2002 | Levene et al. |
| 6,340,369 B1 | 1/2002 | Ferree |
| 6,341,952 B2 | 1/2002 | Gaylo et al. |
| 6,344,058 B1 | 2/2002 | Ferree |
| 6,355,699 B1 | 3/2002 | Vyakarnam et al. |
| 6,358,251 B1 | 3/2002 | Mirza |
| 6,371,984 B1 | 4/2002 | Van Dyke et al. |
| 6,376,573 B1 | 4/2002 | White et al. |
| 6,379,962 B1 | 4/2002 | Holy et al. |
| 6,383,519 B1 | 5/2002 | Sapieszko et al. |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,576 B1 | 8/2002 | Haldimann |
| 6,451,059 B1 | 9/2002 | Janas et al. |
| 6,472,210 B1 | 10/2002 | Holy et al. |
| 6,482,234 B1 | 11/2002 | Weber et al. |
| 6,531,523 B1 | 3/2003 | Davankov et al. |
| 6,533,818 B1 | 3/2003 | Weber et al. |
| 6,534,084 B1 | 3/2003 | Vyakarnam et al. |
| 6,558,421 B1 | 5/2003 | Fell et al. |
| 6,602,291 B1 | 8/2003 | Ray et al. |
| 6,607,558 B2 | 8/2003 | Kuras |
| 6,610,094 B2 | 8/2003 | Husson |
| 6,629,997 B2 | 10/2003 | Mansmann |
| 6,645,248 B2 | 11/2003 | Casutt |
| 6,667,049 B2 | 12/2003 | Janas et al. |
| 6,686,437 B2 | 2/2004 | Buchman et al. |
| 6,707,558 B2 | 3/2004 | Bennett |
| 6,710,126 B1 | 3/2004 | Hirt et al. |
| 6,726,721 B2 | 4/2004 | Stoy et al. |
| 6,733,533 B1 | 5/2004 | Lozier |
| 6,734,000 B2 | 5/2004 | Chin et al. |
| 6,740,118 B2 | 5/2004 | Eisermann et al. |
| 6,773,713 B2 | 8/2004 | Bonassar et al. |
| 6,783,546 B2 | 8/2004 | Zucherman et al. |
| 6,800,298 B1 | 10/2004 | Burdick et al. |
| 6,802,863 B2 | 10/2004 | Lawson et al. |
| 6,827,743 B2 | 12/2004 | Eisermann et al. |
| 6,840,960 B2 | 1/2005 | Bubb |
| 6,849,092 B2 | 2/2005 | Van Dyke et al. |
| 6,855,743 B1 | 2/2005 | Gvozdic |
| 6,875,232 B2 | 4/2005 | Nigam |
| 6,875,386 B1 | 4/2005 | Ward et al. |
| 6,875,442 B2 | 4/2005 | Holy et al. |
| 6,878,384 B2 | 4/2005 | Cruise et al. |
| 6,881,228 B2 | 4/2005 | Zdeblick et al. |
| 6,893,463 B2 | 5/2005 | Fell |
| 6,893,466 B2 | 5/2005 | Trieu |
| 6,923,811 B1 | 8/2005 | Carl et al. |
| 6,960,617 B2 | 11/2005 | Omidian et al. |
| 6,982,298 B2 | 1/2006 | Calabro et al. |
| 6,993,406 B1 | 1/2006 | Cesarano, III et al. |
| 7,008,635 B1 | 3/2006 | Coury et al. |
| 7,012,034 B2 | 3/2006 | Heide et al. |
| 7,022,522 B2 | 4/2006 | Guan et al. |
| 7,048,766 B2 | 5/2006 | Ferree |
| 7,052,515 B2 | 5/2006 | Simonson |
| 7,060,097 B2 | 6/2006 | Fraser et al. |
| 7,066,958 B2 | 6/2006 | Ferree |
| 7,066,960 B1 | 6/2006 | Dickman |
| 7,083,649 B2 | 8/2006 | Zucherman et al. |
| 7,091,191 B2 | 8/2006 | Laredo et al. |
| 7,156,877 B2 | 1/2007 | Lotz et al. |
| 7,186,419 B2 | 3/2007 | Petersen |
| 7,201,774 B2 | 4/2007 | Ferree |
| 7,201,776 B2 | 4/2007 | Ferree et al. |
| 7,214,245 B1 | 5/2007 | Marcolongo et al. |
| 7,217,294 B2 | 5/2007 | Kusanagi et al. |
| 7,235,592 B2 | 6/2007 | Muratoglu et al. |
| 7,250,060 B2 | 7/2007 | Trieu |
| 7,258,692 B2 | 8/2007 | Thelen et al. |
| 7,264,634 B2 | 9/2007 | Schmieding |
| 7,282,165 B2 | 10/2007 | Williams, III et al. |
| 7,291,169 B2 | 11/2007 | Hodorek |
| 7,316,919 B2 | 1/2008 | Childs et al. |
| 7,332,117 B2 | 2/2008 | Higham et al. |
| 7,357,798 B2 | 4/2008 | Sharps et al. |
| 7,377,942 B2 | 5/2008 | Berry |
| 7,682,540 B2 | 3/2010 | Boyan et al. |
| 7,828,853 B2 | 11/2010 | Ek et al. |
| 7,910,124 B2 | 3/2011 | Boyan et al. |
| 8,002,830 B2 | 8/2011 | Boyan et al. |
| 8,142,808 B2 | 3/2012 | Boyan et al. |
| 8,318,192 B2 | 11/2012 | Boyan et al. |
| 8,334,044 B2 | 12/2012 | Myung et al. |
| 8,486,436 B2 | 7/2013 | Boyan et al. |
| 8,895,073 B2 | 11/2014 | Boyan et al. |
| 9,155,543 B2 | 10/2015 | Walsh et al. |
| 2001/0029399 A1 | 10/2001 | Ku |
| 2001/0038831 A1 | 11/2001 | Park et al. |
| 2001/0039455 A1 | 11/2001 | Simon et al. |
| 2001/0046488 A1 | 11/2001 | Vandenburgh et al. |
| 2002/0026244 A1 | 2/2002 | Trieu |
| 2002/0031500 A1 | 3/2002 | MacLaughlin et al. |
| 2002/0034646 A1 | 3/2002 | Canham |
| 2002/0072116 A1 | 6/2002 | Bhatia et al. |
| 2002/0140137 A1 | 10/2002 | Sapieszko et al. |
| 2002/0173855 A1 | 11/2002 | Mansmann |
| 2002/0183845 A1 | 12/2002 | Mansmann |
| 2002/0183848 A1 | 12/2002 | Ray et al. |
| 2002/0187182 A1 | 12/2002 | Kramer et al. |
| 2003/0008395 A1 | 1/2003 | Holy et al. |
| 2003/0008396 A1 | 1/2003 | Ku |
| 2003/0021823 A1 | 1/2003 | Landers et al. |
| 2003/0055505 A1 | 3/2003 | Sicotte et al. |
| 2003/0059463 A1 | 3/2003 | Lahtinen |
| 2003/0082808 A1 | 5/2003 | Guan et al. |
| 2003/0175656 A1 | 9/2003 | Livne et al. |
| 2003/0176922 A1 | 9/2003 | Lawson et al. |
| 2003/0199984 A1 | 10/2003 | Trieu |
| 2003/0220695 A1 | 11/2003 | Sevrain |
| 2003/0233150 A1 | 12/2003 | Bourne et al. |
| 2003/0236573 A1* | 12/2003 | Evans ............... A61L 27/12 623/23.58 |
| 2004/0010048 A1 | 1/2004 | Evans et al. |
| 2004/0024465 A1 | 2/2004 | Lambrecht et al. |
| 2004/0044412 A1 | 3/2004 | Lambrecht et al. |
| 2004/0052867 A1 | 3/2004 | Canham |
| 2004/0059415 A1 | 3/2004 | Schmieding |
| 2004/0059425 A1 | 3/2004 | Schmieding |
| 2004/0063200 A1 | 4/2004 | Chaikof et al. |
| 2004/0064195 A1 | 4/2004 | Herr |
| 2004/0073312 A1 | 4/2004 | Eisermann et al. |
| 2004/0092653 A1 | 5/2004 | Ruberti et al. |
| 2004/0117022 A1 | 6/2004 | Marnay et al. |
| 2004/0143327 A1 | 7/2004 | Ku |
| 2004/0143329 A1 | 7/2004 | Ku |
| 2004/0143333 A1 | 7/2004 | Bain et al. |
| 2004/0147016 A1 | 7/2004 | Rowley et al. |
| 2004/0171143 A1 | 9/2004 | Chin et al. |
| 2004/0172135 A1 | 9/2004 | Mitchell |
| 2004/0220296 A1 | 11/2004 | Lowman et al. |
| 2004/0220669 A1 | 11/2004 | Studer |
| 2004/0220670 A1 | 11/2004 | Eisermann et al. |
| 2004/0249465 A1 | 12/2004 | Ferree |
| 2005/0037052 A1 | 2/2005 | Udipi et al. |
| 2005/0043733 A1 | 2/2005 | Eisermann et al. |
| 2005/0043802 A1 | 2/2005 | Eisermann et al. |
| 2005/0049706 A1 | 3/2005 | Brodke et al. |
| 2005/0055094 A1 | 3/2005 | Kuslich |
| 2005/0055099 A1 | 3/2005 | Ku |
| 2005/0071003 A1 | 3/2005 | Ku |
| 2005/0074877 A1 | 4/2005 | Mao |
| 2005/0079200 A1 | 4/2005 | Rathenow et al. |
| 2005/0090901 A1 | 4/2005 | Studer |
| 2005/0096744 A1 | 5/2005 | Trieu et al. |
| 2005/0106255 A1 | 5/2005 | Ku |
| 2005/0137677 A1 | 6/2005 | Rush |
| 2005/0137707 A1 | 6/2005 | Malek |

(56) References Cited

U.S. PATENT DOCUMENTS

| | | |
|---|---|---|
| 2005/0143826 A1 | 6/2005 | Zucherman et al. |
| 2005/0149196 A1 | 7/2005 | Zucherman et al. |
| 2005/0154462 A1 | 7/2005 | Zucherman et al. |
| 2005/0154463 A1 | 7/2005 | Trieu |
| 2005/0169963 A1 | 8/2005 | Van Dyke et al. |
| 2005/0171608 A1 | 8/2005 | Peterman et al. |
| 2005/0177238 A1 | 8/2005 | Khandkar et al. |
| 2005/0209704 A1 | 9/2005 | Maspero et al. |
| 2005/0216087 A1 | 9/2005 | Zucherman et al. |
| 2005/0228500 A1 | 10/2005 | Kim et al. |
| 2005/0233454 A1 | 10/2005 | Nies et al. |
| 2005/0244449 A1 | 11/2005 | Sayer et al. |
| 2005/0260178 A1 | 11/2005 | Vandenburgh et al. |
| 2005/0261682 A1 | 11/2005 | Ferree |
| 2005/0273176 A1 | 12/2005 | Ely et al. |
| 2005/0277921 A1 | 12/2005 | Eisermann et al. |
| 2005/0278025 A1 | 12/2005 | Ku et al. |
| 2005/0287187 A1 | 12/2005 | Mansmann |
| 2006/0002890 A1 | 1/2006 | Hersel et al. |
| 2006/0052874 A1 | 3/2006 | Johnson et al. |
| 2006/0052875 A1 | 3/2006 | Bernero et al. |
| 2006/0052878 A1 | 3/2006 | Schmieding |
| 2006/0058413 A1 | 3/2006 | Leistner et al. |
| 2006/0064172 A1 | 3/2006 | Trieu |
| 2006/0064173 A1 | 3/2006 | Guederian |
| 2006/0083728 A1 | 4/2006 | Kusanagi et al. |
| 2006/0100304 A1 | 5/2006 | Vresilovic et al. |
| 2006/0121609 A1 | 6/2006 | Yannas et al. |
| 2006/0122706 A1 | 6/2006 | Lo |
| 2006/0136064 A1 | 6/2006 | Sherman |
| 2006/0136065 A1 | 6/2006 | Gontarz et al. |
| 2006/0200250 A1 | 9/2006 | Ku |
| 2006/0206209 A1 | 9/2006 | Cragg et al. |
| 2006/0224244 A1 | 10/2006 | Thomas et al. |
| 2006/0229721 A1 | 10/2006 | Ku |
| 2006/0235541 A1 | 10/2006 | Hodorek |
| 2006/0257560 A1 | 11/2006 | Barone et al. |
| 2006/0259144 A1 | 11/2006 | Trieu |
| 2006/0282165 A1 | 12/2006 | Pisharodi |
| 2006/0282166 A1 | 12/2006 | Molz et al. |
| 2006/0287730 A1 | 12/2006 | Segal et al. |
| 2006/0293561 A1 | 12/2006 | Abay |
| 2006/0293751 A1 | 12/2006 | Lotz et al. |
| 2007/0010889 A1 | 1/2007 | Francis |
| 2007/0014867 A1 | 1/2007 | Kusanagi et al. |
| 2007/0032873 A1 | 2/2007 | Pisharodi |
| 2007/0038301 A1 | 2/2007 | Hudgins |
| 2007/0043441 A1 | 2/2007 | Pisharodi |
| 2007/0067036 A1 | 3/2007 | Hudgins et al. |
| 2007/0073402 A1 | 3/2007 | Vresilovic et al. |
| 2007/0093906 A1 | 4/2007 | Hudgins et al. |
| 2007/0106387 A1 | 5/2007 | Marcolongo et al. |
| 2007/0116678 A1 | 5/2007 | Sung et al. |
| 2007/0118218 A1 | 5/2007 | Hooper |
| 2007/0118225 A1 | 5/2007 | Hestad et al. |
| 2007/0134333 A1 | 6/2007 | Thomas et al. |
| 2007/0135922 A1 | 6/2007 | Trieu |
| 2007/0142326 A1 | 6/2007 | Shue |
| 2007/0162135 A1 | 7/2007 | Segal et al. |
| 2007/0164464 A1 | 7/2007 | Ku |
| 2007/0167541 A1 | 7/2007 | Ruberti et al. |
| 2007/0168039 A1 | 7/2007 | Trieu |
| 2007/0173951 A1 | 7/2007 | Wijlaars et al. |
| 2007/0179606 A1 | 8/2007 | Huyghe et al. |
| 2007/0179614 A1 | 8/2007 | Heinz et al. |
| 2007/0179615 A1 | 8/2007 | Heinz et al. |
| 2007/0179617 A1 | 8/2007 | Brown et al. |
| 2007/0179618 A1 | 8/2007 | Trieu et al. |
| 2007/0179620 A1 | 8/2007 | Seaton, Jr. et al. |
| 2007/0179621 A1 | 8/2007 | McClellan, III et al. |
| 2007/0179622 A1 | 8/2007 | Denoziere et al. |
| 2007/0196454 A1 | 8/2007 | Stockman et al. |
| 2007/0202074 A1 | 8/2007 | Shalaby |
| 2007/0203095 A1 | 8/2007 | Sadozai et al. |
| 2007/0203580 A1 | 8/2007 | Yeh |
| 2007/0208426 A1 | 9/2007 | Trieu |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0213825 A1 | 9/2007 | Thramann |
| 2007/0224238 A1 | 9/2007 | Mansmann et al. |
| 2007/0225823 A1 | 9/2007 | Hawkins et al. |
| 2007/0227547 A1 | 10/2007 | Trieu |
| 2007/0233135 A1 | 10/2007 | Gil et al. |
| 2007/0233259 A1 | 10/2007 | Muhanna et al. |
| 2007/0265626 A1 | 11/2007 | Seme |
| 2007/0270876 A1 | 11/2007 | Kuo et al. |
| 2007/0270970 A1 | 11/2007 | Trieu |
| 2007/0270971 A1 | 11/2007 | Trieu et al. |
| 2007/0299540 A1 | 12/2007 | Ku |
| 2008/0004707 A1 | 1/2008 | Cragg et al. |
| 2008/0015697 A1 | 1/2008 | McLeod et al. |
| 2008/0021563 A1 | 1/2008 | Chudzik |
| 2008/0031962 A1 | 2/2008 | Boyan et al. |
| 2008/0045949 A1 | 2/2008 | Hunt et al. |
| 2008/0051889 A1 | 2/2008 | Hodorek |
| 2008/0057128 A1 | 3/2008 | Li et al. |
| 2008/0075657 A1 | 3/2008 | Abrahams et al. |
| 2008/0077242 A1 | 3/2008 | Reo et al. |
| 2008/0077244 A1 | 3/2008 | Robinson |
| 2008/0097606 A1 | 4/2008 | Cragg et al. |
| 2008/0103599 A1 | 5/2008 | Kim et al. |
| 2008/0114367 A1 | 5/2008 | Meyer |
| 2008/0125870 A1 | 5/2008 | Carmichael et al. |
| 2008/0131425 A1 | 6/2008 | Garcia et al. |
| 2008/0145404 A1 | 6/2008 | Hill et al. |
| 2008/0154372 A1 | 6/2008 | Peckham |
| 2008/0166329 A1 | 7/2008 | Sung et al. |
| 2008/0279941 A1 | 11/2008 | Boyan et al. |
| 2008/0279943 A1 | 11/2008 | Boyan et al. |
| 2009/0043398 A1 | 2/2009 | Yakimicki et al. |
| 2009/0182421 A1 | 7/2009 | Silvestrini et al. |
| 2009/0263446 A1 | 10/2009 | Boyan et al. |
| 2010/0161073 A1 | 6/2010 | Thomas et al. |
| 2010/0198258 A1 | 8/2010 | Heaven et al. |
| 2011/0040332 A1 | 2/2011 | Culbert et al. |
| 2011/0172771 A1 | 7/2011 | Boyan et al. |
| 2011/0208305 A1* | 8/2011 | Malinin .................. A61F 2/08 623/13.14 |
| 2011/0270400 A1 | 11/2011 | Kita et al. |
| 2013/0211451 A1 | 8/2013 | Wales et al. |
| 2014/0214080 A1 | 7/2014 | Wales et al. |
| 2015/0351815 A1 | 12/2015 | Wales et al. |

FOREIGN PATENT DOCUMENTS

| | | |
|---|---|---|
| EP | 0222407 A2 | 5/1987 |
| EP | 0346129 A1 | 12/1989 |
| EP | 0505634 A1 | 9/1992 |
| EP | 0410010 B1 | 10/1993 |
| EP | 0411105 B1 | 6/1995 |
| EP | 0845480 A1 | 6/1998 |
| EP | 0919209 A1 | 6/1999 |
| EP | 1287796 A1 | 3/2003 |
| EP | 1030697 B1 | 8/2003 |
| EP | 1344538 A1 | 9/2003 |
| EP | 1584338 A2 | 10/2005 |
| EP | 1482996 B1 | 11/2005 |
| GB | 02056882 A | 3/1981 |
| GB | 02128501 A | 5/1984 |
| JP | 02-184580 | 7/1990 |
| JP | 04053843 | 2/1992 |
| JP | 07247365 | 9/1995 |
| JP | 11035732 | 2/1999 |
| JP | 2005-199054 | 7/2005 |
| JP | 2006-101893 | 4/2006 |
| WO | WO90/07545 A2 | 7/1990 |
| WO | WO90/07575 A1 | 7/1990 |
| WO | WO90/10018 A1 | 9/1990 |
| WO | WO93/16664 A1 | 9/1993 |
| WO | WO94/01483 A1 | 1/1994 |
| WO | WO95/25183 A1 | 9/1995 |
| WO | WO97/06101 A1 | 2/1997 |

(56) References Cited

FOREIGN PATENT DOCUMENTS

| WO | WO97/46178 A1 | 12/1997 |
|---|---|---|
| WO | WO98/02146 A2 | 1/1998 |
| WO | WO98/50017 A1 | 11/1998 |
| WO | WO99/25391 A2 | 5/1999 |
| WO | WO99/34845 A1 | 7/1999 |
| WO | WO00/30998 A1 | 6/2000 |
| WO | WO00/42991 A1 | 7/2000 |
| WO | WO00/62829 A1 | 10/2000 |
| WO | WO00/66191 A1 | 11/2000 |
| WO | WO01/02033 A1 | 1/2001 |
| WO | WO01/22902 A2 | 4/2001 |
| WO | WO01/59160 A1 | 8/2001 |
| WO | WO01/64030 A1 | 9/2001 |
| WO | WO01/70436 A1 | 9/2001 |
| WO | WO01/91822 A1 | 12/2001 |
| WO | WO02/09647 A2 | 2/2002 |
| WO | WO02/30480 A1 | 4/2002 |
| WO | WO02/064182 A3 | 8/2002 |
| WO | WO03/030787 A1 | 4/2003 |
| WO | WO03/092760 A1 | 11/2003 |
| WO | WO2004/060554 A1 | 7/2004 |
| WO | WO2004/101013 A1 | 11/2004 |
| WO | WO2005/077013 A2 | 8/2005 |
| WO | WO2005/077304 A1 | 8/2005 |
| WO | WO2005/097006 A2 | 10/2005 |
| WO | WO2006/018531 A2 | 2/2006 |
| WO | WO2006/019634 A1 | 2/2006 |
| WO | WO2006/030054 A1 | 3/2006 |
| WO | WO2006/034365 A2 | 3/2006 |

OTHER PUBLICATIONS

Ariga et al., "Immobilization of Microorganisms with PVA Hardened by Iterative Freezing and Thawing," Journal of Fermentation Technology, 65(6): pp. 651-658 (1987).
Boyan et al., "Effect of Titanium Surface Characteristics on Chondrocytes and Osteoblasts in Vitro," Cells and Materials, vol. 5, No. 4, pp. 323-335 (1995).
Boyan et al., "Osteoblast-Mediated Mineral Deposition in Culture is Dependent on Surface Microtopography," Calcif. Tissue Int., 71:519-529 (2002).
Bray et al., Poly(vinyl alcohol) Hydrogels for Synthetic Articular Cartilage Material, M. Biomed. Mater. Res., vol. 7, pp. 431-443.
Brunette, "The Effects of Implant Surface Topography on the Behavior of Cells," Int. J. Oral Maxillofac Implants, 3:231-240 (1988).
Chen et al., "Boundary layer infusion of heparin prevents thrombosis and reduces neointimal hyperplasia in venous polytetrafluoroethylene grafts without system anticoagulation," J. Vascular Surgery, 22:237-247 (1995).
Chu et al., "Polyvinyl Alcohol Cryogel: An Ideal Phantom Material for MR Studies of Arterial Elasticity," Magnetic Resonance in Medicine, v. 37, pp. 314-319 (1997).
Hickey et al., "Mesh size and diffusive characteristics of semicrystalline poly(vinyl alcohol) membranes prepared by freezing/thawing techniques," Journal of Membrane Science, 107(3), pp. 229-237 (1995).
Hoffman et al., "Interactions of Blood and Blood Components at Hydrogel Interfaces," Ann. New York Acad. Sci., 283:372-382 (1977).
Hunt, Knee Simulation, Creep, and Friction Tests of Poly(Vinyl Alcohol) Hydrogels Manufactured Using Injection Molding and Solution Casting, Thesis for M.S., University of Notre Dame (Jul. 2006).
Katta et al., "Friction and wear behavior of poly(vinyl alcohol)/poly(vinyl pyrrolidone) hydrogels for articular cartilage replacement," Journal of Biomedical Materials Research, vol. 83A, pp. 471-479 (2007).
Kieswetter et al., "The Role of Implant Surface Characteristics in the Healing of Bone," Crit. Rev. Oral Biol. Med., 7(4):329-345 (1996).
Kieswetter et al., "Surface roughness modulates the local production of growth factors and cytokines by osteoblast-like MG-63 cells," Journal of Biomedical Materials Research, vol. 32, pp. 55-63 (1996).
Kobayashi et al., "Characterization of a polyvinyl alcohol-hydrogel artificial articular cartilage prepared by injection molding," J. Biomater. Sci. Polymer Edn., 15(6): 741-751 (2003).
Kobayashi et al., "Development of an artificial meniscus using polyvinyl alcohol-hydrogel for early return to, and continuance of, athletic life in sportspersons with severe meniscus injury. I: mechanical evaluation." The Knee, 10 (2003); 47-51.
Kohavi et al., "Markers of primary mineralization are correlated with bone-bonding ability of titanium or stainless steel in vivo," Clin. Oral. Impl. Res., 6:1-13 (1995).
Koutsopoulos et al., "Calcification of porcine and human cardiac valves: testing of various inhibitors for antimineralization," J. Mater. Sci. Mater. Med., 9:421-424 (1998).
Kwak, BK, et al., "Chitin-based Embolic Materials in the Renal Artery of Rabbits: Pathologic Evaluation of an Absorbable Particulate Agent", Radiology, 236:151-158 (2005).
Landolt et al., "Electrochemical micromachining, polishing and surface structuring of metals: fundamental aspects and new developments", Elsevier Science Ltd., pp. 3185-3201 (2003).
Lazzeri et al., "Physico-chemical and mechanical characterization of hydrogels of poly(vinyl alcohol) and hyaluronic acid," J. Mater. Sci. In Med., 5:862-867 (1994).
Liao et al., "Response of rat osteoblast-like cells to microstructured model surfaces in vitro," Biomaterials, 24, pp. 649-654 (2003).
Lozinsky et al., "Study of cryostructurization of polymer systems. VII. Structure formation under.freezing of poly(vinyl alcohol) acqueous solutions," Colloid & Polymer Science, vol. 264, pp. 19-24 (1986).
Lozinsky et al., "Study of Cryostructuration of Polymer Systems. XII. Poly(vinyl alcohol) Cryogels: Influence of Low-Molecular Electrolytes," Journal of Applied Polymer Science, vol. 61, pp. 1991-1998 (1996).
Lozinsky et al., "Study of Cryostructuration of Polymer Systems. XI. The Formation of PVA Cryogels by Freezing-Thawing the Polymer Aqueous Solutions Containing Additives of Some Polyols," Journal of Applied Polymer Science, vol. 58, pp. 171-177 (1995).
Lozinsky et al., "Poly(vinyl alcohol) cryogels employed as matrices for cell immobilization. 2. Entrapped cells resemble porous fillers in their effects on the properties of PVA-cryogel carrier," Enzyme and Microbial Technology, vol. 20, No. 3, pp. 182-190 (1997).
Lozinsky et al., "Poly(vinyl alcohol) cryogels employed as matrices for cell immobilization. 3. Overview of recent research and developments," Enzyme and Microbial Technology, vol. 23, No. 3-4, pp. 227-242 (1998).
Lusta et al., "Immobilization of fungus *Aspergillus* sp. by a novel cryogel technique for production of extracellular hydrolytic enzymes", Process Biochemistry, vol. 35, pp. 1177-1182 (2000).
Ma et al., "Friction Properties of novel PVP/PVA blend hydrogels as artificial cartilage," Journal of Biomedical Materials Research, vol. 93A, pp. 1016-1019 (2010).
Martin et al., "Effect of titanium surface roughness on proliferation, differentiation, and protein synthesis of human osteoblast-like cells (MG63)," Journal of Biomedical Materials Research, vol. 29, pp. 389-401 (1995).
Nagura et al., "Structure of poly(vinyl alcohol) hydrogel prepared by repeated freezing and melting," Polymer, 30:762-765 (1989).
Nakashima et al., "Study on Wear Reduction Mechanisms of Artificial Cartilage by Synergistic Protein Boundary Film Formation," Japan Soc'y of Mech. Eng'r Int'l J., Series C, vol. 48, No. 4, pp. 555-561 (2005).
Oka et al., "Development of an Artificial Articular Cartilage", Clinical Materials, vol. 6, pp. 361-381 (1990).
Ong et al., "Osteoblast Responses to BMP-2-Treated Titanium In Vitro," The International Journal of Oral & Maxillofacial Implants, vol. 12, No. 5, pp. 649-654 (1997).
Peppas et al., "Reinforced uncrosslinked poly(vinyl alcohol) gels produced by cyclic freezing-thawing processes: a short review," Journal of Controlled Release, 16(3): 305-310 (1991).

(56) References Cited

OTHER PUBLICATIONS

Peppas et al., "Structure of Hydrogels by Freezing-Thawing Cyclic Processing," Bulletin of the American Physical Society, 36:582 (1991).
Peppas et al., "Controlled release from poly(vinyl alcohol) gels prepared by freezing-thawing processes," Journal of Controlled Release, vol. 18, pp. 95-100 (1992).
Peppas et al., "Ultrapure poly(vinyl alcohol) hydrogels with mucoadhesive drug delivery characteristics," European Journal of Pharmaceutics and Biopharmaceutics, 43(1): 51-58 (1997).
Ratner et al., Biomaterials Science an Introduction to Materials in Medicine, Academic Press, pp. 52, 53, & 62 (1996).
Ricciardi et al., "Structure and Properties of Poly(vinyl alcohol) Hydrogels Obtained by Freeze/Thaw Techniques," Macromol. Symp., 222: 49-63 (2005).
Schwartz et al., "Underlying Mechanisms at the Bone-Biomaterial Interface," Journal of Cellular Biochemistry, 56:340-347 (1994).
Singh et al., "Polymeric Hydrogels: Preparation and Biomedical Applications," J. Sci. Ind. Res., 39:162-171 (1980).
Stauffer et al., "Poly(vinyl alcohol) hydrogels prepared by freezing-thawing cyclic processing," Polymer 33(1818):3932-3936 (1992).
Stewart et al., "Protein release from PVA gels prepared by freezing and thawing techniques," Proc. Int. Symp. Controlled Release Bioact. Mater., 26th, 1004-1005 (1999).
Szczesna-Antezak et al., "*Bacillus subtilis* cells immobilised in PVA-cryogels," Biomolecular Engineering, vol. 17, pp. 55-63 (2001).
The American Heritage ® Science Dictionary [online], Houghton Mifflin Company, 2002 [retrieved on Jun. 3, 2008]. Retrieved from the internet: <URL: http://dictionary.reference.com/browse/pore>.
Watase et al., "Rheological and DSC Changes in Poly(vinyl alcohol) Gels Induced by Immersion in Water," Journal of Polymer Science, Polym. Phys. Ed, 23(9): 1803-1811 (1985).
Watase et al., "Thermal and rheological properties of poly(vinyl alcohol) hydrogels prepared by repeated cycles of freezing and thawing," Makromol. Chem., v. 189, pp. 871-880 (1988).
Willcox et al., "Microstructure of Poly(vinyl alcohol) Hydrogels Produced by Freeze/Thaw Cycling," Journal of Polymer Sciences: Part B: Polymer Physics, vol. 37, pp. 3438-3454 (1999).
WordNet ® 3.0 [online], Princeton University, 2006 [retrieved on Aug. 6, 2008]. Retrieved from the Internet: <URL: http://dictionary.reference.com/browse/mesh>.
Yamaura et al., "Properties of Gels Obtained by Freezing/Thawing of Poly(vinyl Alcohol)/Water/Dimethyl Sulfoxide Solutions," J. Appl. Polymer Sci., 37:2709-2718 (1989).
Yokoyama et al., "Morphology and structure of highly elastic poly(vinyl alcohol) hydrogel prepared by repeated freezing-and-melting", Colloid & Polymer Science, vol. 264, No. 7, pp. 595-601 (1986).
Zheng-Qiu et al., "The development of artificial articular cartilage—PVA-hydrogel," Bio-Medical Materials and Engineering, vol. 8, pp. 75-81 (1998).

\* cited by examiner

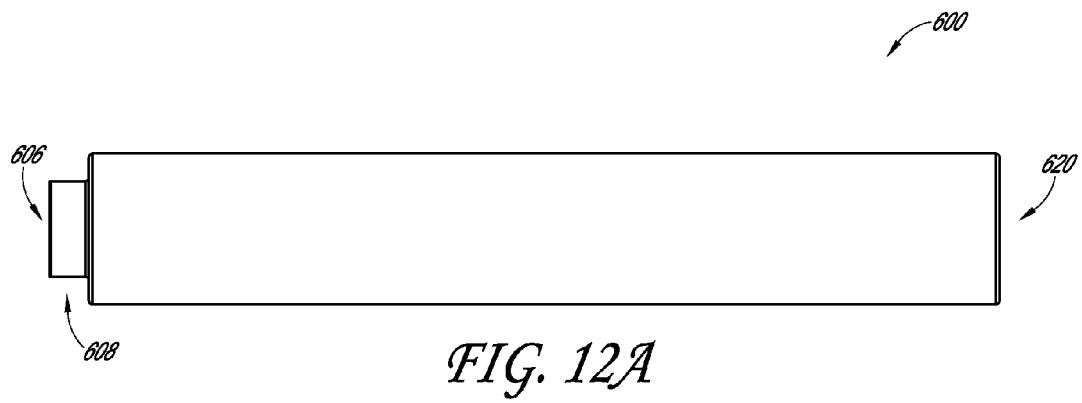
FIG. 12A
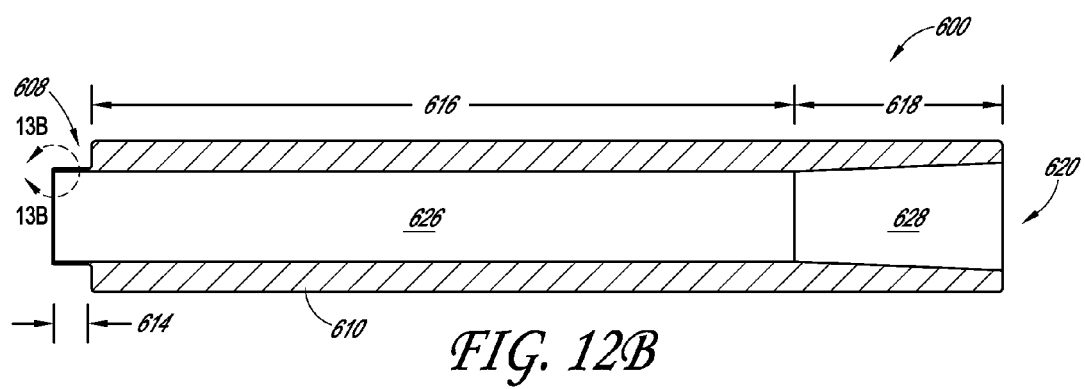
FIG. 12B
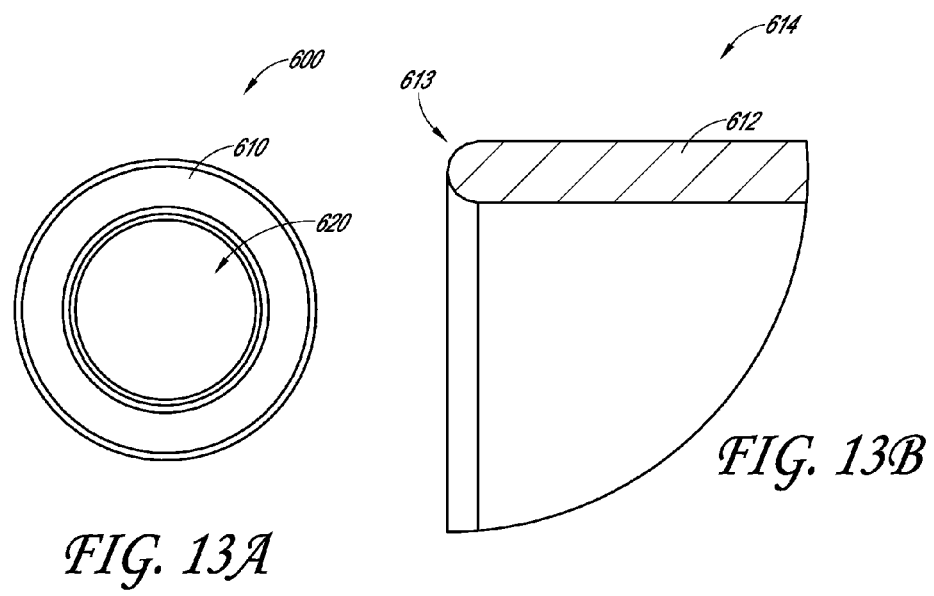
FIG. 13A
FIG. 13B

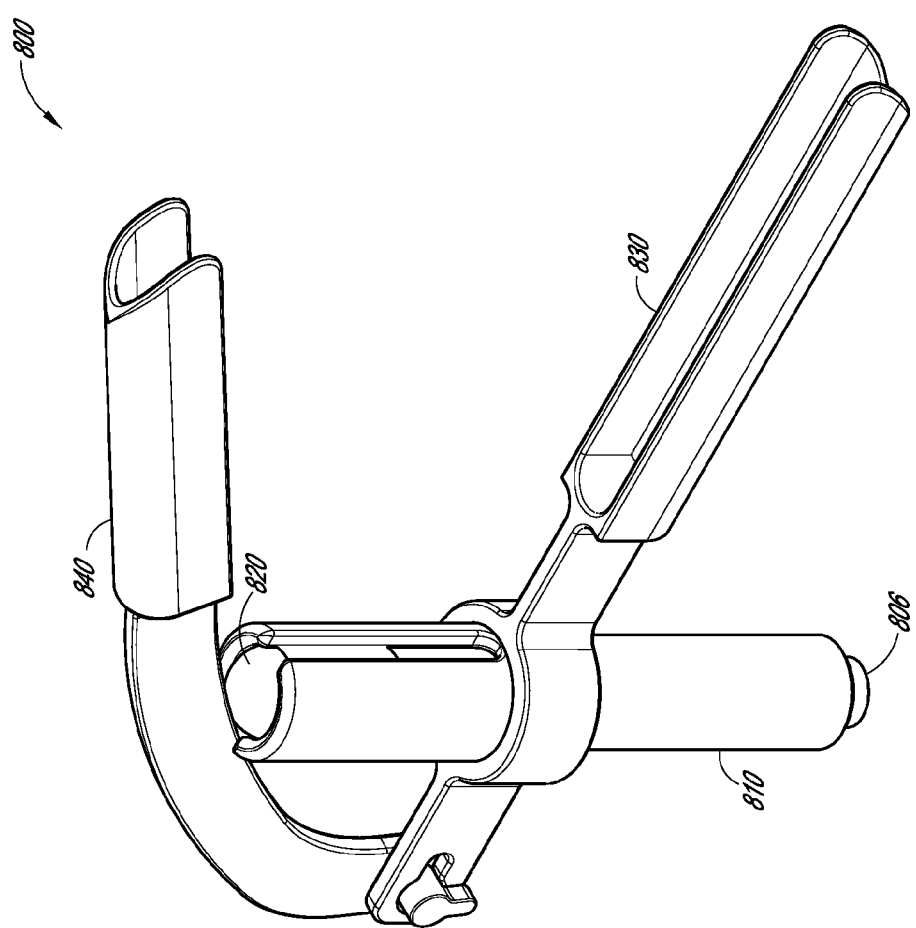

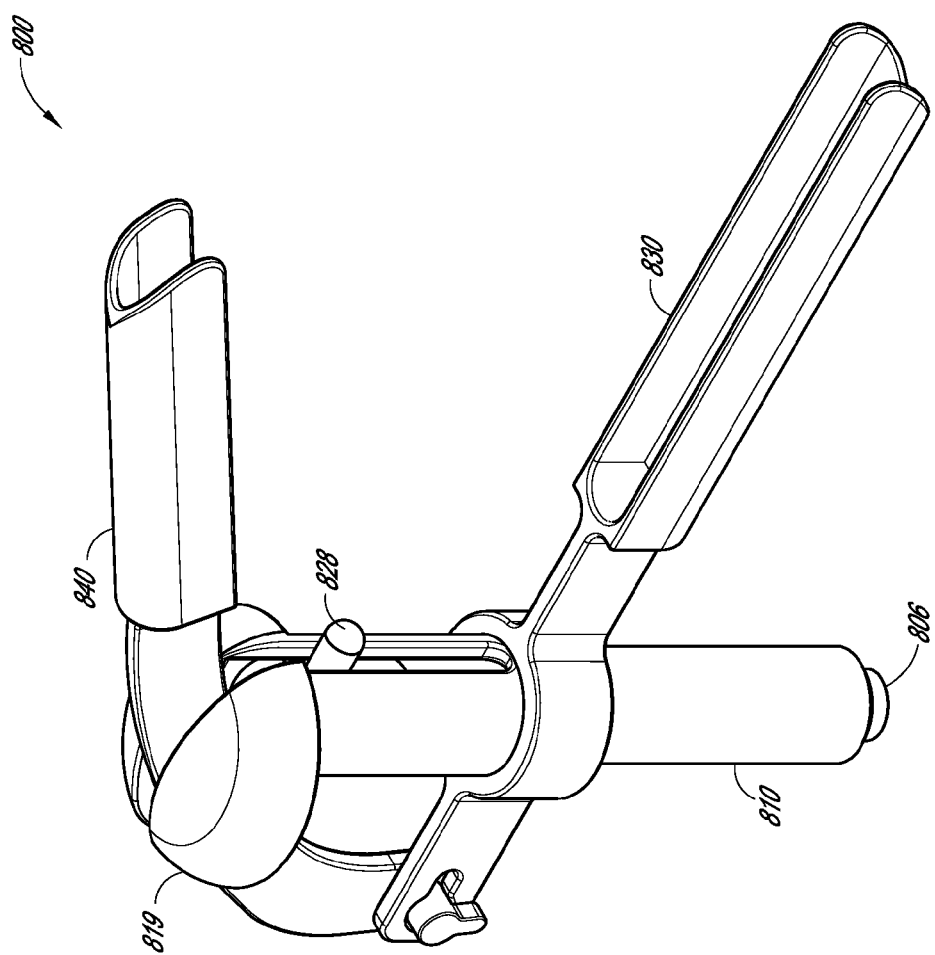

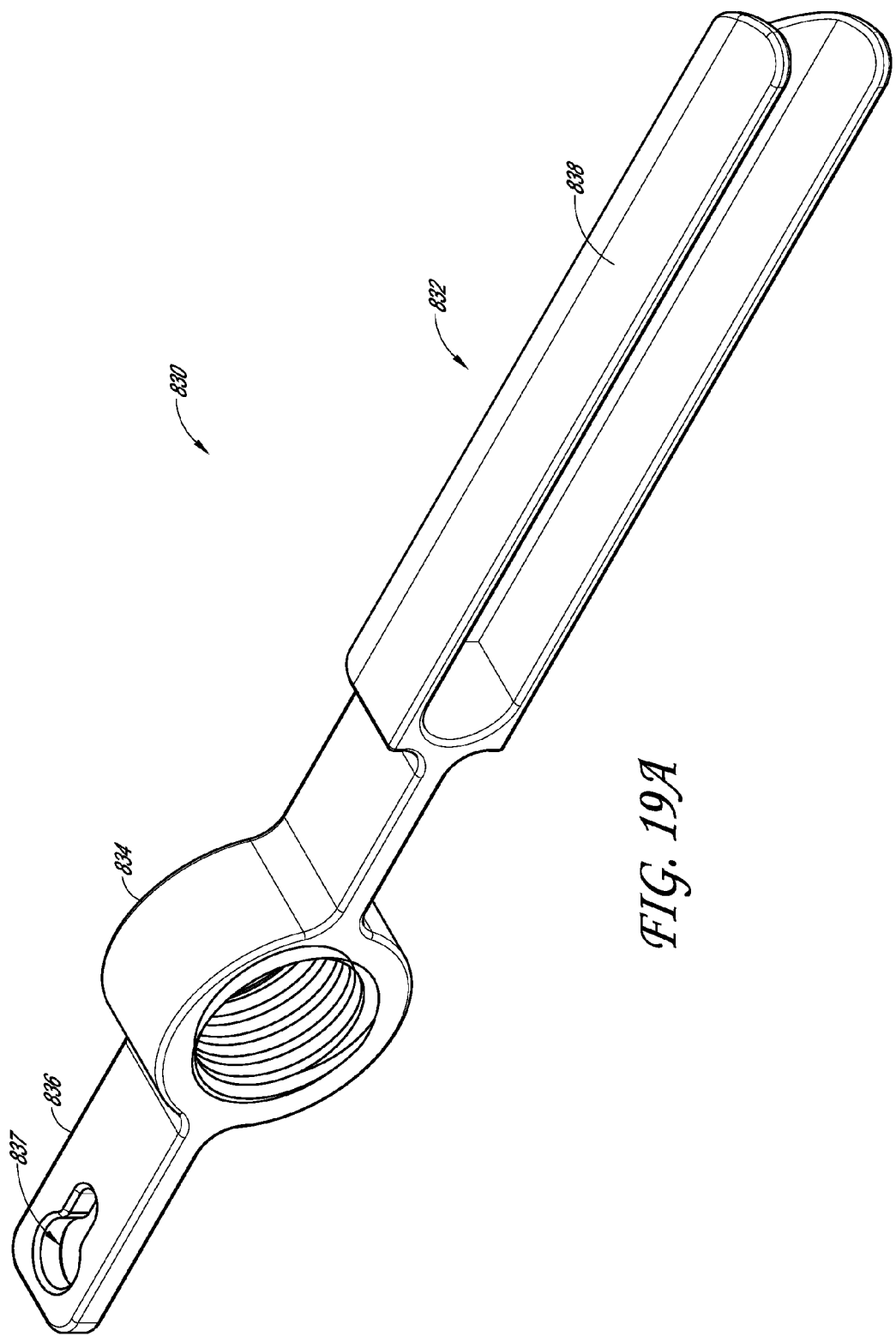

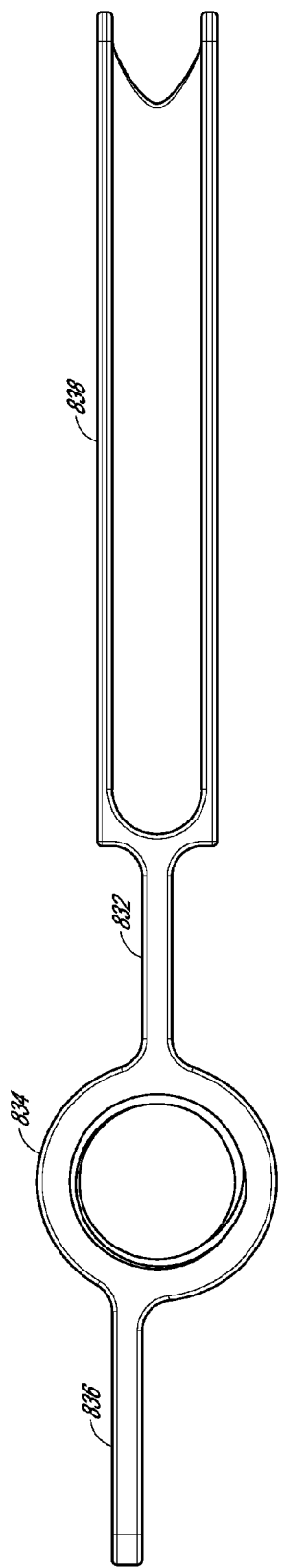

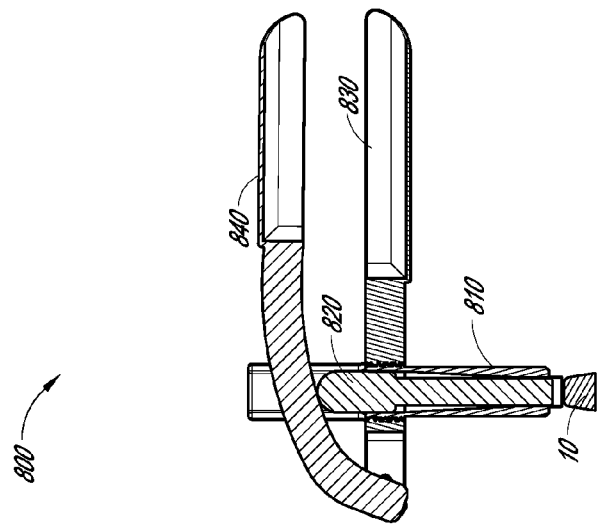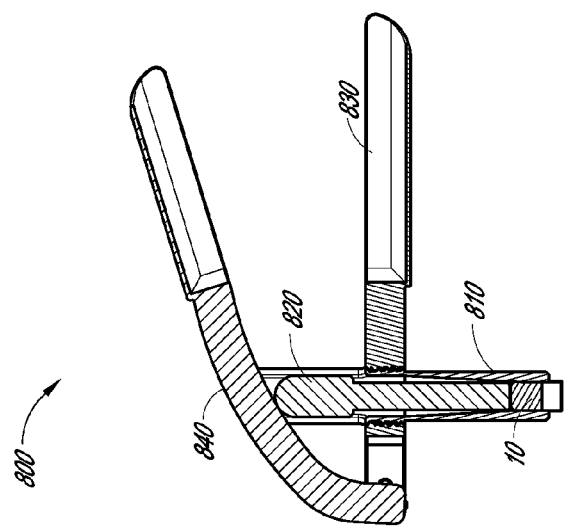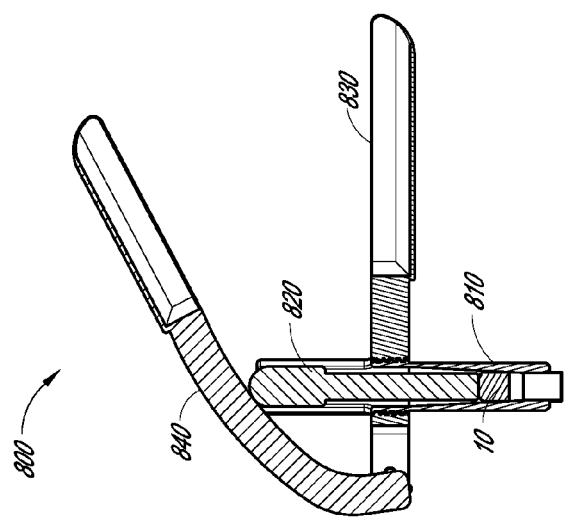

METHODS OF REPAIRING A JOINT USING A WEDGE-SHAPED IMPLANT

CROSS-REFERENCE TO RELATED APPLICATIONS

This application is a continuation application of U.S. patent application Ser. No. 13/480,272, filed May 24, 2012, which claims priority benefit of U.S. Provisional Application No. 61/490,507, filed May 26, 2011, the entireties of both of which are hereby incorporated by reference herein.

BACKGROUND

1. Field

This application relates generally to anatomical implants, and more specifically, to hydrogel joint implants and various tools, devices, systems and methods related thereto.

2. Description of the Related Art

Implants are often used to replace deteriorated or otherwise damaged cartilage within a joint. Such devices can be used to treat osteoarthritis, rheumatoid arthritis, other inflammatory diseases, generalized joint pain and/or other joint diseases. To ensure proper function and long term effectiveness, such implants should be properly secured within a patient's bone or other implant site.

SUMMARY

According to some embodiments, a method of treating a joint of a patient comprising creating a recess, hole or other opening in a bone located at or near a targeted joint, wherein the recess comprises a generally wedge, reverse tapered, truncated cone shape and/or other shape in which the bottom of the recess comprises a larger diameter or other cross-sectional dimension than a top of the recess. In some embodiments, the recess or other opening in the bone comprises a surface opening along an outer surface of the bone, a bottom opening along the distal end of the recess and side walls that generally extend between the surface opening and the bottom opening, wherein a diameter or other cross-sectional dimension of the bottom opening is larger than a diameter or other cross-sectional dimension of the surface opening.

According to some embodiments, the method further comprises at least partially radially compressing a joint implant having wedge or truncated cone shape, wherein the joint implant comprises a first end and a second end and a body extending between the first end and the second end. In some embodiments, the second end of the implant is generally opposite of the implant's first end. In one embodiment, when the joint implant is in a radially uncompressed state, a diameter or other cross-sectional dimension of the first end is smaller than a diameter or other cross-sectional dimension of the second end. The method further comprises inserting the joint implant within the recess, while the joint implant is in a radially compressed state, wherein the second end of the joint implant is inserted first within the recess. In some embodiments, the second end of the joint implant is adjacent the bottom opening of the recess, and the first end of the joint implant is adjacent the surface opening of the recess when the joint implant is properly positioned within the recess. The method further comprises, in some embodiments, releasing the joint implant from a radially compressed state to a less compressed state, when the joint implant is properly positioned within the recess, wherein, when the joint implant is in a less compressed state, the diameter or other cross-sectional dimension of the second end of the joint implant is larger than the diameter or other cross-sectional dimension of the surface opening of the recess. In some embodiments, when the joint implant is in a radially uncompressed state, the body of the joint implant imparts a radial force at least partially along the side walls of the recess, thereby securing the joint implant within the recess.

According to some embodiments, creating the recess in a bone comprises using a drill bit comprising an articulating cutter configured to selectively enlarge the recess near the bottom opening along the distal end of the recess. In some embodiments, creating the recess comprises moving a sleeve of the drill bit so as to radially expand the articulating cutter outwardly at or near the distal end of the recess. In one embodiment, the drill bit is cannulated, wherein the drill bit is positioned over a guide pin to place a working end of the drill bit near a targeted location of the recess.

According to some embodiments, the joint implant is radially compressed and inserted within the recess using an introducer. In some embodiments, the joint implant is urged through an interior of the introducer using a plunger or other pusher member. In some embodiments, the joint implant is urged through an interior of the introducer using a mechanically-assisted device. In some embodiments, the mechanically-assisted device comprises a handle and a clamp coupled to the handle, wherein moving the clamp relative to the handle urges a plunger within an introducer to radially compress the joint implant and insert the joint implant within the recess. In some embodiments, the clamp is rotatably coupled to the handle. In some embodiments, an interior of the introducer is polished to further reduce friction. In some embodiments, movement of the implant through an introducer is facilitated with the use of a vacuum source, a pressure source and/or any other pneumatic, mechanical, electrical and/or other device.

According to some embodiments, the joint implant comprises a hydrogel, such as, for example, polyvinyl alcohol (PVA), other polymeric materials and/or the like. In some embodiments, a content of PVA and/or any other polymeric component of the hydrogel is approximately 20% to 60% by weight (e.g., about 20, 25, 30, 35, 40, 45, 50, 55, 60%, values between the foregoing percentages, etc.). In some embodiments, a content of PVA and/or any other polymeric component of the hydrogel is less than approximately 20% or greater than approximately 60% by weight. In some embodiments, a ratio of the diameter or other cross-sectional dimension of the second end of the joint implant to the diameter or other cross-sectional dimension of the first end of the joint implant is approximately between approximately 1.05 and 1.3 (e.g., about 1.05, 1.1, 1.15, 1.2, 1.25, 1.3, ratios between the foregoing, etc.). In other embodiments, a ratio of the diameter or other cross-sectional dimension of the second end of the joint implant to the diameter or other cross-sectional dimension of the first end of the joint implant is less than approximately 1.05 or greater than approximately 1.3. In some embodiments, a ratio of the diameter or other cross-sectional dimension of the second end of the joint implant to the diameter or other cross-sectional dimension of the first end of the joint implant is at least about 1.1

According to some embodiments, the diameter or other cross-sectional dimension of the second end of the implant is approximately 5% to 25% larger (e.g., about 5, 10, 15, 20, 25%, values between the foregoing percentages, etc.) than the diameter or other cross-sectional dimension of the implant. In some embodiments, the diameter or other cross-sectional dimension of the second end of the implant is less than approximately 5% or greater than approximately 25% of the diameter or other cross-sectional dimension of the implant. In some embodiments, the recess is located within or near at least one of a toe, finger, ankle, knee, shoulder, hip or any other joint. In some embodiments, the top end of the joint implant is approximately 5 mm to 20 mm (e.g., about 5, 6, 7, 8, 9, 10, 11, 12, 13, 14, 15, 16, 17, 18, 19, 20 mm, values between the foregoing, etc.) in diameter or in other cross-sectional dimension. In some embodiments, the top end of the joint implant is greater than approximately 20 mm or smaller than approximately 5 mm (e.g., about 1, 1.5, 2, 2.5, 3, 3.5, 4, 4.5, 4.9 mm, ranges between the foregoing, less than about 1 mm, etc.).

According to some embodiments, an implant configured for implantation within a joint of a patient comprises a top end configured to form an articulation surface when properly implanted within a joint, a bottom end generally opposite of the top end and a main hydrogel body extending between the top end and the bottom end and having a longitudinal centerline. In some embodiments, such an implant comprises a hydrogel (e.g., PVA) implant or any other type of substrate-based implant. In some embodiments, such an implant can be used in any of the joint treatment methods disclosed herein. In some embodiments, a diameter or a cross-sectional dimension of the bottom end is greater than a diameter or a cross-sectional dimension of the top end. In one embodiment, side walls generally extend between the top end and the bottom end of the implant, wherein the side walls are generally sloped relative to the longitudinal centerline. In some embodiments, the implant comprises a tapered shape due to, at least in part, to a difference between the diameters or cross-sectional dimensions of the top end and the bottom end. In some embodiments, the implant is configured for placement within an implant site having a similar reverse tapered shape, thereby reducing the likelihood of unintentional removal of the implant from the implant site following implantation.

According to some embodiments, the hydrogel comprises polyvinyl alcohol (PVA) and/or any other polymeric material. In some embodiments, the content of PVA in the hydrogel is approximately 35% to 45% by weight (e.g., about 35, 36, 37, 38, 39, 40, 41, 42, 43, 44, 45%, values between the foregoing, etc.). In other embodiments, the content of PVA in the hydrogel is greater than approximately 45% by weight (e.g., about 45, 50, 55, 60, 65, 70%, greater than about 70%, ranges between the foregoing values, etc.) or less than approximately 35% by weight (e.g., 5, 10, 15, 20, 25, 30, 35%, ranges between the foregoing values, less than about 5%, etc.). According to one embodiment, the content of PVA or other component in the hydrogel is approximately 40% by weight. In some embodiments, the implant is load bearing and generally non-biodegradable. In some embodiments, the implant is configured for placement within at least one of a toe, finger, ankle, knee, shoulder, hip or any other joint. In some embodiments, a transition between the top end and the side walls is generally curved or otherwise smooth.

According to some embodiments, the top end of the implant is approximately 5 mm to 20 mm in diameter or other cross-section dimension (e.g., about 5, 10, 15, 20 mm, ranges between the foregoing values, etc.). In other embodiments, the top end of the implant is greater than about 20 mm (e.g., 25, 30, 35, 40 mm, greater than 40 mm, etc.) or smaller than about 5 mm (e.g., 1, 1.5, 2, 2.5, 3, 3.5, 4.5, 5 mm, ranges between the foregoing, less than about 1 mm, etc.). In some embodiments, a diameter of the bottom end is approximately 5% to 25% larger than a diameter of the top end (e.g., about 5, 6, 7, 8, 9, 10, 12, 14, 16, 18, 20, 25%, ranges between the foregoing, less than about 5%, greater than about 25%, etc.). In some embodiments, a diameter of the bottom end is approximately 10% to 15% larger than a diameter of the top end (e.g., about 10, 11, 12, 13, 14, 15%, ranges between the foregoing, less than about 10%, greater than about 15%, etc.).

According to some embodiments, a distance between the top end and the bottom end of the implant is approximately 4 mm to 16 mm (e.g., about 4, 5, 6, 7, 8, 9, 10, 11, 12, 13, 14, 15, 16 mm, values between the foregoing, etc.). In other embodiments, a distance between the top end and the bottom end of the implant is less than approximately 4 mm (e.g., less than 1 mm, about 1 mm, about 2 mm, about 3 mm, about 4 mm, ranges between the foregoing, etc.) or greater than approximately 16 mm (e.g., about 16, 17, 18, 19, 20, 22, 24, 26, 28, 30, 35, 40, 45, 50 mm, greater than about 50 mm, etc.). In some embodiments, a ratio of the diameter or other cross-sectional dimension of the bottom end of the implant to the diameter or other cross-sectional dimension of the top end of the implant is approximately between 1.05 and 1.3 (e.g., about 1, 1.05, 1.1, 1.15, 1.2, 1.25, 1.3, ranges between the foregoing, etc.). In some embodiments, a ratio of the diameter or other cross-sectional dimension of the bottom end of the implant to the diameter or other cross-sectional dimension of the top end of the implant is greater than about 1.3 (e.g., about 1.3, 1.35, 1.4, 1.45, 1.5, 1.6, 1.7, 1.8, 1.9, 2.0, greater than about 2.0, ranges between the foregoing, etc.). In some embodiments, a ratio of the diameter or other cross-sectional dimension of the bottom end of the implant to the diameter or other cross-sectional dimension of the top end of the implant is at least about 1.1.

According to some embodiments, a drill bit configured to be used with a bone drill to make a reverse taper recess within a bone along or near a joint of a patient comprises a main body comprising a proximal end and a distal end. Such a drill bit or other tool can be used in the method of treating a joint and/or prior to delivering a reverse tapered implant into the anatomy, in accordance with the disclosure provided herein. In some embodiments, the proximal end of the main body is configured to couple to a driving portion of a bone drill in order to selectively rotate said drill bit. In some embodiments, the drill bit or other tool comprises a flange located along the distal end of the main body and one or more (e.g., two, three, four, more than four) stationary cutters extending distally from the flange, wherein the one or more stationary cutters are configured to create a generally cylindrical opening within a bone. In some embodiments, the drill bit or other tool further comprises at least one articulating cutter extending distally from the flange, wherein the articulating cutter is configured to be selectively moved between a stowed position and a radially extended position, and wherein the articulating cutter is configured to create a reverse taper, wedge, truncated cone or similarly shaped recess within a bone when in the radially extended position, wherein a diameter or other cross-sectional dimension of a bottom opening of the recess is larger than a diameter or other cross-sectional dimension of a surface opening of the recess.

According to some embodiments, wherein the drill bit comprising at least one articulating cutter is inserted within a generally cylindrical recess created by a first bit, wherein a reverse taper or similarly shaped recess is created within the generally cylindrical recess when the at least one articulating cutter is moved (e.g., extended) to the radially extended position. According to some embodiments, the one or more articulating cutters of the drill bit are coupled to the main body using a hinge or other pivot point. In one embodiment, the articulating cutter is normally resiliently biased in the stowed position. In other embodiments, the articulating cutter is normally resiliently biased in the expanded or extended position. In some embodiments, the drill bit is cannulated or otherwise comprises one or more openings or passages, thereby allowing the drill bit to be placed over a guide pin in order to accurately position the drill bit to a targeted portion of a bone. In some embodiments, the drill bit comprises a sleeve, sheath and/or other outer member configured to be moved relative to the main body, wherein retracting the sleeve radially causes the at least one articulating cutter to be moved from the stowed position and the radially extended position.

According to some embodiments, a mechanically-assisted delivery tool for delivering an implant within a corresponding implant site comprises an introducer tube comprising an inner lumen and a neck portion along a distal end of said introducer tube, wherein the inner lumen of the introducer tube comprises a generally cylindrical portion along a proximal end of the introducer tube and a narrowed portion along the distal end. In some embodiments, the neck portion of the introducer tube is configured to be inserted within a recess or other opening created within an implant site of a patient. In one embodiment, the introducer tube comprises at least one slit or other recess or opening extending at least partially along a length of the introducer tube. In some embodiments, the mechanically-assisted delivery tool comprises a plunger or other movable member configured to be at least partially inserted into and moved within the lumen of the introducer tube. In some embodiments, the tool additionally comprises a handle coupled to the introducer tube, wherein the handle comprises at least one opening. In some embodiments, the tool comprises a clamp comprising a protruding member configured to be inserted within the at least one opening of the handle to couple the clamp to the handle.

According to some embodiments, the clamp is rotatably movable relative to the handle by movement of the protruding member within the at least one opening. In some embodiments, the clamp is configured to be selectively moved within the at least one slit or other opening of the introducer tube when the clamp is rotated relative to the handle. According to some embodiments, movement of the clamp within the at least one slit toward the distal end of the introducer tube urges the plunger positioned within the inner lumen of the introducer tube to move an implant placed within the lumen of the introducer tube to move within the narrowed portion of the inner lumen, through the neck portion of the introducer tube and within a target implant site. In some embodiments, movement of the implant within the narrowed portion of the inner lumen radially compresses the implant.

According to some embodiments, the introducer tube, the handle, the clamp and the plunger are configured to be selectively separated from one another to facilitate sterilization, cleaning, repairs, maintenance and/or any other activity relating to the delivery tool. In some embodiments, the introducer tube is coupled to the handle using a threaded connection, a snap-fit connection, a pressure or friction fit connection, a tab, other coupling and/or any other attachment device, system or method. In some embodiments, the narrowed portion of the inner lumen of the introducer tube comprises a generally linear slope. In some embodiments, the narrowed portion of the inner lumen of the introducer tube comprises a generally non-linear (e.g., curved, undulating, rounded, etc.) shape or slope. In some embodiments, the narrowed portion of the inner lumen extends from the generally cylindrical portion to the neck portion of the introducer tube. In some embodiments, a head portion of the plunger comprises a motion limiter to limit movement of the plunger within the inner lumen of the introducer tube to a maximum depth. In one embodiment, a proximal end of the introducer tube comprises a flange or other flared portion.

According to some embodiments, a method of treating a joint of a patient comprises creating a recess in a bone located at or near a targeted joint, wherein the recess comprises a generally wedge, truncated cone or reverse tapered shape. In some embodiments, the recess in a bone comprises a surface opening along an outer surface of the bone, a bottom opening along the distal end of the recess and side walls generally extending between the surface opening and the bottom opening, wherein a diameter or other cross-sectional dimension of the bottom opening is larger than a diameter or other cross-sectional dimension of the surface opening. In one embodiment, the method comprises at least partially radially compressing a joint implant having wedge or truncated cone shape, wherein the joint implant includes a first end and a second end and body extending between the first end and the second end such that the second end is generally opposite of the first end. In some embodiments, when the joint implant is in a radially uncompressed state, a diameter or other cross-sectional dimension of the first end is smaller than a diameter or other cross-sectional dimension of the second end. In some embodiments, while the joint implant is in a radially compressed state, the method additionally comprises inserting the joint implant within the recess, wherein the second end of the joint implant is inserted first within the recess. In one embodiment, the second end of the joint implant is adjacent the bottom opening of the recess, and wherein the first end of the joint implant is adjacent the surface opening of the recess when the joint implant is properly positioned within the recess. In one embodiment, the method comprises releasing the joint implant from a radially compressed state to a less compressed state, when the joint implant is properly positioned within the recess. In one embodiment, when the joint implant is in a less compressed state, the diameter or other cross-sectional dimension of the second end of the joint implant is larger than the diameter or other cross-sectional dimension of the surface opening of the recess. In some embodiments, when the joint implant is in a radially uncompressed state, the body of the joint implant imparts a radial force at least partially along the side walls of the recess, thereby securing the joint implant within the recess.

According to some embodiments, creating the recess in a bone comprises using a drill bit comprising an articulating cutter configured to selectively enlarge the recess near the bottom opening along the distal end of the recess. In one embodiment, creating the recess comprises moving a sleeve of the drill bit so as to radially expand the articulating cutter outwardly at or near the distal end of the recess. In some embodiments, the drill bit is cannulated. In one embodiment, the drill bit is positioned over a guide pin or other guide or positioning member to place a working end of the drill bit at or near a targeted location of the recess. In some embodiments, the joint implant is radially compressed and inserted within the recess using an introducer. In some embodiments, the joint implant is urged through an interior of the introducer using a plunger or other pusher member. In one embodiment, the joint implant comprises a hydrogel. In some embodiments, the hydrogel comprises polyvinyl alcohol (PVA). In one embodiment, a content of PVA and/or other component of the hydrogel is approximately 20% to 60% by weight. In some embodiments, the water content of the hydrogel is approximately 40% to 80% by weight.

According to some embodiments, a ratio of the diameter or other cross-sectional dimension of the second end of the joint implant to the diameter or other cross-sectional dimension of the first end of the joint implant is approximately between 1.05 and 1.3. In some embodiments, a ratio of the diameter or other cross-sectional dimension of the second end of the joint implant to the diameter or other cross-sectional dimension of the first end of the joint implant is at least about 1.1. In one embodiment, the diameter or other cross-sectional dimension of the second end of the implant is approximately 5% to 25% larger than the diameter or other cross-sectional dimension of the implant. In some embodiments, the recess is located within or near at least one of a toe, finger, ankle, knee, shoulder, hip or other joint. In some embodiments, the top end of the joint implant is approximately 5 mm to 20 mm in diameter.

According to some embodiments, a drill bit configured to be used with a bone drill to make a reverse taper or wedge recess within a bone along or near a joint of a patient comprises a main body comprising a proximal end and a distal end, such that the proximal end of the main body is configured to couple to a driving portion of a bone drill in order to selectively rotate said drill bit. According to one embodiment, the drill bit further comprises a flange located along the distal end of the main body. In some embodiments, the drill bit comprises one or more stationary cutters extending distally from the flange, wherein the stationary cutters are configured to create a generally cylindrical opening within a bone. The drill bit further comprises at least one articulating cutter extending distally from the flange, wherein the articulating cutter is configured to be selectively moved between a stowed position and a radially extended position. In one embodiment, the articulating cutter is configured to create a reverse taper or wedge shaped recess within a bone when in the radially extended position, wherein a diameter of a bottom opening of the recess is larger than a diameter of a surface opening of the recess.

According to some embodiments, the drill bit comprising an articulating cutter is inserted within a generally cylindrical recess created by a first bit, such that a reverse taper recess or wedge shape is created within the generally cylindrical recess when the articulating cutter is moved to the radially extended position. In some embodiments, the articulating cutter is coupled to the main body using a hinge or other pivot point. In one embodiment, the at least one articulating cutter is normally resiliently biased in the stowed position. In some embodiments, the drill bit is cannulated, allowing the drill bit to be placed over a guide pin or other positioning member in order to accurately position the drill bit to or near a targeted portion of a bone (e.g., joint). In one embodiment, the drill bit further comprises a sleeve or other movable member configured to be slid or otherwise moved relative to the main body, wherein retracting the sleeve or other member radially causes the articulating cutter to be moved from the stowed position and the radially extended position.

According to some embodiments, a hydrogel implant configured for implantation within a joint of a patient comprises a top end configured to form an articulation surface when properly implanted within a joint, a bottom end generally opposite of the top end and a main hydrogel body extending between the top end and the bottom end and having a longitudinal centerline. In some embodiments, a diameter of the bottom end is greater than a diameter of the top end and side walls generally extend between the top end and the bottom end, such that the side walls are generally sloped relative to the longitudinal centerline. In one embodiment, the implant comprises a tapered shape due to, at least in part, to a difference between the diameters of the top end and the bottom end. In some embodiments, the implant is configured for placement within an implant site having a similar reverse tapered or wedge shape, thereby reducing the likelihood of unintentional removal of the implant from the implant site following implantation.

According to some embodiments, the hydrogel comprises polyvinyl alcohol (PVA) and/or another substance or additive. In some embodiments, the content of PVA and/or other substances is approximately 10% to 80% (e.g., about 35% to 45%) by weight. In some embodiments, the content of PVA is approximately 40% by weight. In one embodiment, the content of water and/or saline in the hydrogel is 60% by weight. In one embodiment, the implant is load bearing and generally non-biodegradable. In some embodiments, the implant is configured for placement within at least one of a toe, finger, ankle, knee, shoulder, hip or other joint. In some embodiments, a transition between the top end and the side walls is generally curved or otherwise smooth. In one embodiment, the top end of the implant is approximately 5 mm to 20 mm in diameter. In some embodiments, a diameter of the bottom end is approximately 5% to 25% larger than a diameter of the top end. In one embodiment, a diameter of the bottom end is approximately 10% to 15% larger than a diameter of the top end. In some embodiments, a distance between the top end and the bottom end of the implant is approximately 4 mm to 16 mm. In one embodiment, a ratio of the diameter or other cross-sectional dimension of the bottom end of the implant to the diameter or other cross-sectional dimension of the top end of the implant is approximately between 1.05 and 1.3. In one embodiment, a ratio of the diameter or other cross-sectional dimension of the bottom end of the implant to the diameter or other cross-sectional dimension of the top end of the implant is at least 1.1.

According to some embodiments, a hydrogel implant configured for implantation within a joint of a patient comprises a top end configured to form an articulation surface when properly implanted within a joint, a bottom end generally opposite of the top end and a main hydrogel body extending between the top end and the bottom end and having a longitudinal centerline. In one embodiment, a diameter of the bottom end is greater than a diameter of the top end. The implant additionally comprises side walls that generally extend between the top end and the bottom end, wherein the side walls are generally sloped relative to the longitudinal centerline of the implant. In some embodiments, the implant comprises a tapered shape or frustum due to, at least in part, to a difference between the diameters of the top end and the bottom end. In one embodiment, the implant is configured for placement within an implant site having a similar reverse tapered, wedge or truncated cone shape or frustum, thereby reducing the likelihood of unintentional removal of the implant from the implant site following implantation.

According to some embodiments, the hydrogel comprises polyvinyl alcohol (PVA), saline, water, another hydrogel material, another polymeric material and/or any other substance or additive. In some embodiments, the content of PVA in the implant is approximately 20% to 60% by weight. In one embodiment, the content of PVA in the implant is approximately 40% by weight. In some embodiments, the implant is generally load bearing and/or configured for long term implantation within a patient. In one embodiment, the implant is generally non-biodegradable.

According to some embodiments, the joint implant is configured for placement within a toe, finger, ankle, knee, shoulder, hip and/or any other joint. In one embodiment, a transition between the top end and the side walls is generally curved or otherwise smooth. In some embodiments, the top end of the implant is approximately 5 mm to 20 mm in diameter. In some embodiments, a diameter of the bottom end is approximately 5% to 15% (e.g., about 10%, 11%, 12%, 13%, 14%, 15%, etc.) larger than a diameter of the top end of the implant. In some embodiments, a distance between the top end and the bottom end of the implant is approximately 4 mm to 16 mm.

According to some embodiments, a method of treating a joint of a patient comprises creating a recess in a bone located at or near a targeted joint, wherein the recess includes a generally wedge or truncated cone shape. In one embodiment, the recess in a bone comprises a surface opening along an outer surface of the bone and a bottom opening along the distal end of the recess, such that a diameter of the surface opening is generally smaller than a diameter of the bottom opening. The method additionally comprises providing a joint implant having a wedge or truncated cone shape, wherein a diameter of a top end of the joint implant is generally smaller than a diameter of a bottom end of the joint implant. The method further includes inserting the joint implant within the recess so that the bottom end of the joint implant is adjacent to the bottom opening of the recess. In some embodiments, the diameter of the bottom end of the joint implant is larger than the diameter of the surface opening of the recess. In some embodiments, the size of the implant matches or substantially matches the size of the recess. In some embodiments, the size of the implant is larger (e.g., nominally, significantly, etc.) than the size of the recess. Accordingly, in such arrangements, the implant remains at least partially radially compressed within after implantation into the target recess or other implant site. The amount of radial compression in the implant after implantation into the recess can vary from approximately 0% to about 20% (e.g., about 1%, 2%, 3%, 4%, 5%, 10%, 15%, 20%, values between the foregoing percentages, etc.). In one embodiment, for example, the compression ratio of an implant is approximately 10%, wherein the diameter (or other cross sectional dimension) of the recess base is about 90% of the base or bottom diameter of the implant.

According to some embodiments, the step of creating a recess in a bone comprises using a drill bit comprising an articulating cutter configured to create the generally wedge or truncated cone shape in the recess. In one embodiment, the joint implant is inserted within the recess using an introducer. In some embodiments, the joint implant is urged through an interior of the introducer using a plunger or other pusher member (e.g., manually or with the assistance of mechanical, hydraulic, pneumatic or other externally driven device). In some embodiments, the implant comprises a hydrogel (e.g., PVA). In some embodiments, the recess is located within a toe, finger, ankle, knee, shoulder, hip or any other joint.

BRIEF DESCRIPTION OF THE DRAWINGS

These and other features, aspects and advantages of the present application are described with reference to drawings of certain embodiments, which are intended to illustrate, but not to limit, the various inventions disclosed herein. It is to be understood that the attached drawings are for the purpose of illustrating concepts and embodiments of the present application and may not be to scale.

FIG. 12A illustrates a side view of the introducer of FIG. 11;

FIG. 12B illustrates a longitudinal cross-sectional view of the introducer of FIG. 11;

FIG. 13A illustrates a distal end view of the introducer of FIG. 11;

FIG. 13B illustrates a detailed view along the neck portion of the introducer depicted in FIG. 11;

FIG. 16A illustrates a perspective view of an assembled implant delivery tool according to one embodiment;

FIG. 16D illustrates a perspective view of an assembled implant delivery tool according to one embodiment;

FIG. 19A illustrates a perspective view of a handle;

FIG. 19B illustrates a top view of the handle of FIG. 19A;

FIGS. 21A-21C illustrate sequential views of an implant being moved through and deployed from a delivery tool.

DETAILED DESCRIPTION

The discussion and the figures illustrated and referenced herein describe various embodiments of a cartilage implant, as well as various tools, systems and methods related thereto. A number of these devices and associated treatment methods are particularly well suited to replace deteriorated or otherwise damaged cartilage within a joint. Such implants are configured to remain within the patient's joint on a long-term basis (e.g., for most or all of the life of the patient), and as such, are configured, in some embodiments, to replace native cartilage. Thus, in some embodiments, the implants are configured to be substantially non-biodegradable and/or non-erodable. In some embodiments, for example, an implant is configured to remain within the patient's joint or other portion of the anatomy for a minimum of 20 to 100 years (e.g., about 20, 25, 30, 35, 40, 45, 50, 55, 60, 65, 70, 75, 80, 85, 90, 95, 100 years, durations between the foregoing values, etc.) without losing its structural and/or physical properties and/or without losing its ability to function as a cartilage replacement component or device. In other embodiments, the implants are configured to remain within the anatomy for greater than 100 years without losing its structural and/or physical properties and/or without losing its ability to function as a cartilage replacement component. Accordingly, such embodiments can be used to treat osteoarthritis, rheumatoid arthritis, other inflammatory diseases, generalized joint pain and/or other joint diseases. However, the various devices, systems, methods and other features of the embodiments disclosed herein may be utilized or applied to other types of apparatuses, systems, procedures and/or methods, including arrangements that have non-medical benefits or applications.

Figure 1:
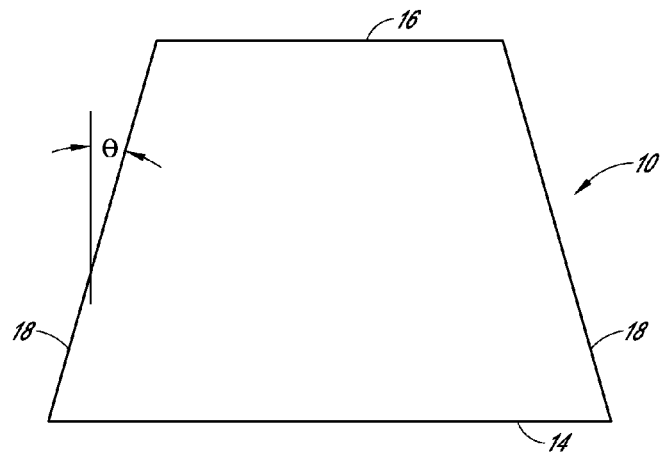
FIG. 1 schematically illustrates a side view of a tapered implant according to one embodiment.

FIG. 1 schematically illustrates one embodiment of an implant 10 intended for placement within or near a joint of a patient (e.g., toe, finger, ankle, knee, hip, shoulder, etc.). As shown, the implant 10 can include a generally tapered overall shape, wherein its base surface 14 is larger than the opposite, top surface 16. As discussed in greater detail below, the smaller, top surface 16 can comprise the articulation surface (e.g., a surface that is at least partially exposed to a joint), whereas the larger bottom or base surface 14 is securely retained within a corresponding opening specially created in the anatomy (e.g., through bone, cartilage, other native tissue, etc.). As a result of such a design, the sides 18 of the implant 10 can comprise a taper angle θ (e.g., relative to generally vertical sides), thereby giving the implant a generally truncated cone or frustum-like shape. As discussed in greater detail herein, such a reverse-taper, wedge or truncated cone shape can help ensure proper securement of the implant 10 within a patient's anatomy.

Figure 2:
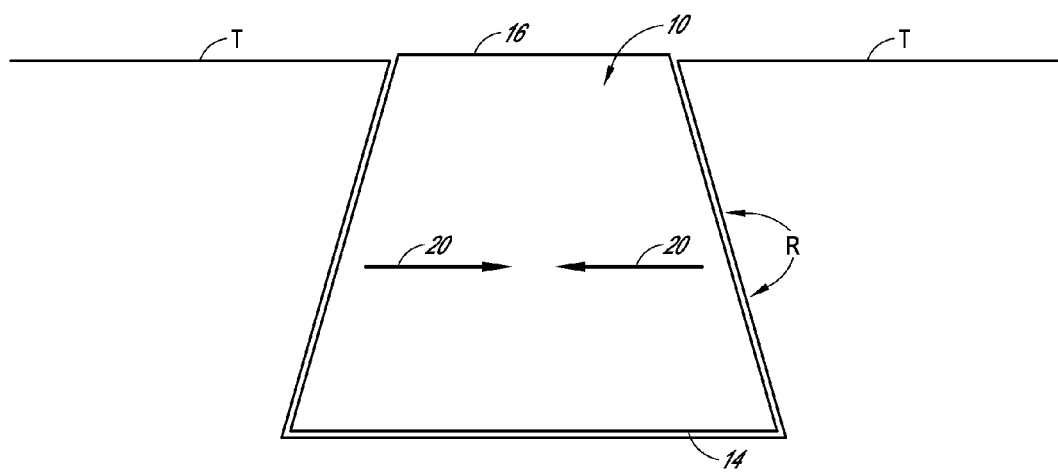
FIG. 2 schematically illustrates a side view of the implant of FIG. 1 positioned within a corresponding implant site, according to one embodiment.

FIG. 2 schematically illustrates an implant 10 similar to the one depicted in FIG. 1 snugly positioned within a corresponding recessed area R of a patient's tissue T (e.g., bone, cartilage, etc.). In some embodiments, such a recessed area R is formed at or near the patient's joint so that the implant 10 can be used to replace and/or augment damaged cartilage (e.g., on a long-term or permanent basis, as discussed above). Alternatively, however, the implant 10 can be positioned generally away from a joint or other articulation surface. Thus, any of the implant embodiments disclosed herein, or equivalents thereof, can be used in a human or animal anatomy for a variety of different indications or other purposes, such as, for example, joint therapy, reconstructive surgery, tissue augmentation, cosmetic surgery and/or the like. For any of the embodiments disclosed herein, or equivalents thereof, the implant 10 can be load bearing or non-load bearing, as desired or required. In some embodiments, once implanted within the anatomy, the implant 10 is configured to be non-biodegradable for at least the expected useful life of the implant 10. In some embodiments, the implant 10 is adapted to generally retain its general structure, shape, structure, size, strength, compressibility, function and/or other properties during the life of the patient into which the implant is inserted. For example, the implant 10 can be configured to generally maintain its original physical, chemical, biocompatibility and/or characteristics for at least about 100 years. In some embodiments, the implant retains the same or substantially the same water content, resiliency, durability, strength, coefficient of friction and/or any other properties for the period of time that it is positioned within the anatomy of the patient. In other embodiments, the implant 10 is configured to generally maintain its original physical, chemical, biocompatibility and/or characteristics for less or more than about 100 years (e.g., about 50 years, 60 years, 70 years, 80 years, 90 years, 110 years, 120 years, 130 years, 150 years, 200 years, more than about 200 years, less than about 50 years, etc.), as desired or required. In some embodiments, the implant 10 is configured to resist or substantially resist biodegradation or mass reduction during such target time period.

With continued reference to FIG. 2, during delivery of the implant 10 within the recess, the implant 10 can be compressed inwardly (e.g., as schematically depicted by the arrows 20). At least some methods of delivering such implants within an appropriately sized and shaped recess are discussed in greater detail herein. In some embodiments, once the implant 10 has been properly positioned within the recess R, the implant 10 is permitted to expand outwardly, thereby filling in or otherwise encompassing all or substantially all of the volume of the recess R. In some embodiments, the diameter or other cross-sectional dimension of the base 14 of the implant 10 is greater than the corresponding diameter or other cross-sectional dimension of the recess R. This helps prevent the implant 10 from moving out of the recess after implantation. The reverse tapered shape of the implant 10 and the recess R into which it is placed can help ensure that implant 10 remains securely within the recess R following implantation. In some embodiments, the outwardly directed forces of the implant 10 in the direction of the adjacent interior surfaces of the recess R assist in maintaining the implant 10 within the recess R during use (e.g., after implantation).

According to some embodiments, the base (or bottom) 14 and/or the top 16 of the implant 10 is generally circular. Alternatively, the shape of the ends 14, 16 can be different than circular, such as, for example, oval, square, other rectangular, other polygonal, irregular and/or the like. Further, once securely implanted in a patient's anatomy (e.g., within a recess R), the top 16 of the implant 10 can be generally flush with the adjacent tissue surface. However, in other embodiments, the top 16 of the implant 10 extends above the adjacent tissue T (e.g., as illustrated in FIG. 2) or below the adjacent tissue T following implantation. For example, in one embodiment, the top 16 of the implant is slightly "proud" or raised relative to the adjacent tissue (e.g., cartilage) in order to reestablish a desired contour of the damaged joint surface. In some embodiments, such a raised or otherwise protruding configuration can assist in creating a smoother transition between the exposed surface of the implant 10 and adjacent native cartilaginous surfaces of a joint.

The top and/or bottom surfaces 16, 14 of the implant 10 can be generally flat or planar. In other embodiments, the surface 16, 14 can be non-planar (e.g., curved, domed, convex, concave, fluted, ridged, etc.), as desired or required. The shape of the top and/or bottom surfaces can be selected based on a patient's anatomy, the location within the patient's anatomy in which the implant will be placed and/or one or more other factors or considerations. For example, the implant can be configured to generally or specifically match the slopes, contours and/or other features of the patient's existing cartilaginous and/or bone tissue, the recess and/or the like. Accordingly, the function of a rehabilitated joint or other targeted anatomical region being treated can be improved.

Figure 3A:
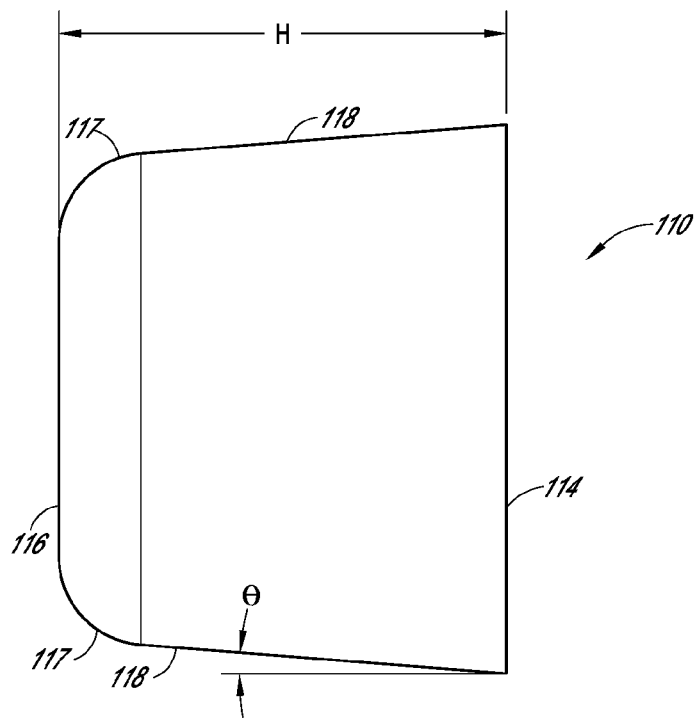
FIG. 3A illustrates a side view of a tapered implant according to one embodiment.
Figure 3B:
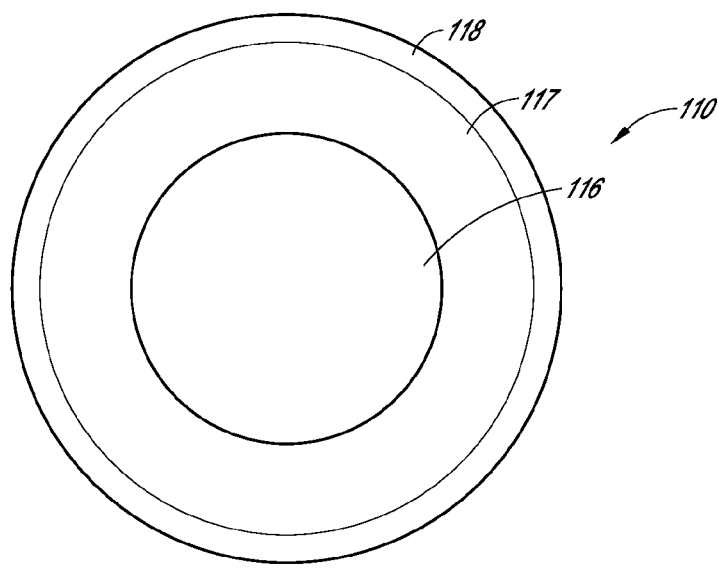
FIG. 3B illustrates a top view of the tapered implant of FIG. 3A.

Another embodiment of a tapered implant 110 configured to replace or augment damaged cartilage within a patient is illustrated in FIGS. 3A and 3B. As shown, the implant 110 can comprise a bottom or base surface 114 and a top surface 116, which is at least partially exposed to adjacent anatomical tissues (e.g., other cartilaginous surfaces, bone, other portions that function as an articulating surface of a joint, etc.) after implantation. As with the implant of FIGS. 1 and 2, the depicted embodiment includes a base 114 that is generally wider or otherwise larger than the top surface 116. For example, the diameter or other comparable cross-sectional dimension of the base can be larger than that of the top. Accordingly, the implant 110 can include generally sloped sides 118 that terminate in a top surface 116 of small diameter (or other cross sectional dimension) than that of the base or bottom surface 114. The sloped surfaces can be generally flat or curved, as desired or required. Further, as shown in FIG. 3A, the transition between the sides 118 and the top 116 can be rounded or otherwise smooth. However, the transition from the side surfaces 118 to the top 116 of the implant 110 can be more or less smooth than illustrated in FIG. 3A. In other words, in some embodiments, the radius of the curved corners is larger or smaller than disclosed herein. For example, as schematically illustrated in FIG. 1, an implant can comprise generally sharp transitions between the top surface and the sides.

As discussed herein with reference to FIGS. 1 and 2, the top, bottom and/or side surfaces of the implant 110 can be generally planar (e.g., flat) or non-planar (e.g., curved, concave, convex, undulating, fluted, etc.), as desired or required. Further, although not illustrated in FIG. 3A, the recess or other opening in which the implant 110 will be positioned can include a similar reverse-tapered shape (e.g., having a wider or large base and a smaller top) to help ensure that the implant 110 remains securely in place following implantation. Additional details regarding reverse tapered openings within a patient's anatomy (e.g., bone), including details related to tools and methods that help create such openings, are provided below.

With continued reference to FIGS. 3A and 3B, an implant 110 can include a generally circular or oval cross-sectional shape. Thus, in some embodiments, the implant 110 is generally shaped like a frustum, truncated cone, cylinder and/or the like. However, the overall shape of any of the implants disclosed herein can vary depending on the specific application or use. For example, the shape of the base (or bottom), top and/or any other cross-sectional area of an implant can be generally rectangular (e.g., square), other polygonal, irregular and/or the like.

Regardless of its exact size and shape, the base portion can be larger or wider than the top of the implant in order to help ensure that the implant remains securely positioned within a targeted portion of a patient's anatomy (e.g., a joint) following implantation. For example, in some embodiments, the dimension (or area) of the base or bottom of the implant is approximately 10% to 15% (e.g., about 10%, 11%, 12%, 13%, 14%, 15%, ranges between such values, etc.) longer, wider or otherwise larger than the top of the implant. Thus, in embodiments having generally circular bottom and top surfaces, such as, for example, the implant 110 illustrated in FIGS. 3A and 3B, the diameter of the base or bottom 114 is approximately 10% to 15% (e.g., about 10%, 11%, 12%, 13%, 14%, 15%, ranges between such values, etc.) larger than the diameter of the top 116. In other embodiments, the base 114 can be more than about 15% larger or less than about 10% larger than the top 116, as desired or required. For example, in some embodiments, the diameter (or other cross-sectional dimension) of the base 114 is larger than the diameter (or other cross-sectional diameter) of the top 116 by approximately 1%, 2%, 3%, 4%, 5%, 6%, 7%, 8%, 9%, less than 1%, other values between the foregoing percentages and/or the like. Alternatively, the diameter (or other cross-sectional dimension) of the base 114 is larger than the diameter (or other cross-sectional diameter) of the top 116 by approximately 16%, 17%, 18%, 19%, 20%, 25%, 30%, 35%, 40%, 50%, 60%, more than 60% and/or the like. According to some embodiments, for any of the implant arrangements disclosed herein, the ratio of the diameter (or other cross-sectional dimension) of the base 114 to the diameter (or other cross-sectional dimension) of the top 116 of the implant is between about 1 and about 1.3 (e.g., approximately or more than 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, values between the foregoing ratios, etc.). In other embodiments, the ratio is between about 1 and 1.05 (e.g., approximately or greater than 1.01, 1.02, 1.03, 1.04, 1.05), or greater than about 1.3 (e.g., approximately or more than 1.3, 1.35, 1.4, 1.45, 1.5, 1.55, 1.6, greater than 1.6, etc.), as desired or required.

As discussed above with reference to the embodiments illustrated in FIGS. 1-3B, an implant having a wedge or reverse tapered design (e.g., an implant having a larger base than top) can help prevent or reduce the likelihood of unintended ejection or other escape from the implant site after implantation. Thus, in some embodiments, the push-out force (e.g., the force necessary to eject or otherwise remove the implant from the implant site) is advantageously increased for wedge shaped implants relative to implants that do not include a wedge or reverse taper design (e.g., cylindrical implants, right angle implants, implants having generally vertical sides, etc.). As a result, the likelihood of maintaining such embodiments within a joint or other part of the anatomy after implantation is advantageously increased.

With continued reference to FIG. 2, the implant can be positioned within a recess or other opening formed within the patient's bone, cartilage or other tissue. As shown, in some embodiments, the implant 10 is sized, shaped and otherwise configured to fill all or most of the volume of the recess R once properly inserted therein. Further, according to some embodiments, the implant is radially oversized relative to the corresponding implant site (e.g., recess, opening, etc.) into which it will be placed. For example, an implant can be radially oversized by approximately 5% to 15% (e.g., about 5%, 6%, 7%, 8%, 9%, 10%, 11%, 12%, 13%, 14%, 15%, other percentages between such values, etc.) relative to the implant site. In alternative embodiments, an implant can be radially oversized by less than about 5% or more than about 15%, as desired or required. In such oversized embodiments, once implanted, the implant can exert a radial or other outwardly directed force on the corresponding recess. In some embodiments, such a configuration can help ensure that the implant remains securely within the recess after implantation. In yet other embodiments, the implant comprises a similar or identical size as the implant site or is generally radially undersized relative to the implant site.

As a result of the shape of the implant and the corresponding implant site (e.g., recess, other opening, etc.), it may be necessary to radially compress the implant (e.g., inwardly, as schematically illustrated by the arrows 20 in FIG. 2) in order to insert the implant within the implant site. Accordingly, one or more introducers or other delivery tools can be used to facilitate the placement of a tapered implant within an implant site. Additional inwardly-directed compressive forces on the tapered implant may be required for implants that are radially oversized relative to the target implant site, as discussed above. The degree to which an implant can be compressed (e.g., circumferentially, radially inwardly, etc.) may depend on one or more factors, properties, characteristics and/or other considerations, such as, for example, implant size, water content, ingredients and other components, strength, elasticity, surrounding temperature, method of manufacturing and/or the like.

According to some embodiments, radial compression of an implant can affect the implant's overall height, the shape or contours of its outer surfaces (e.g., top or articulating surface, base or bottom surface, sides, etc.) and/or one or more other properties or characteristics of the implant. By way of example, in some embodiments, radial compression of an implant causes the height of the implant to increase (e.g., relative to the height of the implant when it is not radially compressed). Consequently, careful consideration may need to be given to the design of the implant based on, among other things, the expected level of radial compression that may occur once the implant has been properly secured within the implant site. Therefore, the amount of radial compression, and thus its effect on the implant's diameter, height, other dimensions, shape and/or other properties, may need to be carefully determined prior to implantation. Otherwise, upon implantation, an implant may not properly align with adjacent cartilage or other tissue surfaces in a joint or other anatomical location.

According to some embodiments, any of the implant embodiments disclosed herein comprise polyvinyl alcohol (PVA) hydrogels. The implants can comprise one or more other materials, either in addition to or in lieu of PVA, such as, for example, other hydrogels, other polymeric materials, other additives and/or the like. In some embodiments, the PVA content of a hydrogel is approximately 40% by weight. However, the PVA content of an implant can be less or more than about 40% by weight (e.g., approximately 10%, 15%, 20%, 25%, 30%, 32%, 34%, 36%, 37%, 38%, 39%, 41%, 42%, 43%, 44%, 46%, 48%, 50%, 55%, 60%, 65%, 70% by weight, less than about 10% by weight, more than about 70% weight, values between the foregoing ranges, etc.), as desired or required.

Further, the implants can comprise water, saline, other liquids, combinations thereof and/or the like. In some embodiments, the use of saline within a hydrogel implant may be preferred over water, because, under certain circumstances, saline can help maintain osmotic balance with surrounding anatomical tissues following implantation. The exact composition of an implant (e.g., PVA or other hydrogel materials, water, saline or other liquids, other additives, etc.) can be selected so as to provide the resulting implant with the desired or required strength, load bearing capacity, compressibility, flexibility, longevity, durability, resilience, coefficient of friction and/or other properties and characteristics.

In several embodiments, the implants disclosed herein are configured for drug delivery and/or are seeded with growth factors and/or cells. In some embodiments, the implants comprise one or more of the following: chondrocytes, growth factors, bone morphogenetic proteins, collagen, hyaluronic acid, nucleic acids, and stem cells. Such factors and/or any other materials included in the implant and selectively delivered to the implant site can help facilitate and promote the long-term fixation of the implant within the joint or other target area of the anatomy.

In some embodiments, the implants disclosed herein are configured for anchoring during implantation. The implant can comprise one or more anchor sites (which may comprise non-hydrogel portions or tabs) to facilitate anchoring (e.g., suturing, stapling, etc.). In one embodiment, the implant is pre-coupled to one or more anchors. Such anchors can comprise removable and/or permanent fixtures. In some embodiments, the anchors are resorbable or otherwise dissolvable after implantation (e.g., following a particular time period, such as, for instance, 1-30 days, 2-30 weeks, 6-12 months, 1-5 years, greater than 5 years, less than 1 day, etc.). In one embodiment, the implant comprises at least one abrasive surface. In one embodiment, the implant comprises one or more adhesive components. In other embodiments, the tapered shape of the implant permits secure implantation without the need for any anchoring or other fixation. In some embodiments, for any of the implants disclosed herein, one or more implant surfaces can be configured to promote bone adhesion by one or more coatings, substances and/or the like and/or by using an appropriate surface texture along the surface(s). For example, the implant surface can be roughened, can include pores (e.g., superficial pores) and/or any other feature, as desired or required.

In some embodiments, the implants disclosed herein are supported or reinforced by a rigid support frame, such as a ceramic or metallic frame. In some embodiments, the implants disclosed herein are supported or reinforced by a flexible or rigid mesh structure. In other embodiments, the implants do not contain any support or reinforcement structure.

Any of the implant embodiments disclosed herein, or equivalents thereof, can be manufactured using freeze/thaw cycling and/or any other production method. For example, a hydrogel formulation comprising water, saline, PVA (and/or other hydrogel materials), other polymeric materials, other additives and/or the like can be heated and/or otherwise treated as part of a freeze/thaw manufacturing process. In one embodiment, a hydrogel solution comprising saline and about 40% PVA by weight is heated to approximately 121° C. under elevated pressure conditions (e.g., to affect dissolution of the polymer). For example, such a solution can be autoclaved in order to facilitate complete or substantially complete dissolution of the PVA in the saline, water and/or other liquid. Next, the temperature and/or pressure of the solution can be lowered to permit entrapped air and/or other gases to escape. In one embodiment, after the autoclaving or similar step, the solution is generally maintained at a temperature of approximately 95° C. and atmospheric pressure for a predetermined time period.

Figure 4:
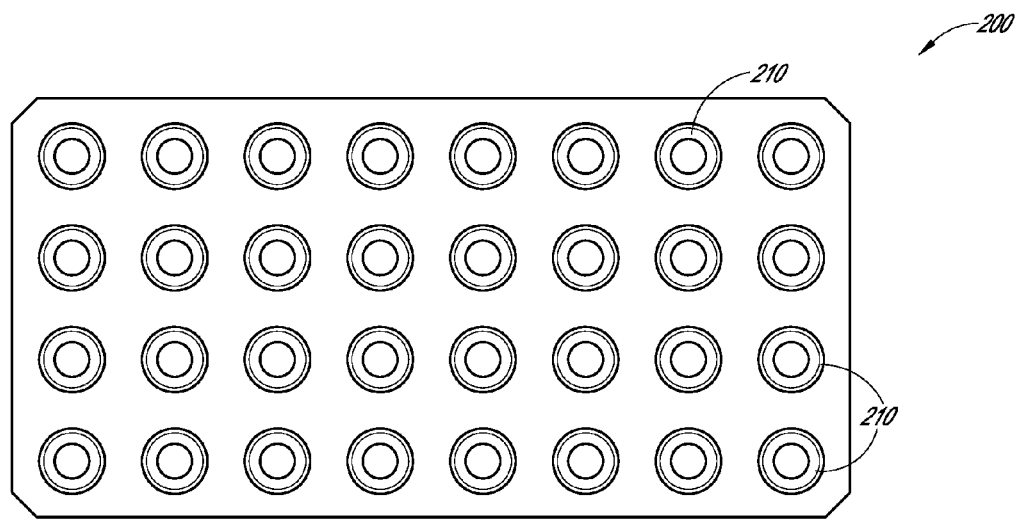
FIG. 4 illustrates a top view of an open mold assembly for making tapered implants, according to one embodiment.
Figure 5:
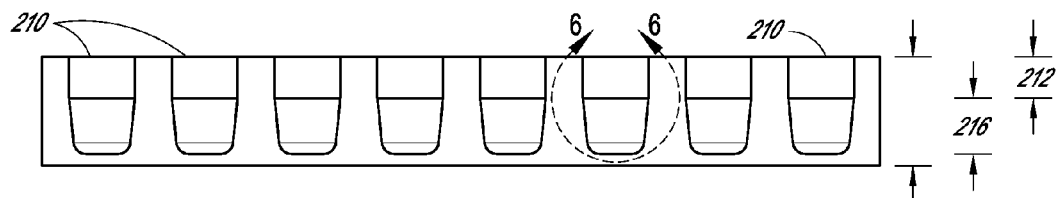
FIGS. 5 and 6 illustrate side views of the mold assembly of FIG. 4.
Figure 6:
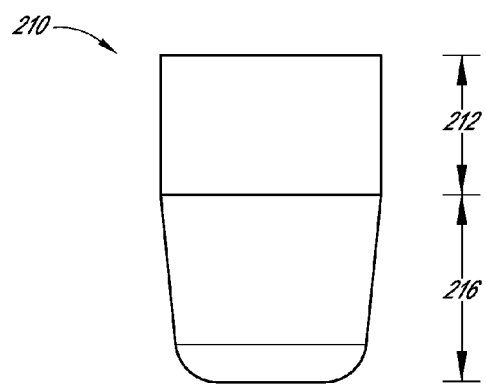

The solution can then be transferred (e.g., pumped, poured, etc.) into open molds where, once set, will form the desired shape of the implants. One embodiment of such an open mold assembly 200 is illustrated in FIGS. 4-6. As shown, the open mold assembly 200 can include a plurality of individual mold cavities 210, each of which is configured to receive a hydrogel solution. With specific reference to the cross sectional views of FIGS. 5 and 6, in some embodiments, the hydrogel solution is configured to fill only a lower portion 216 mold's assembly cavities 210. Alternatively, the cavities can be filled with the desired hydrogel solution to a level that is above the lower portion 216. Accordingly, under such circumstances, the resulting device that is formed therein will extend into the upper portion 212 of the cavity 210. As described in greater detail below, any part of the device that extends above the lower portion 216 can be removed in order to produce an implant having generally sloped or contoured side walls and a reverse tapered design, in accordance with various implant arrangements disclosed herein.

With continued reference to FIGS. 4-6, the cavities 210 of the mold assembly 200 can be shaped, sized and otherwise configured so that the implants formed therein comprise a wedge, truncated cone or reverse taper design. For example, in such designs, the base ends of the implants are generally larger than the corresponding, opposite top ends. Once the implants have been molded, they can be removed from the upper ends of the assembly 200. The molded items can be removed either after initial formation or after they undergo additional treatment (e.g., freeze/thaw cycling, other heat and/or pressure treatment, etc.). As noted above, depending on how much hydrogel solution is placed in the cavities, the molded implants removed from the cavities 210 of the assembly 200 may need to be cut, altered or otherwise processed. For example, in some embodiments, any portion of the implants formed by the generally cylindrical cavity section in the upper portion 212 of the cavities may need to be excised and discarded as part of a subsequent reshaping step. Accordingly, the remaining implants can generally resemble the shape of the implant embodiment of FIGS. 3A and 3B or any other implant having a generally reverse taper or wedge design.

Due in part to the remaining production steps, accommodation of any changes in size (e.g., expansion, contraction, etc.) that may occur or are likely to occur to the implants can be considered during manufacturing by properly sizing and otherwise designing the mold assembly 200. The amount of contraction or expansion of the implants can be based on one or more factors or conditions, such as, for example, the number of freeze/thaw cycles to which the implants are subjected, the temperature and/or pressure ranges associated with the remaining steps and/or the like.

Alternatively, the implants can be formed, at least in part, using an injection molding process and/or any other molding or casting procedure. In such injection or transfer molding techniques, once the hydrogel or other implant solution has been prepared, it can be loaded into an injection cylinder or other container of a molding press. The solution can then be forcibly transferred into a closed mold assembly using a pneumatic or hydraulic ram or any other electromechanical device, system or method. In some embodiments, the hydrogel and/or other solution or implant component is injected into a corresponding closed mold assembly through a standard runner and gate system. Injection molding of implants can provide one or more benefits relative to open mold assemblies. For instance, the devices formed as part of the injection molding techniques typically do not require additional cutting, reshaping, resizing and/or processing, as they are essentially in their final shape immediately after the injection molding step has been completed.

Regardless of how the implants are molded or otherwise shaped or manufactured, they can be subsequently subjected to one or more freeze/thaw cycles, as desired or required. In some embodiments, for example, the implants, while in their respective mold cavities, are cooled using a total of four freeze/thaw cycles wherein the temperature is sequentially varied between approximately −20° C. and 20° C. In other embodiments, however, the number of freeze/thaw cycles, the temperature fluctuation and/or other details related to cooling the implants can be different than disclosed herein, in accordance with a specific production protocol or implant design.

Following freeze/thaw cycling, the implants can be removed from their respective mold cavities and placed in one or more saline and/or other fluid (e.g., other liquid) baths where they can be subjected to additional cooling and/or other treatment procedures (e.g., to further stabilize the physical properties of the implants). According to some embodiments, for instance, the implants undergo an additional eight freeze/thaw cycles while in saline. In other embodiments, such follow-up cooling procedures are either different (e.g., more or fewer freeze/thaw cycles, different type of bath, etc.) or altogether eliminated from the production process, as desired or required.

When the cooling (e.g., freeze/thaw cycling) and/or other treatment steps have been completed, the implants can be inspected to ensure that they do not include any manufacturing flaws or other defects. Further, at least some of the implants can be subjected to selective testing to ensure that they comprise the requisite physical and other characteristics, in accordance with the original design goals and target parameters for the implants. Further, it may be necessary to cut or otherwise process the implants in order to remove any excess portions. In some embodiments, the completed implants are packaged in hermetically sealed plastic trays (or other containers) comprising foil or other types of lids or covering members. A volume of saline and/or other liquid can be included within such trays or other containers to ensure proper hydration of the implants during storage and/or any other steps preceding actual use. In one embodiment, the implant trays or other containers are terminally sterilized using e-beam exposure between about 25 and 40 kGy. Additional details related to producing hydrogel implants can be found in U.S. Pat. Nos. 5,981,826 and 6,231,605, the entireties of both of which are hereby incorporated by reference herein.

According to some embodiments, the overall height (e.g., between the base or bottom surface and the top or articulating surface) of a tapered implant is approximately 10 mm. Further, the diameter or other cross-sectional dimension along or near the top surface of the implant can be about 10 mm. However, in other embodiments, the height, diameter and/or other dimensions of a wedge-type implant can vary, as desired or required. For example, implants adapted for use in larger joints (e.g., knee, shoulder, hip, etc.) can have a height and/or diameter larger than 10 mm (e.g., about 11 mm, 12 mm, 13 mm, 14 mm, 15 mm, 16 mm, 18 mm, 20 mm, greater than 20 mm, dimensions between the foregoing values, etc.). Likewise, implants configured for use in smaller joints (e.g., toes) can be smaller than 10 mm in height (e.g., about 2 mm, 4 mm, 6 mm, 8 mm) and/or 10 mm in top diameter (e.g., about 2 mm, 4 mm, 6 mm, 8 mm).

As discussed above with reference to FIGS. 1 and 2, in order to ensure that the implant securely remains within a joint or other anatomical location following implantation, the implant can be positioned within an implant site that also comprises a similar reverse taper, wedge or truncated cone shape. Accordingly, several embodiments of making such a tapered recess or other opening within bone tissue are described in greater detail below.

Figure 7:
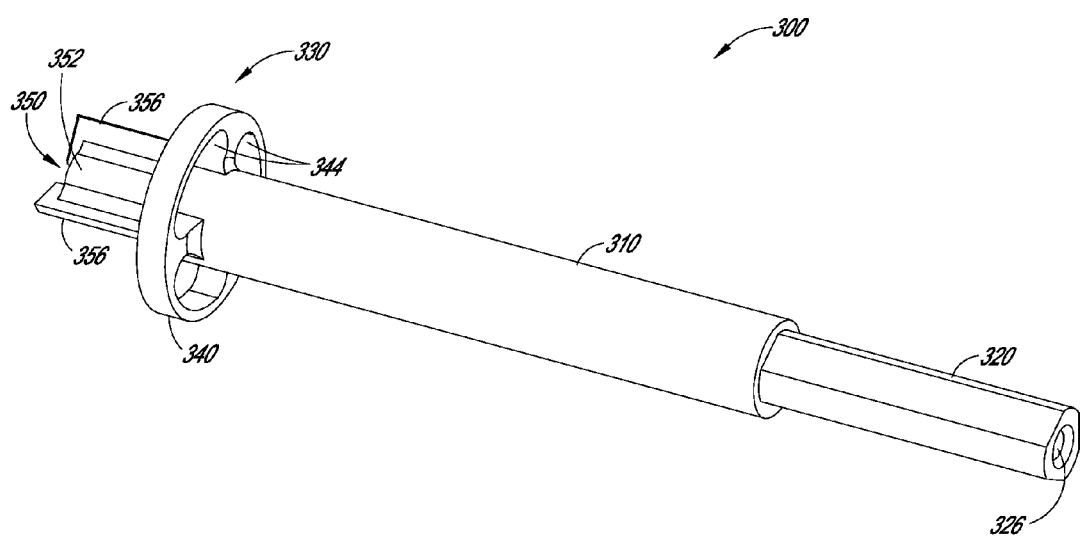
FIG. 7 illustrates a perspective view of a drill bit configured for use with a bone drill, according to one embodiment.
Figure 8A:
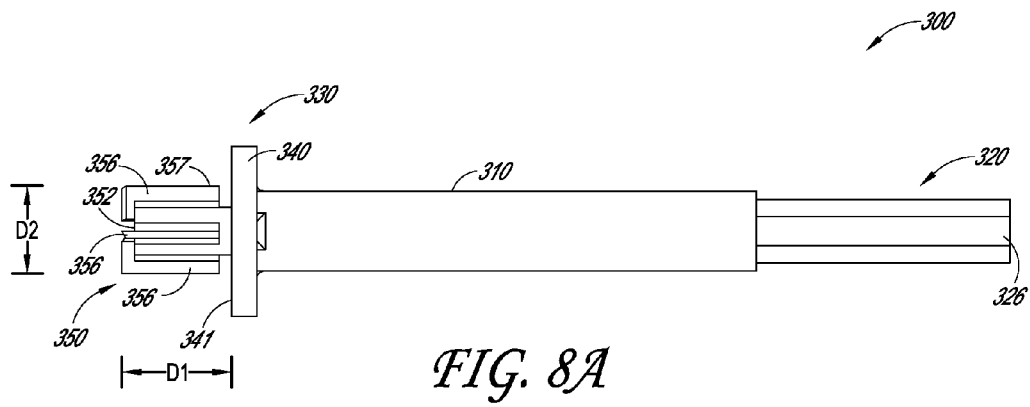
FIGS. 8A and 8B illustrate side views of the drill bit of FIG. 7.
Figure 8B:

FIGS. 7-8B illustrate one embodiment of a drill bit 300 that can be used to create a reverse taper recess into which an implant may be positioned. As shown, the drill bit 300 can comprise a main body portion 310 that extends at least partially along the longitudinal dimension of the drill bit 300. In the illustrated embodiment, the proximal end 320 of the drill bit 300 comprises a shaft 322 that is sized, shaped and otherwise configured to selectively mate with a corresponding portion of a bone drill (not shown). In the depicted embodiment, the shaft 322 comprises a generally triangular cross-sectional shape, as shown in FIG. 8D. However, in alternative arrangements, the shape, size and/or other details of the shaft can vary. The shaft 322 can include a standard or non-standard configuration. Bone drills with which the various drill bit embodiments disclosed herein are used can be either manually operated or power driven (e.g., mechanically, pneumatically, hydraulically, etc.).

Figure 8C:
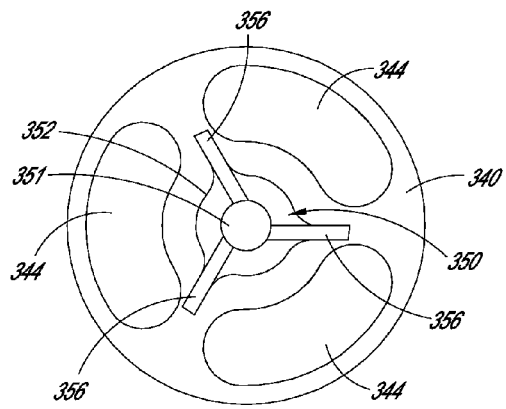
FIG. 8C illustrates a distal end view of the drill bit of FIG. 7.
Figure 8D:
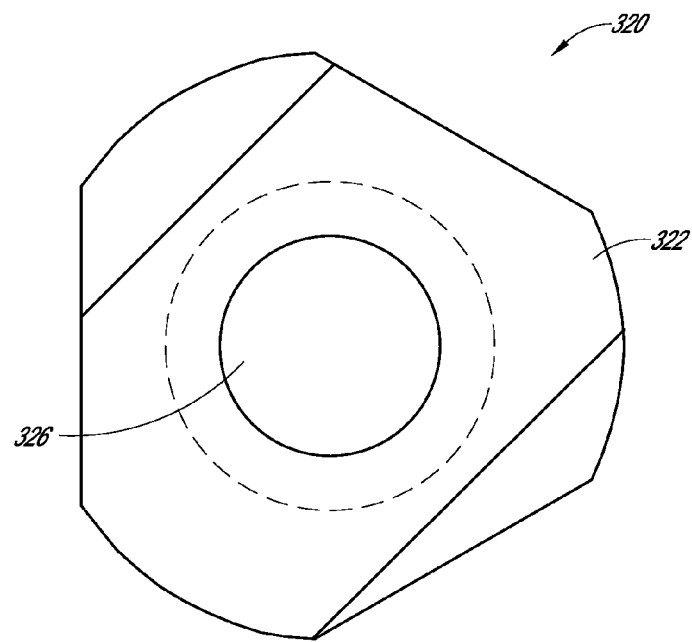
FIG. 8D illustrates a cross sectional view of the proximal shaft portion of the drill bit of FIG. 7.
Figure 8E:
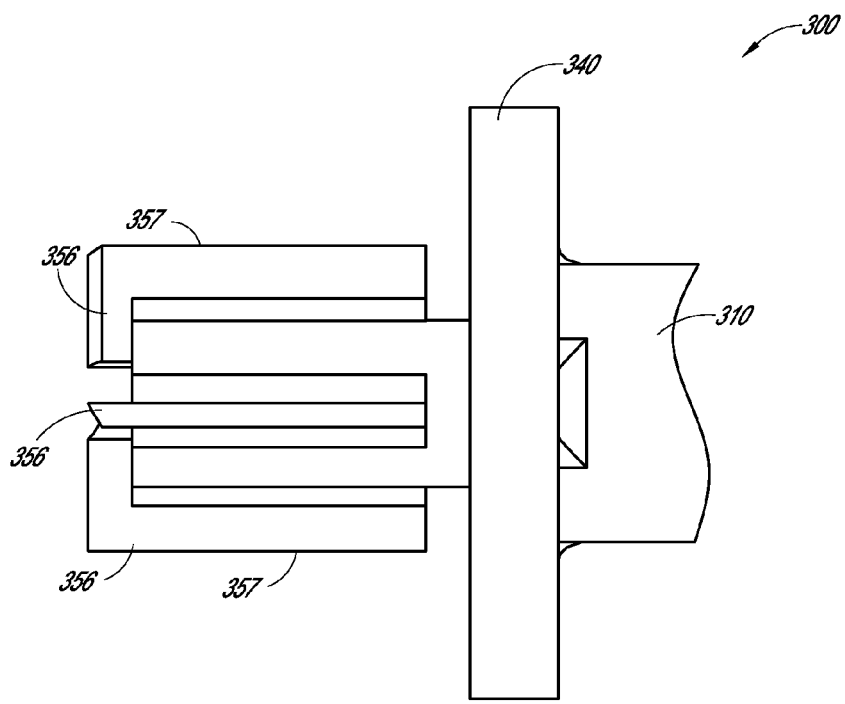
FIG. 8E illustrates a detailed side view of the distal working end of the drill bit of FIG. 7.

With continued reference to FIGS. 7, 8A and 8B, and as shown in the detail view of FIG. 8E, a distal end 330 of the drill bit 300 can include a flange 340 and one or more abrading members or cutters 356 extending distally from the flange 340. As best illustrated in the front view of FIG. 8C, the drill bit 300 can comprise a total of three cutters 356 that are generally equally spaced apart (e.g., at angles of approximately 120° relative to one another). In other embodiments, however, the quantity, size, shape, position, orientation, spacing and/or other characteristics or properties of the cutters 356 can be different than illustrated herein. For example, in some arrangements, a drill bit can include more or fewer cutters (e.g., 1, 2, 4, 5, more than 5), as desired or required. Likewise, the cutters can be larger or smaller or can extend along different portions of the distal end of the drill bit.

According to some embodiments, a drill bit can be cannulated, such that one or more passages or openings 326 extend (e.g., longitudinally) through the device. For example, as illustrated in FIGS. 7 and 8A-8E, such a passage 326 can generally extend from the proximal end of the drill bit 300 to the distal end, terminating in an opening 351 along the distal hub 352 to which the cutters 356 are secured. As discussed in greater detail below, the inclusion of such passages or openings 326 can help ensure that the drill bit is accurately positioned within a patient's joint or other portion of the anatomy before commencing a drilling procedure.

As the drill bit 300 is rotated (e.g., either manually or using one or more external driving sources, etc.), sharp edges formed along the distal and/or peripheral portions of the cutters 356 can abrade and remove cartilage, bone and/or other tissue that they engage and contact. In some embodiments, the longitudinal distance D1 (FIG. 8A) between the distal face 341 of the flange member 340 and the distal ends of the cutters 356 can limit the depth of the recess or opening that is created within the patient's bone or other anatomical area. Likewise, the peripheral surfaces of the cutters 356 can define a diameter or other cross-sectional dimension D2 (FIG. 8A) that effectively limits the diameter of the resulting recess or other openings in the patient's bone or other targeted tissue. Thus, each drill bit 300 can be configured to create an implant site having specific dimensions (e.g., depth, diameter, etc.). Consequently, in some arrangements, drill bits of varying size and shape are available to the surgeon or other clinician in order to accurately create a specific desired implant site within the patient. For any of the embodiments disclosed herein, the distal edges and/or other surfaces of the cutting blades or cutters can be generally flat and/or otherwise contoured (e.g., to generally match and/or receive the base of the implant).

As the drill bit 300 is rotated and advanced into a targeted region of the patient's anatomy, abraded bone, cartilage and/or other tissue and/or other debris will be created at or near the distal end 330 of the device. Accordingly, in order to permit such debris to be removed from the treatment site, the flange 340 can include one or more openings 344. Thus, abraded materials can stay clear of and not interfere with the working end of the drill bit, allowing the cutters 356 to continue to function normally. Once the distal face 341 of the flange 340 abuts the top surface of the bone being drilled, further advancement of the drill bit 300 can be prevented. This alerts the clinician that the implant site having the desired depth and diameter has been properly created.

With continued reference to the front view of FIG. 8C, the cutters 356 can be joined along a hub 352 along or near the center of the distal face 341 of the flange 340. As shown, the cutters 356 can extend at least radially outwardly from the central hub 352, toward the outer periphery of the flange 340. As noted above, the radial length of the cutters 356 can help determine the diameter of the recess or opening that will be created within a patient's bone or other tissue. In the depicted embodiment, however, because of the generally vertical orientation of the peripheral edges 357 of the cutters 356, the corresponding implant opening that will be created by the drill bit 300 will be generally cylindrical. Therefore, additional implant site preparation is required in order to create an opening having a reverse taper shape.

Accordingly, a drill bit having an articulating cutter or a movable cutting arm can be used to create the necessary taper or slope along the side walls of the recess or opening in a bone or other targeted region of the anatomy. In some embodiments, the articulating cutter is configured to create a curved contour along the bottom and/or side surfaces of the recess. For example, such curved surfaces can include one or more convex and/or concave portions, as desired or required. One embodiment of a drill bit 400 configured to create such a reverse tapered implant site is illustrated in FIGS. 9A-9D. Like the arrangement discussed above with reference to FIG. 7, the depicted drill bit 400 can comprise a main body portion 410 that terminates at or near a distal flange assembly 440. Further, a proximal end of the drill bit 400 can comprise a shaft 420 that is sized, shaped and otherwise configured to engage and mate with a corresponding portion of a drill (not shown). In addition, a central hub 452 located along on near the distal face 441 of the flange 440 can help secure one or more stationary cutters 456 that are configured to abrade bone, cartilage and/or other tissue with which they come in contact. The arrangement illustrated in FIGS. 9A-9D comprises two stationary cutters 456 that are spaced generally opposite of each other (e.g., 180° apart). However, in alternative embodiments, a drill bit comprises more or fewer stationary cutters, as desired or required.

Figure 9A:
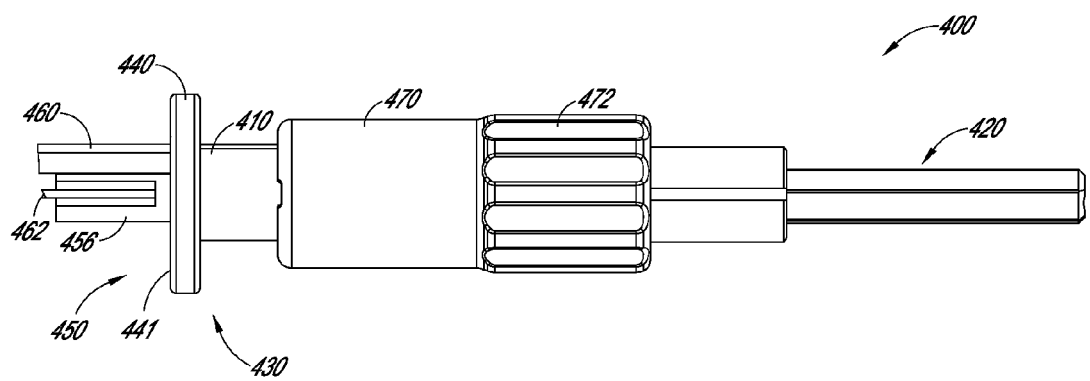
FIG. 9A illustrates a side view of one embodiment of a drill bit with an articulating cutter in a stowed or retracted orientation.
Figure 9B:
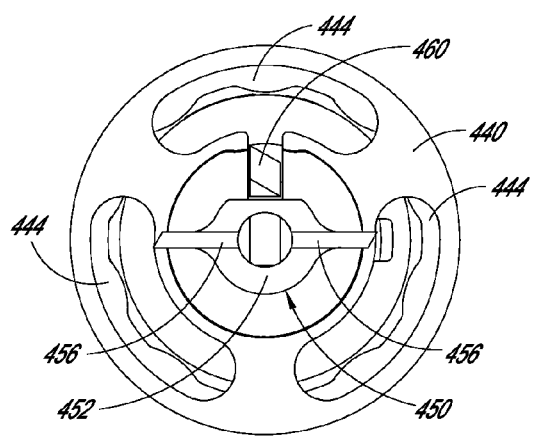
FIG. 9B a distal end view of the drill bit of FIG. 9A.

With continued reference to FIGS. 9A and 9B, the drill bit 400 can additionally comprise one or more articulating cutters or movable cutting arms 460. As discussed in greater detail herein, such a movable cutter 460 can be selectively deployed (e.g., radially outwardly about a hinge or other pivot point) in order to create a desired draft angle along the side of the implant site. In FIGS. 9A and 9B, the articulating cutter 460 is shown in the stowed or radially contracted position. Thus, as the drill bit is rotated and advanced into a bone, a generally cylindrical bore or opening will be created by the stationary cutters 456. Once the drill bit 400 can been advanced sufficiently far into the targeted bone or other site, the distal face 441 of the flange 440 will contact and abut an exterior surface of the bone or other site being drilled. This can prohibit the continued advancement of the cutters 456 and advantageously limit the depth of the resulting implant site.

Figure 9C:
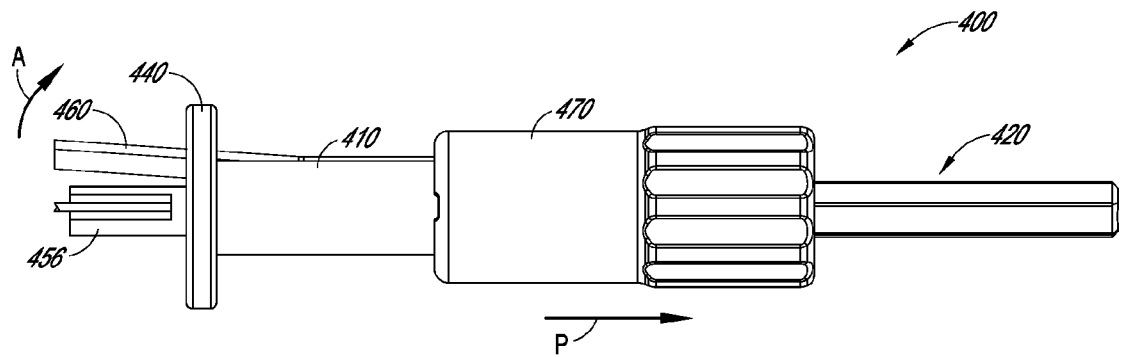
FIG. 9C illustrates a side view the drill bit of FIG. 9A with its articulating cutter in an extended or deployed orientation.
Figure 9D:
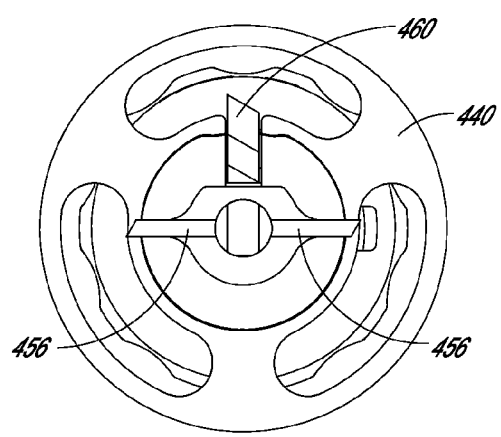
FIG. 9D a distal end view of the drill bit of FIG. 9C.

According to some embodiments, once the stationary cutters 456 of the drill bit 400 have created a generally cylindrical recess or opening within the patient's targeted bone or other site and the flange 440 contacts a corresponding abutting surface, the surgeon or other clinician can cause the articulating cutter 460 to be deployed outwardly. Thus, the desired reverse taper or wedge shape can be created along the sides of the implant site. As shown in FIG. 9C, in one embodiment, the articulating cutter 460 is moved outwardly by selectively retracting a sleeve 470 in the proximal direction (e.g., away from the flange 440 and the distal end of the drill bit, as generally represented in FIG. 9C by arrow P). In some embodiments, the sleeve 470 includes a contoured grip portion 472 to allow the user to more easily grasp and retract the sleeve 470. Consequently, the articulating cutter 460 can be rotated or otherwise moved in a manner generally represented by arrow A. This permits the peripheral edge of the articulating cutter 460 to contact and abrade additional bone, cartilage and/or other tissue, thereby creating the desired reverse taper or truncated cone shape within the recess R (FIG. 2).

In some embodiments, once released outwardly (e.g., by retraction of the sleeve 470), the articulating cutter 460 can assume a fully extended orientation in order to create the necessary taper to the adjacent side walls of the implant site. Thus, a sufficiently strong biasing or other type of force can be imparted on the articulating cutter 460 to ensure that it can reach the targeted fully deployed position. The articulating cutter 460 can be biased radially outwardly using a spring or other resilient member. Alternatively, any other force imparting device or method can be used to ensure that the articulating cutter 460 fully extends when selectively deployed by the clinician. Once the necessary taper along the sides of the implant site has been created, the sleeve 470 can be returned to its original orientation (e.g., closer to the flange 440, as illustrated in FIG. 9A), causing the articulating cutter 460 to move to its stowed or radially retracted position.

Figure 10A:
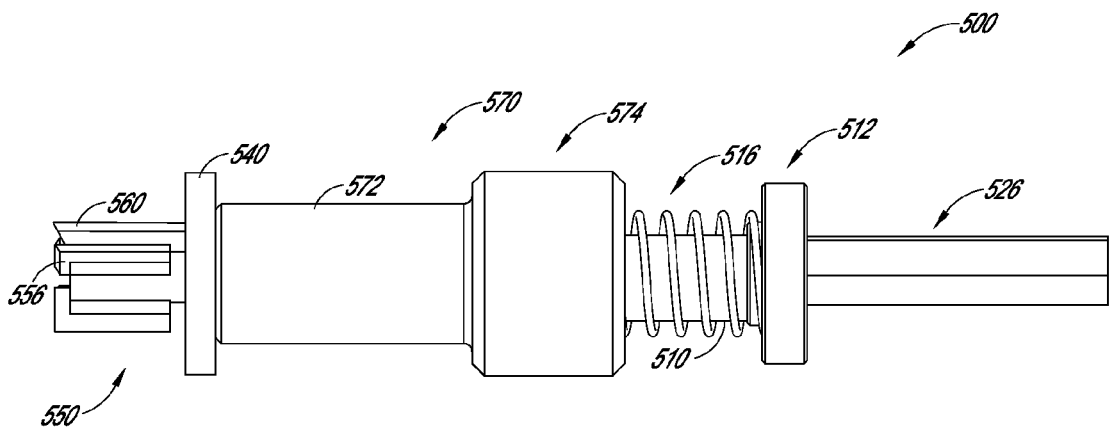
FIG. 10A illustrates a side view of one embodiment of a drill bit with an articulating cutter in a stowed or retracted orientation.
Figure 10B:
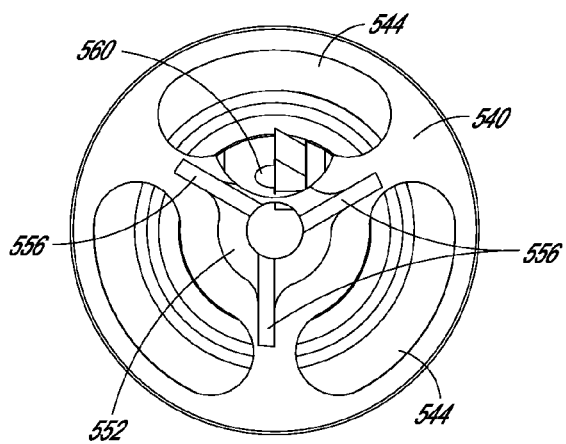
FIG. 10B a distal end view of the drill bit of FIG. 10A.

According to some embodiments, the sleeve 470 is normally resiliently biased in the distal position (e.g., as illustrated in FIG. 9A). Thus, in such configurations, as discussed above, a surgeon or other user needs to retract the sleeve 470 proximally relative to the main body portion 410 of the drill bit 400 in order to deploy the articulating cutter 460. In one embodiment, as illustrated in FIG. 10A, the sleeve 570 is normally maintained in a distal orientation with the assistance of a spring 516 or other resilient member. In the illustrated embodiment, the sleeve 570 includes a body portion 572 and an enlarged grip portion 574. A proximal end of the spring 516 can be coupled to a stop nut 512 coupled to or integrally formed with the main body portion 510. The sleeve 570 contacts the stop nut 512 to prevent further retraction once the articulating cutter 560 has been deployed. However, any other device or method can be used to normally maintain the position of the sleeve 470, 570 relative to adjacent portions of the drill bit 400, 500 (e.g., the main body portion 410, 510). For example, in some embodiments, the drill bit is configured to automatically deploy the articulating cutter in a outwardly oriented position once the flange of the drill bit contact the outer surface of the bone structure or other treatment site (e.g., once the cylindrical recess has been made to the desired depth). In such arrangements, the articulating cutter can be deployed in its expanded position as a result of automatic mechanical actuation between the flange, cutter and/or other portion of the drill bit relative to the implant site.

In other embodiments, a reverse tapered recess can be created using a two or multi-step process. For example, as part of an initial step, a first drill bit can be used to create a generally cylindrical opening within a targeted bone. One embodiment of a drill bit that is configured to only create a generally cylindrical opening is illustrated and discussed herein with reference to FIGS. 7 and 8A-8C. Then, once the first drill bit has been removed, a second drill bit having an articulating arm, such as, for example, the bit discussed herein with reference to FIGS. 9A-9D and 10A-10D, can be inserted into the generally cylindrical opening. By moving the articulating cutter to its extended position, therefore, the desired wedge or reverse tapered shape can be created within the recess or implant site.

Figure 10C:
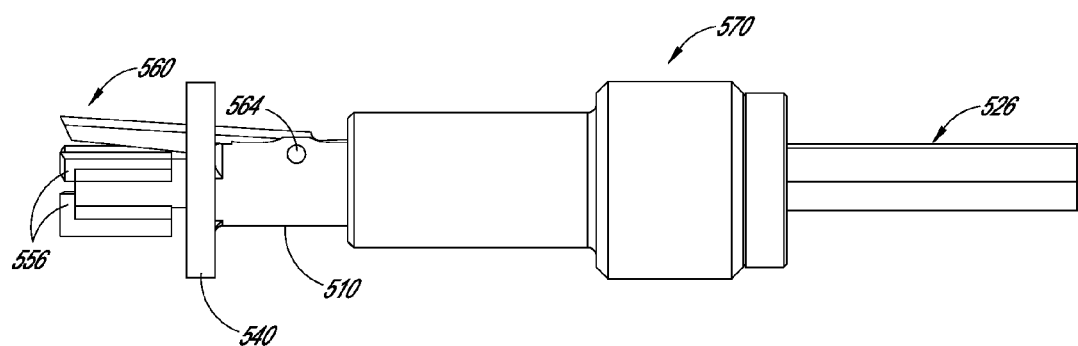
FIG. 10C illustrates a side view the drill bit of FIG. 10A with its articulating cutter in an extended or deployed orientation.
Figure 10D:
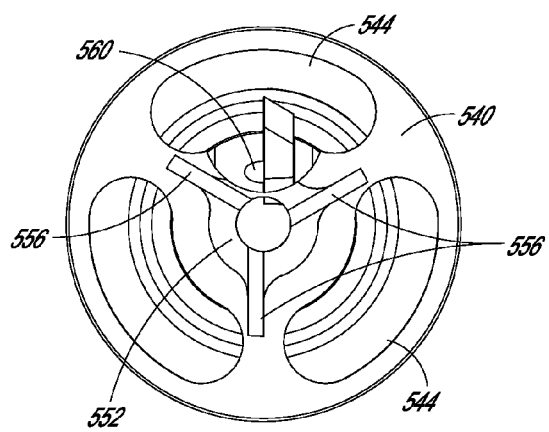
FIG. 10D a distal end view of the drill bit of FIG. 10C.
Figure 11:
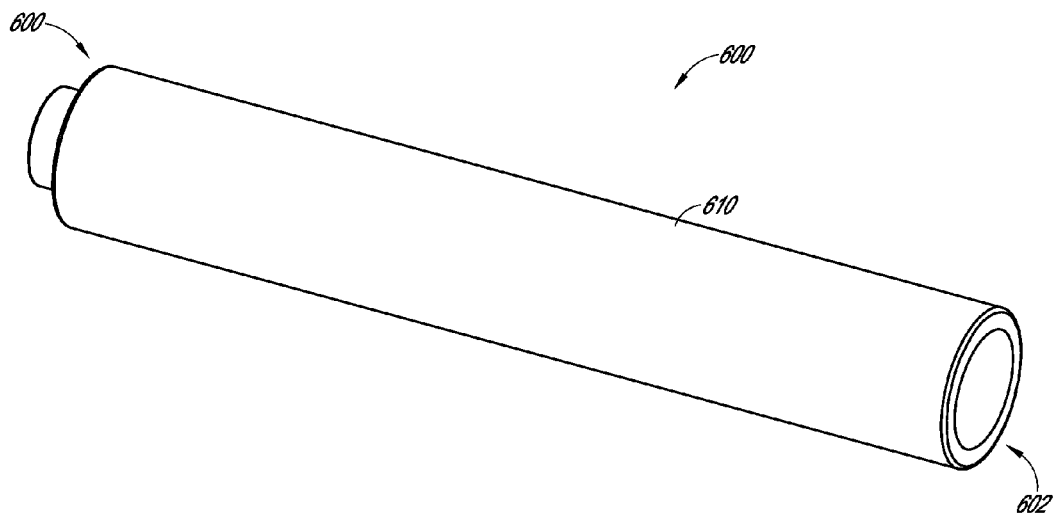
FIG. 11 illustrates a perspective view of an implant introducer according to one embodiment.

With reference to FIG. 10A, a drill bit 500 can comprise a total of three stationary cutters 556 and an articulating cutter 560. However, in other arrangements, a drill bit can comprise more or fewer stationary cutters 556 and/or articulating cutters 560, as desired or required by a particular application or use. Further, as depicted in FIG. 10C, the articulating cutter 560 can attach to the main body 510 and/or any other portion of the drill bit 500 using a hinge 564 or other pivot point. Thus, as discussed in greater detail above with reference to FIGS. 9A-9D, the articulating cutter 560 can be selectively rotated about such a hinge 564 between stowed and extended orientations. Accordingly, the drill bits 400, 500 illustrated in FIGS. 9A-9D and 10A-10D can be advantageously used to create an implant site having a desired reverse taper or wedge design. In other embodiments, drill bits comprising articulating cutters can be introduced into the implant site after a generally cylindrical recess or opening has been created by a drill bit that does not include an articulating cutter (e.g., the drill bit shown in FIG. 7), as part of a two-step procedure.

According to some embodiments, the drill bit can be advanced to the targeted drill site of the patient bone or other anatomical location with the assistance of a guide pin. As discussed herein, any one of the drill bit arrangements disclosed herein can include a longitudinal lumen or other passage. Thus, a guide pin can be tamped at least partially into the surface of the bone to be drilled. The guide pin may be advanced through the patient's anatomy using a trocar or similar device. Next, a cannulated drill bit, as discussed herein, can be passed over the guide pin to ensure that the distal, working end of the drill bit is properly positioned relative to the treatment site (e.g., joint).

Figure 14:
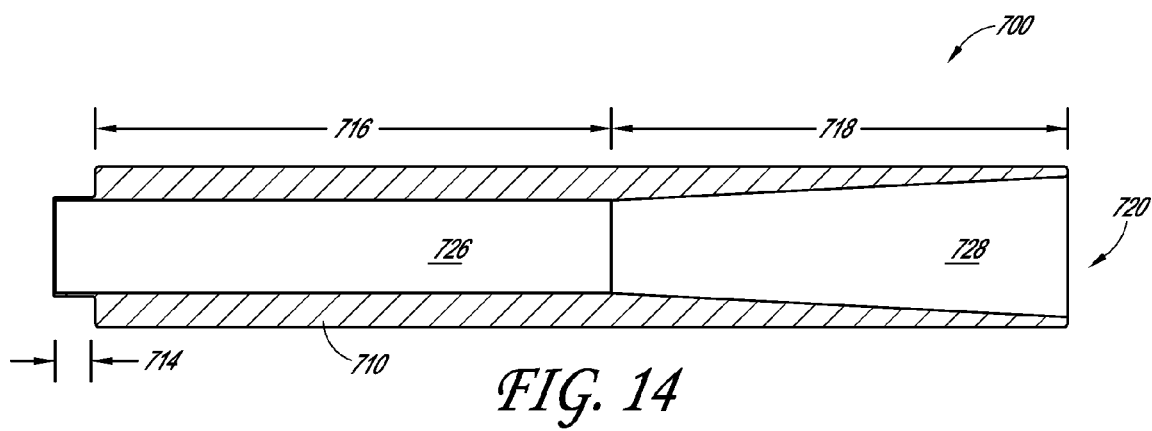
FIG. 14 illustrates a longitudinal cross-sectional view of another embodiment of an implant introducer.

Once a reverse taper implant site has been created in the targeted joint or other portion of the patient (and, where applicable, the guide pin or other member has been removed), a clinician can deliver the implant to the implant site using an introducer 600. As illustrated in FIGS. 11-13B, an introducer 600 can include a generally cylindrical introducer tube 610 having an opening 620 through which the implant may be passed. In some embodiments, the distal end 606 of the introducer tube 610 can comprise a neck or other narrowed portion 608. As shown in FIG. 13B, the neck portion 608 can include a wall 612 having a rounded distal edge 613. In some embodiments, the neck portion 608 has a length (labeled 614 in FIG. 12B) of about 0.155 inches to about 0.170 inches. Further, as best illustrated in the longitudinal cross-sectional view of FIG. 12B, the internal diameter of the introducer tube 610 can vary along its length. For example, in the depicted embodiment, a proximal portion 618 of the introducer 600 comprises a flared shape, wherein the inside diameter of the opening 620 is progressively reduced in the proximal to distal direction. Further, as shown, the opening 620 can maintain a generally constant inner diameter along a second, more distal portion 616 of the introducer tube 610. In other embodiments, the inner diameter, length, other dimension and/or other details or properties of the introducer 600, including its flared interior portion 628, its generally cylindrical interior portion 626 of the introducer tube 610, its neck portion 608 and/or the like can be different than shown in FIGS. 11, 12A-12B and 13A-13B and described herein. By way of example, the embodiment illustrated in FIG. 14 comprises a longer flared interior portion 728 (e.g., relative to the adjacent generally cylindrical portion 726) than the introducer 600 of FIG. 12B.

Figure 15A:
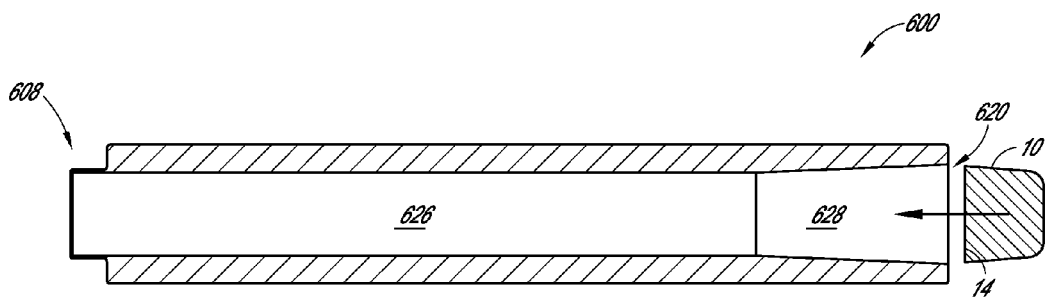
FIGS. 15A-15C illustrate time-sequential side views of an implant being inserted within an implant site using the introducer of FIG. 11.
Figure 15B:
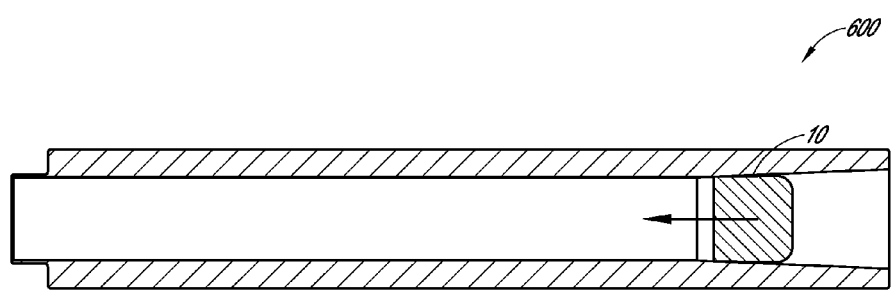
Figure 15C:
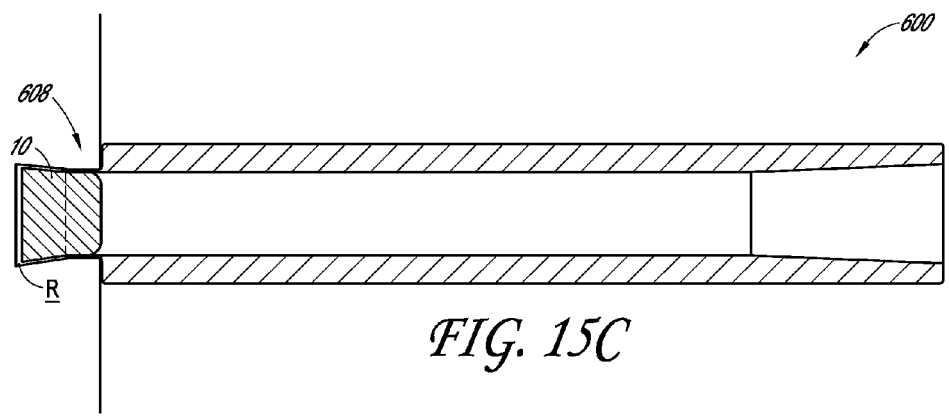

The neck portion 608 of the introducer tube 610 can be positioned at least partially within the opening or recess into which the implant will be secured. In some embodiments, the introducer can be sized, shaped and otherwise configured to that the neck portion 608 fits generally snugly within the implant site. With reference to FIGS. 15A-15C, an implant 10 can be placed within the opening 628 along the proximal end 602 of the introducer 600. As shown, in some embodiments, the implant 10 is advanced into the interior of the introducer 600 with its base or bottom 14 end first.

As the implant 10 is urged deeper (e.g., more distally) into the interior of the introducer 600, the implant 10 may become radially compressed by the adjacent interior walls. If sufficient force is applied to the implant 10, the implant 10 passes through the neck portion 608 of the introducer and into the implant site R. As illustrated in FIG. 15C, in such an arrangement, the implant's base end 14 will be located along the bottom of the implant site. According to some embodiments, a plunger or other pusher member (not shown) can be inserted within the interior of the introducer to help push the implant through the introducer and into the implant site. Such a plunger or pusher member can be operated manually and/or with the assistance of an external power-assist device (e.g., mechanically, pneumatically, hydraulically, etc.), as desired or required.

Figure 16B:
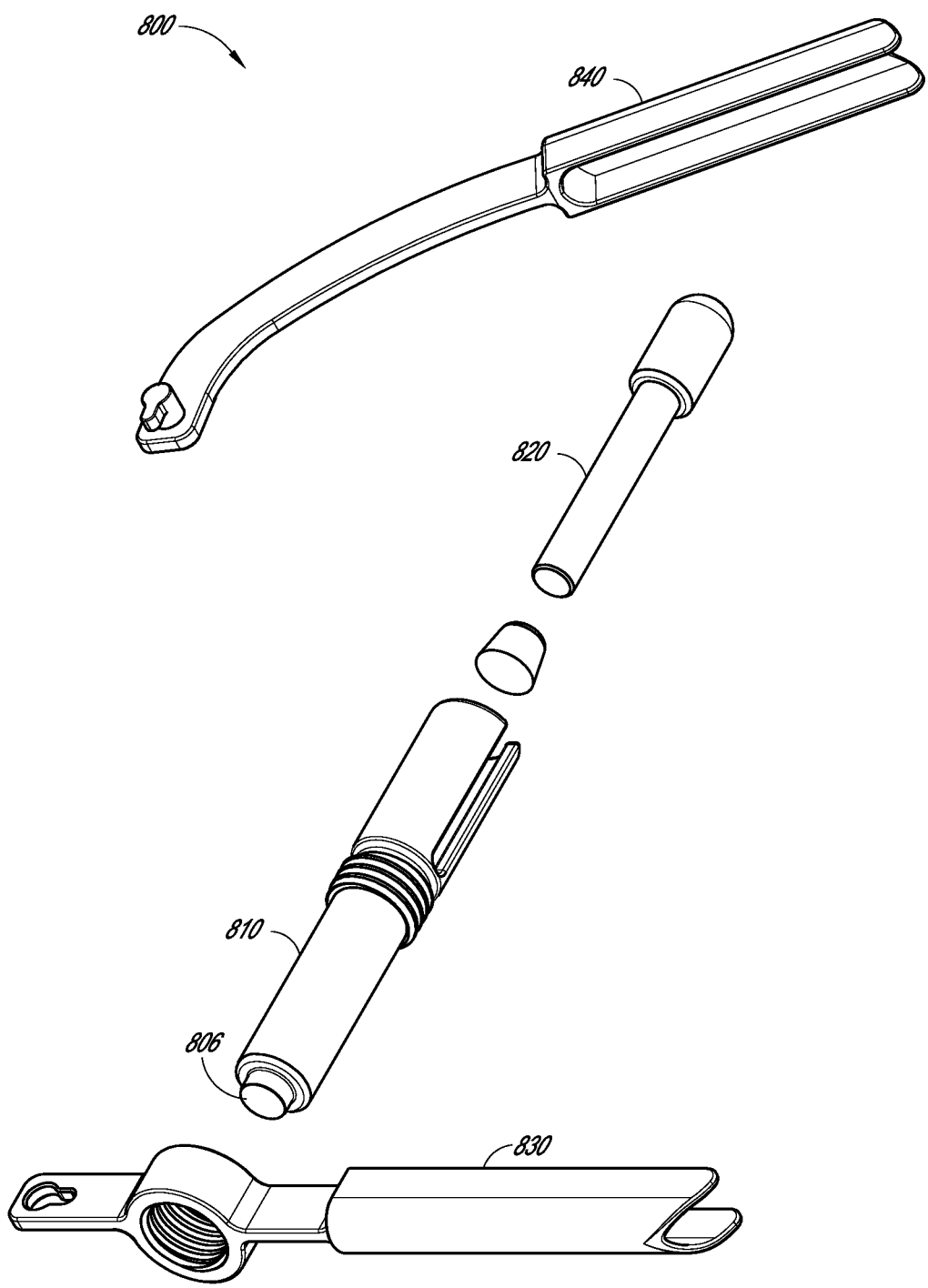
FIG. 16B illustrates an exploded view of the delivery tool of FIG. 16A.
Figure 16C:
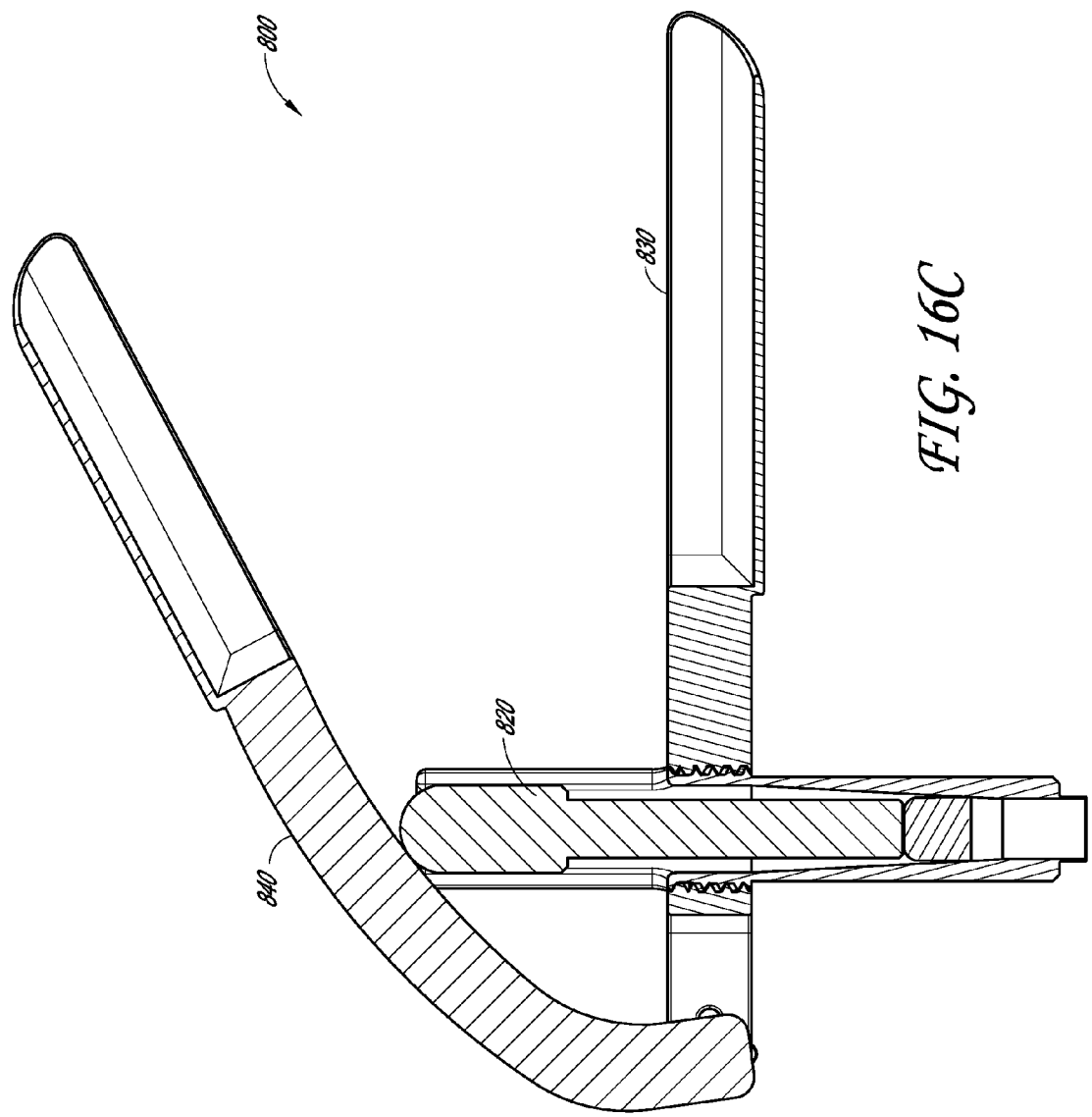
FIG. 16C illustrates a cross-sectional view of the delivery tool of FIG. 16A.
Figure 16E:
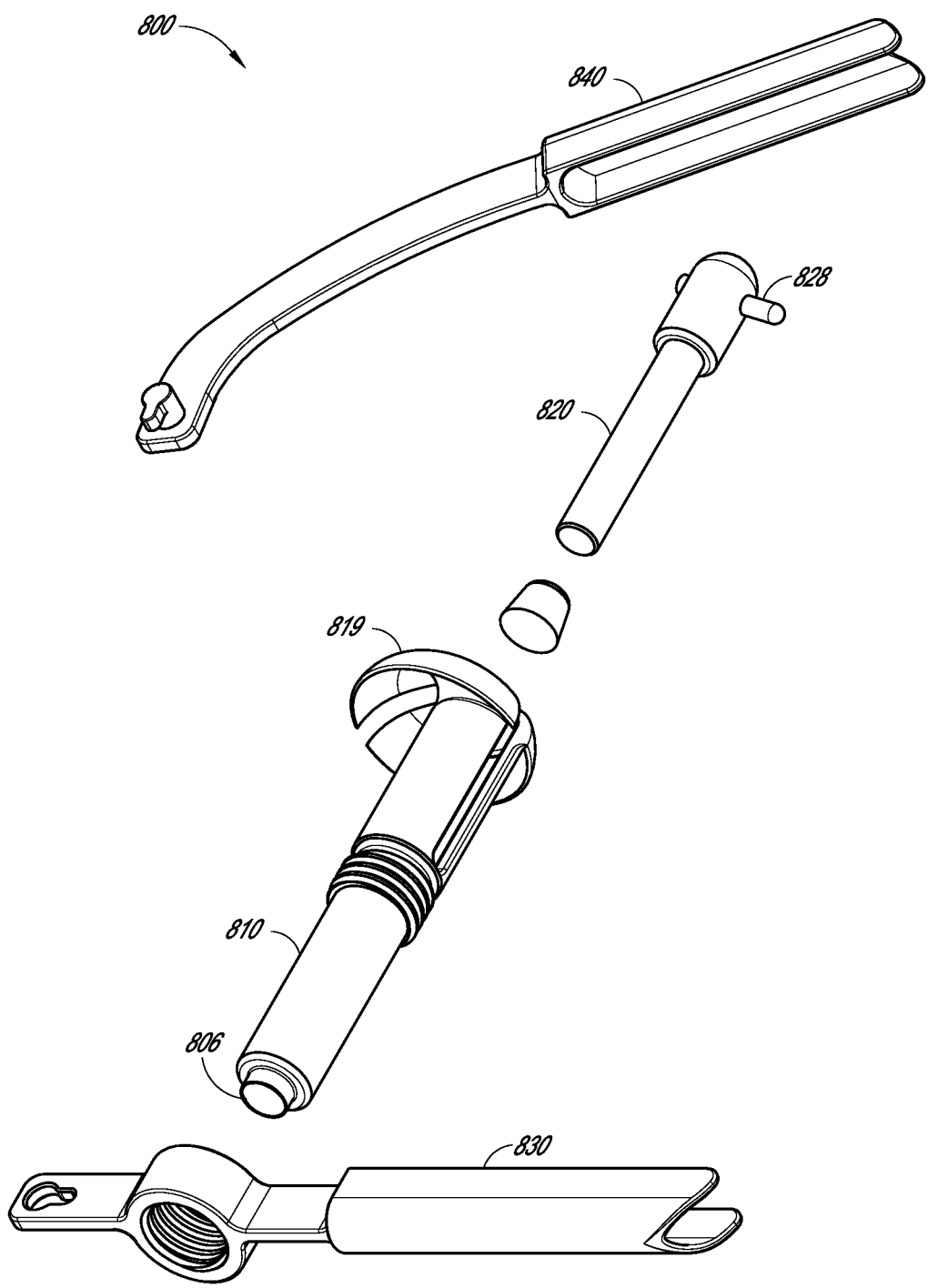
FIG. 16E illustrates an exploded view of the delivery tool of FIG. 16D.

According to some embodiments, once a reverse taper site has been created in the targeted joint or other portion of the patient (and, where applicable, the guide pin or other member has been removed), a clinician can deliver the implant to the implant site using a mechanically-assisted delivery tool or introducer 800. One embodiment of such a tool is illustrated in FIGS. 16A-16C. Another embodiment of such a tool is illustrated in FIGS. 16D-16E. As shown, the delivery tool or introducer 800 can comprise, among other things, an introducer tube 810, a plunger 820, a handle 830 and a clamp 840.

Such mechanically-assisted delivery devices can be helpful in advancing the implant through the interior of an introducer tube against a relatively large resistance of backpressure. Such a resistive force can be particularly high when the implant comprises a relatively large taper angle θ. Accordingly, in some embodiments, the use of such delivery tools makes the delivery of reverse taper implants into corresponding implant sites possible, while allowing the clinician to safely and accurately guide the implant into a targeted anatomical implant site. In several embodiments, the delivery tool is capable of overcoming resistive forces of about 5 to about 20 pounds. In some embodiments, the delivery tool exerts a force about 5 to about 25. In some embodiments, the delivery device is operated by or with the assistance of one or more motors. For example, in some embodiments, the clamp is moved (e.g., rotated) relative to the handle using (or with the assistance of) one or more stepper motors and/or any other type of motor or actuator. In some embodiments, delivery of an implant through the introducer tube 810 is accomplished with at least some assistance from air or pneumatic pressure. For example, air or other fluid can be injected into the interior of the introducer tube once the implant is inserted therein. The delivery of air can be incorporated into a plunger member 820 (e.g., via one or more interior lumens) so that the implant can be advanced through the introducer tube 810 into the implant site using mechanical force (e.g., by moving the plunger 820 through the tube 810) and/or by injecting air and/or other fluids into the interior of the tube 810. The fluid openings through the plunger 820 and/or any other fluid passages can be placed in fluid communication with a compressor or other fluid generating device. Advancement of the implant through the introducer tube 810 can be accomplished by applying a vacuum along or near the distal end of the tube 810 (e.g., through one or more vacuum ports along the introducer tube 810). Such vacuum ports or openings can be placed in fluid communication with a vacuum or other suction generating device.

According to some embodiments, the delivery tool comprises one or more depth stop features or components to ensure that the implant being delivered to a target implant site is properly delivered into the target implant site. In some embodiments, the depth stop features help protect the structural integrity of the implant as the implant is being inserted within the target anatomical implant site.

In some embodiments, the delivery device comprises and/or is operatively coupled to one or more pressure gauges or other pressure or force measuring devices, members or features. Such gauges or other measurement devices can help ensure that a maximum backpressure or force is not exceeded when operating the device. This can help protect the integrity of the implant (e.g., to ensure that the structural integrity, water composition and/or other properties of the implant are maintained), protect the delivery device, protect the user and/or the patient and/or provide one or more other advantages or benefits.

According to some embodiments, the introducer tube 810 of the delivery tool or device 800 comprises one or more viewing windows that permit the implant to be viewed as it is being advanced through the device 800 to the implant site. In some embodiments, the introducer tube 800 (and thus the longitudinal axis along which the implant is advanced through the delivery tool or device) is substantially perpendicular with the surface of the bone or other anatomical site into which the implant will be delivered and/or the handle 830 of the device 800.

According to some embodiments, at least a portion of the interior of the introducer tube 810 comprises and/or is otherwise coated or lined with one or more absorbable or lubricious layers, materials and/or other substances. Such materials can help preserve the moisture level of the implant as it is being advanced through the introducer tube 810. The interior surface of the introducer tube can comprise a low coefficient of friction to facilitate the delivery of an implant through the delivery device or tool 800. In some embodiments, the effective coefficient of friction along the interior of the introducer tube can be lowered polishing such surfaces. As noted herein, the introducer, including its interior surfaces, can comprise surgical grade stainless steel.

According to some embodiments, the delivery tool or device 800 is incorporated into the drill bit configured to create a reverse tapered implant site. For example, such a combination device can be coupled to a drill or other mechanical device to first create the implant site. Then, the combination device can take advantage of the mechanical output generated by the drill and/or other mechanical or motorized device to help urge the implant through the introducer tube of the combination device.

Figure 17A:
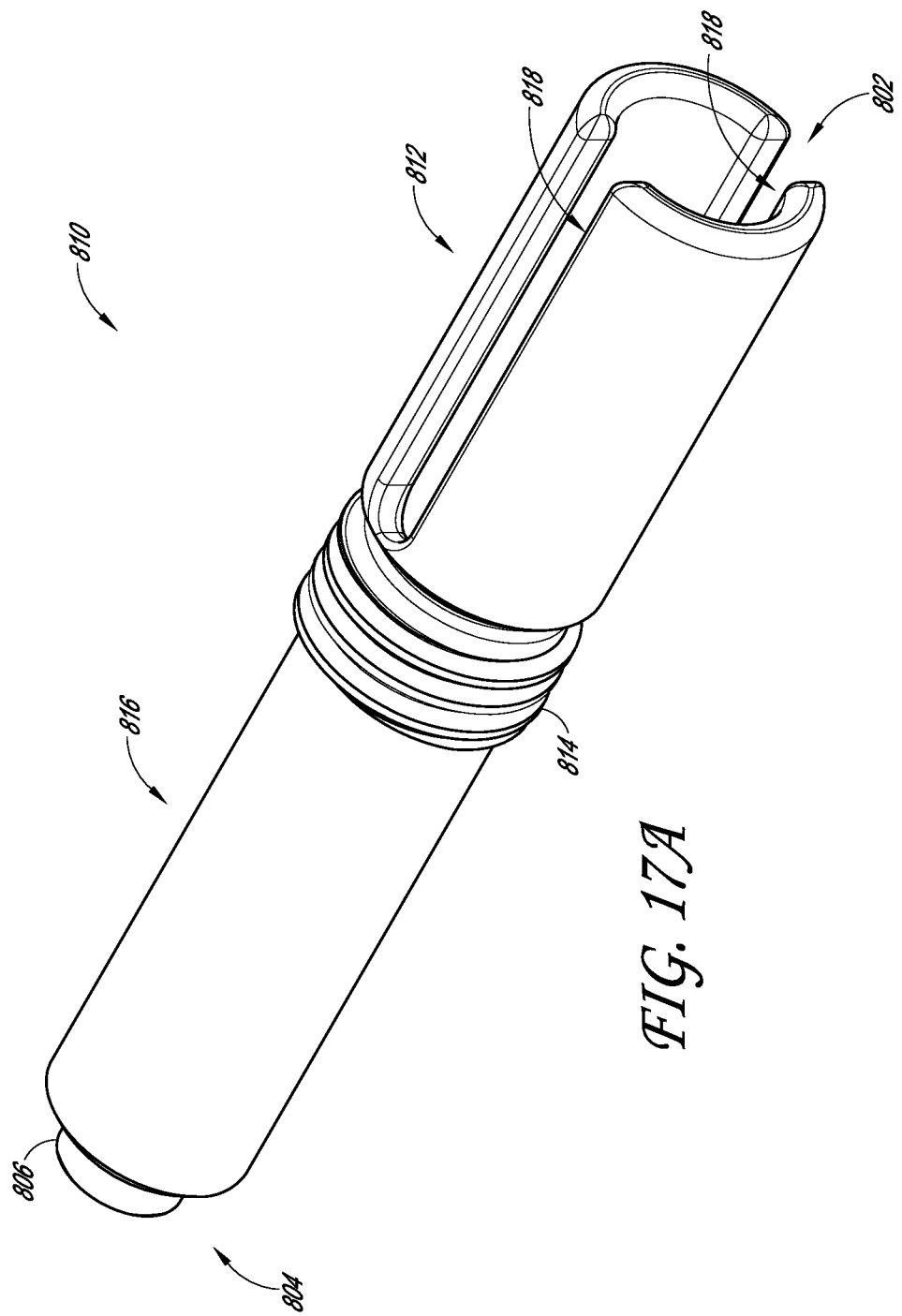
FIG. 17A illustrates a perspective view of an introducer.
Figure 17B:
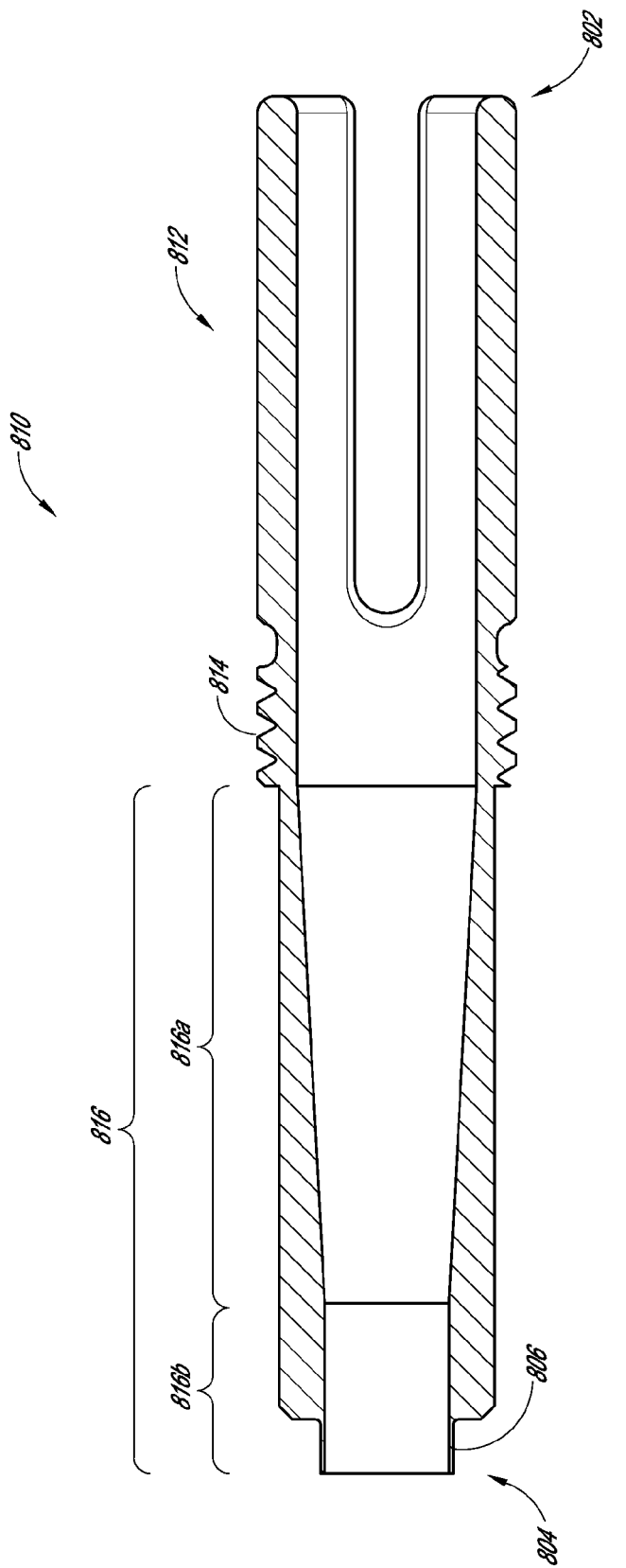
FIG. 17B illustrates a cross-sectional view of the introducer of FIG. 17A.

As illustrated in FIGS. 17A and 17B, the introducer tube 810 of the mechanically-assisted delivery tool 800 can be hollow and generally cylindrical in shape. However, in other embodiments, the shape, general structure and/or other characteristics of the tube 810 can be different than disclosed herein. In some embodiments, the introducer tube 810 comprises an externally threaded portion 814, a proximal portion 812 extending between a proximal end 802 and the externally threaded portion 814, and a distal portion 816 extending between the externally threaded portion 814 and a distal end 804. The distal end 804 of the introducer 810 can comprise a neck or other narrowed portion 806.

As best illustrated in the longitudinal cross-sectional view of FIG. 17B, the internal diameter of the introducer tube 810 can vary along at least a portion of the tube's length. For example, in the depicted embodiment, the proximal portion 812 of the introducer or introducer tube 810 has a generally constant, consistent or flat inner diameter. In addition, as shown, the distal portion 816 of the introducer tube 810 can comprise a generally tapered or sloped portion 816a, such that the inside diameter of the tube is progressively reduced in the proximal to distal direction. In some embodiments, the slope along the interior surface of the tube 810 can be generally linear. However, in other arrangements, the slope of the interior surface of the tube 810 is at least partially non-linear (e.g., curved, rounded, irregular, etc.), either in addition to or in lieu of any generally linear and/or constant portions, as desired or required for a particular application or use. Further, in some embodiments, as illustrated in the cross-sectional view of FIG. 17B, a portion 816b proximate the distal end 804 comprises a generally constant or flat (e.g., non-sloped) inner surface or diameter. Further, in other embodiments, the inner diameter or surface, length, other dimensions and/or other details or properties of the introducer tube 810, including any internal tapered or sloped portions 816a, any generally cylindrical (e.g., constant, flat, non-sloped, etc.) interior portions 816b, any neck portions 806 and/or the like can be different than shown in FIGS. 17A-17B and described herein.

According to some embodiments, the proximal portion 812 of the introducer tube 810 includes one or more slits or other openings 818. As shown, such a slit 818 can begin adjacent to or near the externally threaded portion 814 of the tube 810 and can extend to or near the proximal end 802 of the tube 810. In some embodiments, the proximal portion 812 of the introducer tube includes two (or more) slits 818 located opposite each other in the introducer 810 to form a channel through the proximal portion 812. In some embodiments, for example as shown in FIGS. 16D-16E, the proximal portion 812 of the introducer tube 810 comprises a flange 819 or other protruding or flared portion extending outwardly (e.g., radially outwardly in a continuous or intermittent manner) from or near the proximal end 802. In other embodiments, the flange or other protruding member 819 can be located along one or more other longitudinal locations of the tube 810, as desired or required. The flange 819 can be substantially or generally flat and/or can include any other shape (e.g., curved, fluted, etc.). The flange 819 can be integrally formed or attached to the proximal portion 812 of the tube 810. Alternatively, the flange 819 can be a separate member that can be selectively attached to or removed from the tube 810 and/or any other portion of the tool 800.

Figure 18:
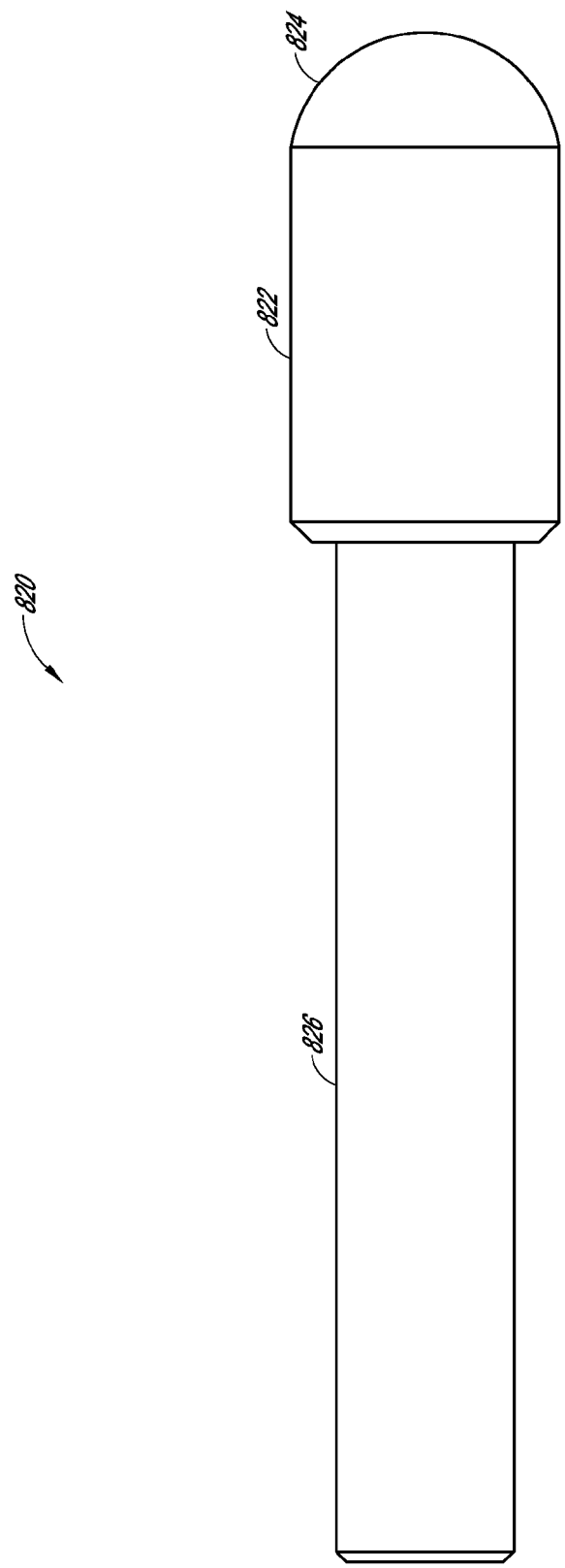
FIG. 18 illustrates a side view of a plunger.

With reference to FIG. 18, the plunger 820 of the tool 800 can be generally cylindrical in shape with an enlarged proximal head portion 822 that includes a domed proximal end 824. In some embodiments, in a properly assembled mechanically-assisted delivery tool 800, the plunger 820 is shaped, sized and otherwise configured to slide within the hollow interior passage of the introducer tube 810. Thus, as discussed in greater detail herein, by actuating the tool, a clinician or other user can selectively move the plunger within an interior portion of the introducer tube 810 in order to urge an implant (e.g., a tapered implant) through the distal end of the tube and into a targeted implant site of a patient.

With continued reference to FIG. 18, the main body 826 of the plunger 820 can have a diameter approximately the same as and/or slightly smaller than the inner diameter of the neck portion 806 and distal portion 816b of the introducer 810. In some embodiments, as illustrated in the embodiment of FIG. 16E, the head portion 822 of the plunger 820 includes a motion limiter or depth stop 828. The motion limiter 828 can comprise one or more knobs, protrusion members and/or other members or features that generally extend outwardly from the head portion 822 of the plunger. In some embodiments, such a motion limiter, depth stop member or feature and/or other protruding member 828 is configured to slide within the slit(s) 818 or other openings of the introducer tube 810. These features can help prevent or otherwise limit distal movement of the plunger 820 relative to the introducer tube (e.g., when the motion limiter or depth stop 828 contacts or abuts the base of the slit(s) 818). Further, such a feature can help prevent or limit rotation of the plunger relative to the tube 810 during use. In some embodiments, the head portion 822 of the plunger 820 comprises a diameter approximately the same as and/or slightly smaller than the inner diameter of the proximal portion 812 of the introducer tube 810. Accordingly, movement of the plunger 820 relative to the tube 810, beyond a particular point, will generally be prevented or limited when the head portion 822 contacts or abuts the narrowing inner diameter of the tapered portion 816a of the distal portion 816 of the introducer tube. Therefore, the corresponding abutting features of the plunger 820 and the introducer tube 810 can advantageously help limit the depth to which an implant (e.g., tapered implant) can be delivered relative to an implant site of a patient. In some embodiments, this can help improve the safety and efficacy of the implant, the related tools and the implant procedure.

According to some embodiments, as illustrated in FIG. 19A, the handle 830 of the delivery tool 800 comprises a generally circular internally threaded nut portion or introducer tube receiving portion 834. As shown, the threaded nut portion or introducer tube receiving portion 834 can be interposed between an elongate proximal section 832 and an elongate distal section 836. In the depicted arrangement, the introducer tube receiving portion 834 is located closer to the distal section 836 of the handle 830. However, in other embodiments, the portion 834 can be located along any other portion of the handle 830, as desired or required. Further, the introducer tube receiving portion 834 can include one or more other engagement or connection features or devices (e.g., snap connections, press-fit or friction-fit connections, screws or other fasteners, adhesives, etc.), either in lieu of or in addition to a threaded connection.

With continued reference to the perspective view of the handle illustrated in FIG. 19A, the proximal portion or section 832 of the handle can be longer than the distal portion or section 836. In other words, as noted above, the introducer tube receiving portion 834 can be positioned closer to the distal end than the proximal end of the handle 830. However, in other embodiments, the introducer tube receiving portion 834 is located at or near between the distal and proximal ends of the handle, or at, near or closer to the proximal end of the handle, as desired or required.

As shown in FIG. 19A, the proximal section 832 and distal section 836 can extend in generally opposite directions from the nut or introducer tube receiving portion 834. However, in some embodiments, a longitudinal axis of the distal section 836 is slightly offset from a longitudinal axis of the proximal section 832. Such a configuration can assist with the coupling of the clamp 840 as described herein. For example, in the illustrated embodiment (e.g., when viewed from the top as shown in FIG. 19B), a centerline or orientation of the distal section or portion 836 of the handle is generally offset with respect to the centerline or orientation of the proximal section 832. The introducer tube receiving portion 834 can be sized, shaped and otherwise configured so that the distal section 816 of the introducer tube 810 can pass through the opening of the introducer receiving portion 834. Further, the externally threaded portion 814 of the introducer tube 810 can operatively engage and mate with the internal threaded portion of the introducer tube receiving portion 834. As noted above, in other embodiments, the handle 830 can engage the introducer tube 810 using one or more other attachment methods, features or devices (e.g., fasteners, snap-fit or friction-fit connections, other mating connections or couplings, adhesives, etc.) either in addition to or in lieu of a threaded connection.

In some embodiments, the elongate proximal section or portion 832 of the handle comprises a grasping portion 838 configured to be selectively gripped and manipulated by a user during use. The grasping portion 838 can be contoured, shaped and/or otherwise configured to improve the user's grip on the handle 830. In the illustrated embodiment, the distal section or portion 836 of the handle comprises a generally rectangular cross-section. However, the distal portion and/or any other portion of the handle 830 can include any other shape (e.g., circular, oval, square, polygonal, etc.). When the nut portion of introducer receiving portion 834 is oriented horizontally, the distal section 836 of the handle comprises a generally vertical shape so that it is taller than it is deep.

According to some embodiments, the distal section 836 of the handle 830 comprises a keyhole 837 or other opening for coupling to the clamp 840 of the device. The keyhole 837 or other opening can be configured to allow the clamp 840 to be quickly and easily connected to and/or disconnected from the handle 830. In other arrangements, however, the clamp 840 can be permanently or substantially permanently attached to the handle 830. In other embodiments, the size, shape, orientation, and/or other details or properties of the handle 830 can be different than shown in FIGS. 19A-19B and described herein.

Figure 20A:
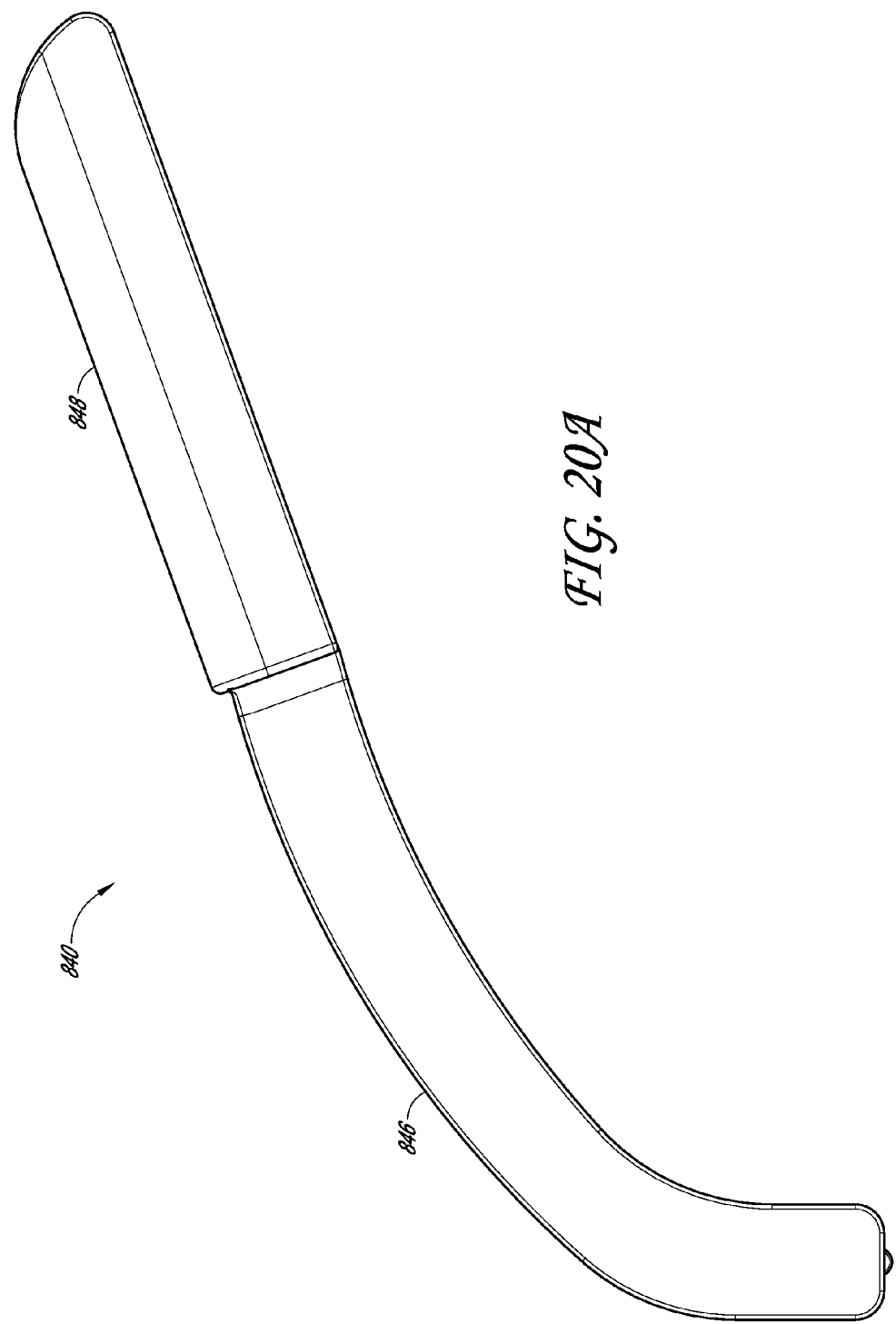
FIG. 20A illustrates a side view of a clamp.
Figure 20B:
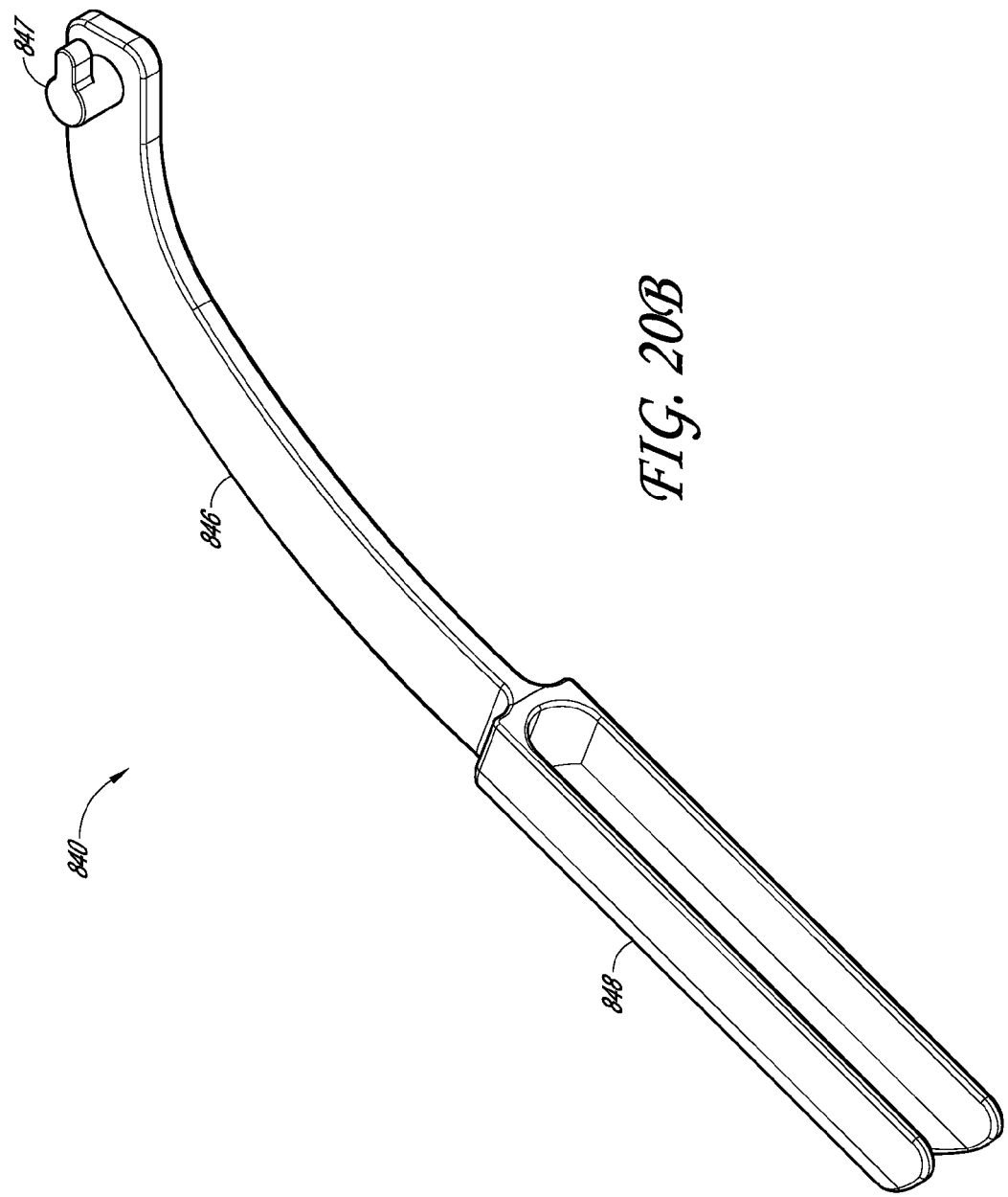
FIG. 20B illustrates another view of the clamp of FIG. 20A.

With reference to FIGS. 20A and 20B, the clamp 840 can comprise an elongate member having a slight curve. A proximal portion of the clamp 840 can include a handle or grasping portion 848 that a user can grip during use of the device. A distal portion 846 of the clamp 840 is generally sized, shaped and otherwise configured such that it can be moved within the slit 818 of the introducer tube 810. In some embodiments, as illustrated herein, the distal end of the clamp 840 comprises a key 847 for insertion within the keyhole or other opening 837 of the handle 830 in order to couple the clamp to the handle.

Therefore, the handle 830 and the clamp 840 can be connected to one another about a hinge or other rotatable point, thereby permitting the handle to be selectively rotated and/or otherwise moved relative to the clamp. As discussed in greater detail herein, such a relative rotation between the clamp and the handle can be used to provide the mechanical force necessary to move the plunger 820 within the introducer tube 810. This can advantageously urge an implant (e.g., tapered hydrogel implant) through the tube 810 and into a target recess of an implant site. Accordingly, the forces created by moving the clamp relative to the handle can help move an implant against relatively high back-forces (e.g., against relatively high friction and/or other resistive forces) within the introducer tube. Such movement of the implant can be particularly difficult for reverse tapered implants where at least a portion of such implants experiences generally high radially compressive forces while being moved through an interior lumen or other opening of the introducer tube 810.

According to some embodiments, to assemble the delivery device 800 in preparation for use, the user inserts the implant 10 (e.g., reverse tapered implant, other joint implant, etc.) into the introducer tube 810 via the proximal end 802. The plunger 820 can then be inserted into the proximal end 802 of the introducer tube 810 and used to distally advance the implant 10 within the introducer tube 810. Once the handle 830 is coupled to the introducer tube 810 (e.g., by threading the nut portion or introducer tube receiving portion 834 onto the externally threaded portion 814 of the introducer tube 810), the clamp 840 can be coupled to the handle 830 by inserting the key 847 (or other protruding portion or feature) of the clamp 840 into the keyhole 837 (or other opening) of the handle 830. When assembled, e.g., as illustrated in FIGS. 16A, 16C, 16D and 21A-21C, the clamp 840 is generally positioned and movable within the slit 818 of the introducer tube 810.

As discussed in greater detail herein, the clamp 840 can be rotatably attached to the handle 830 (e.g., at a hinge point), thereby allowing a user to selectively rotate or otherwise move the clamp relative to the handle (e.g., to move the clamp 840 toward or away from the handle 830 within the slit, groove or other opening of the introducer tube 810). In some embodiments, an offset between the distal section 836 and proximal section 832 of the handle 830 permits the distal portion 846 of the clamp 840 to be aligned with the slit 818 in the introducer tube so that the clamp can be selectively moved within the slit 818 when the clamp 840 and handle 830 are coupled to one another (e.g., via the key 847-keyhole 837 joint or a similar feature or mechanism). Therefore, in some embodiments, the delivery device 800 is configured for quick, easy and convenient assembly and disassembly for cleaning, sterilization, repair, maintenance and/or any other reason or purpose.

According to some embodiments, the various components of the mechanically-assisted delivery device 800 comprise one or more rigid and/or semi-rigid materials that are configured to withstand the forces, moments, chemicals and/or other substances, temperature fluctuations and/or other elements to which they may be exposed. For example, the components of the implant delivery device can comprise one or more metals (e.g., stainless steel, other surgical steel, other types of steel, etc.), alloys, plastics and/or the like. Such materials can permit the device to be autoclaved, sterilized or otherwise cleaned during a specific disinfection protocol. In addition, the structural and other physical characteristics of the device can permit the user to exert the necessary forces using the device to deliver implants of various sizes, shapes and/or configurations through the corresponding introducer tube and into a target implant site of a patient.

In use, the distal neck portion 806 of the introducer tube 810 can be positioned at least partially within the opening, recess or other implant site into which the implant 10 will be secured. In some embodiments, the introducer tube 810 is sized, shaped and otherwise configured to that the neck portion 806 fits generally snugly within the implant site. To deliver the implant 10 (e.g., reverse taper implant) through the device 800 and into the targeted implant site, the user can urge the clamp 840 toward the handle 830 of the device (e.g., so that the clamp rotates or otherwise moves relative to the handle). According to some embodiments, as the distal portion 846 of the clamp 840 moves downwardly through the slit, slot or other opening 818 of the introducer tube 810, a portion of the clamp 840 (e.g., the distal portion 846) contacts the plunger 820 (e.g., the domed proximal end 824), and urges the plunger 820 distally within the introducer tube 810.

As illustrated in FIGS. 21A-21C, such a movement, in turn, urges the implant 10 distally within the introducer tube 810. As the implant 10 is urged deeper (e.g., more distally) into the interior of the introducer tube 810, the implant 10 may become radially compressed by the interior shape (e.g., tapered portion 816a) of the introducer tube 810. If sufficient force is applied to the implant 10 by moving the clamp relative to the handle, the implant 10 can pass through the neck portion 806 of the introducer tube and into the implant site. In some embodiments, the motion limiter 828 or similar feature of the plunger 820 can contact the distal end of the slit or similar opening 818 of the introducer tube 810 when the implant 10 has been released from the delivery device 800 into the implant site. As depicted in FIG. 21C, this can help prevent the plunger 820 from continuing to move toward and into the implant site and possibly damaging the implant site and/or the implant 10. While the user grasps the handle 830 and the clamp 840 with one hand, he or she can apply a required force on the flange 819 that extends outwardly from the proximal end 802 of the introducer tube 810 with the other hand to stabilize and control the introducer 810.

Accordingly, the mechanically-assisted delivery devices disclosed herein, or equivalents thereof, can facilitate the compression and delivery of reverse tapered implants within a target implant site. In some embodiments, the mechanically-assisted delivery device can be configured to be operated at least partially with the assistance of a mechanical motor, a pneumatic device and/or another external device. For example, the clamp of the device can be moved relative to the handle by or with the assistance of one or more motors (e.g., regulated by a user using a button, knob, dial and/or other controller). Such embodiments can further facilitate the delivery of implants within an implant site of a patient.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

What is claimed is:

1. A method of treating a targeted joint, comprising:
creating a recess in a bone located at or near the targeted joint, the recess comprising a wedge shape, wherein creating the recess comprises creating a cylindrical opening in the bone and removing additional tissue along the cylindrical opening to create the wedge shape;
wherein the recess in a bone comprises a surface opening along an outer surface of the bone, a bottom opening along the distal end of the recess and side walls generally extending between the surface opening and the bottom opening, wherein a diameter or other cross-sectional dimension of the bottom opening is larger than a diameter or other cross-sectional dimension of the surface opening to provide the wedge shape to the recess;
radially compressing an implant having a wedge shape, the implant comprising a first end and a second end and a body extending between the first end and the second end, the second end being generally opposite of said first end;
wherein when the implant is in a radially uncompressed state, a diameter or other cross-sectional dimension of the first end is smaller than a diameter or other cross-sectional dimension of the second end;
while the implant is in a radially compressed state, inserting the implant within the recess, wherein the second end of the implant is inserted first within the recess;
wherein the second end of the implant is adjacent the bottom opening of the recess, and wherein the first end of the implant is adjacent the surface opening of the recess when the implant is positioned within the recess; and
releasing the implant from a radially compressed state to a less compressed state, when the implant is positioned within the recess;
wherein, when the implant is in a less compressed state, the diameter or other cross-sectional dimension of the second end of the implant is larger than the diameter or other cross-sectional dimension of the surface opening of the recess; and
wherein, when the implant is in a radially uncompressed state, the body of the implant imparts a radial force at least partially along the side walls of the recess, thereby securing the implant within the recess.

2. The method of claim 1,
wherein creating the recess in a bone comprises using a tool comprising a cutter configured to selectively enlarge the recess near the bottom opening along the distal end of the recess;
wherein the tool is cannulated, the tool being configured to be positioned over a guide pin to place a working end of the tool at or near a targeted location of the recess; and
wherein the implant is radially compressed and inserted within the recess using an introducer.

3. The method of claim 1, wherein creating the recess in a bone comprises using a tool comprising a cutter configured to selectively enlarge the recess near the bottom opening along the distal end of the recess.

4. The method of claim 3, wherein the tool is cannulated, the tool being configured to be positioned over a guide pin to place a working end of the tool at or near a targeted location of the recess.

5. The method of claim 1, wherein the implant is radially compressed and inserted within the recess using an introducer.

6. The method of claim 5, wherein the implant is moved through an interior of the introducer using a plunger or other pusher member.

7. The method of claim 5, wherein the implant is moved through an interior of the introducer using a mechanically-assisted device.

8. The method of claim 7, wherein the mechanically-assisted device comprises a handle and a clamp coupled to the handle, wherein moving the clamp relative to the handle urges a plunger within an introducer to radially compress the implant and insert the implant within the recess.

9. The method of claim 1, wherein the implant comprises a hydrogel.

10. The method of claim 1, wherein a ratio of the diameter or other cross-sectional dimension of the second end of the implant to the diameter or other cross-sectional dimension of the first end of the implant is approximately between 1.05 and 1.3.

11. The method of claim 1, wherein the diameter or other cross-sectional dimension of the second end of the implant is approximately 5% to 25% larger than the diameter or other cross-sectional dimension of the implant.

12. The method of claim 1, wherein the recess is located within or near at least one of a toe, finger, ankle, knee, shoulder, hip or other joint.

13. A method of treating a targeted joint, comprising:
creating a recess in a bone located at or near the targeted joint, the recess comprising a wedge shape with a bottom opening having a larger diameter or other cross-sectional dimension than a surface opening, wherein creating the recess comprises creating a cylindrical opening in the bone and removing additional tissue along the cylindrical opening to create the wedge shape;
at least partially radially compressing an implant having wedge shape, wherein when the implant is in a radially uncompressed state, a diameter or other cross-sectional dimension of a first end of the implant is smaller than a diameter or other cross-sectional dimension of a second end of the implant;
while the implant is at least partially radially compressed, inserting the implant within the recess, wherein the second end of the implant is inserted first within the recess; and
allowing the implant to be released from a radially compressed state to a less compressed state when the implant is positioned within the recess;
wherein, when the implant is in a less compressed state, the diameter or other cross-sectional dimension of the second end of the implant is larger than the diameter or other cross-sectional dimension of the surface opening of the recess; and
wherein, when the implant is in a radially uncompressed state, the body of the implant imparts a radial force against walls of the recess, thereby helping to secure the implant within the recess.

14. The method of claim 13,
wherein the implant is at least radially compressed and inserted within the recess using an introducer;
wherein creating the recess in a bone comprises using a tool with a cutter; and
wherein the tool is configured to be positioned over a guide pin to place a working end of the tool at or near a targeted location of the recess.

15. The method of claim 14, wherein the tool is cannulated, the tool being configured to be positioned over a guide pin to place a working end of the tool at or near a targeted location of the recess.

16. The method of claim 13, wherein creating the recess in a bone comprises using a tool with a cutter.

17. The method of claim 13, wherein the implant is at least partially radially compressed and inserted within the recess using an introducer.

18. A method of treating a targeted joint, comprising:
creating an opening in a bone located at or near the targeted joint, the opening comprising a wedge shape with a bottom area having a larger diameter or other cross-sectional dimension than a surface area;
wherein creating the opening comprises creating a cylindrical opening in the bone and removing additional tissue along the cylindrical opening to create the wedge shape;
at least partially radially compressing an implant having wedge shape, wherein when the implant is in a radially uncompressed state, a diameter or other cross-sectional dimension of a first end of the implant is smaller than a diameter or other cross-sectional dimension of a second end of the implant;
while the implant is at least partially radially compressed, inserting the implant within the opening; and
allowing the implant to be released from a radially compressed state to a less compressed state when the implant is positioned within the opening.

19. The method of claim 18,
wherein the implant is at least partially radially compressed and inserted within the opening using an introducer;
wherein creating the opening in a bone comprises using a tool with a cutter; and
wherein the tool is configured to be positioned over a guide pin to place a working end of the tool at or near a targeted location of the opening.

20. The method of claim 18, wherein the implant is at least partially radially compressed and inserted within the opening using an introducer.

21. The method of claim 18, wherein, when the implant is in a radially uncompressed state, the body of the implant imparts a radial force against walls of the opening, thereby helping to secure the implant within the opening.

22. The method of claim 18, wherein creating a wedge shape opening comprises using a single device or using at least two devices.

\* \* \* \* \*